United States Patent
Bender et al.

(10) Patent No.: US 7,034,045 B1
(45) Date of Patent: Apr. 25, 2006

(54) MONOFLUOROALKYL DERIVATIVES

(75) Inventors: David Michael Bender, Indianapolis, IN (US); Buddy Eugene Cantrell, Zionsville, IN (US); Andrew Hendley Fray, Indianapolis, IN (US); Winton Dennis Jones, Carmel, IN (US); William David Miller, Indianapolis, IN (US); David Mitchell, Indianapolis, IN (US); Richard Lee Simon, Greenwood, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/958,262

(22) PCT Filed: Apr. 17, 2000

(86) PCT No.: PCT/US00/08734

§ 371 (c)(1),
(2), (4) Date: Oct. 5, 2001

(87) PCT Pub. No.: WO00/66546

PCT Pub. Date: Nov. 9, 2000

Related U.S. Application Data

(60) Provisional application No. 60/177,566, filed on Jan. 21, 2000, provisional application No. 60/131,771, filed on Apr. 30, 1999.

(51) Int. Cl.
*A61K 31/44* (2006.01)
*A61K 31/40* (2006.01)
*A61K 31/38* (2006.01)
*A61K 31/275* (2006.01)
*A61K 31/195* (2006.01)

(52) U.S. Cl. ............ 514/355; 514/357; 514/429; 514/438; 514/523; 514/524; 514/539; 514/562; 514/597; 514/605; 546/316; 548/577; 558/408; 558/413; 560/12; 560/430; 564/49; 564/99

(58) Field of Classification Search .......... 564/99, 564/49; 514/605, 355, 357, 429, 438, 523, 514/524, 539, 562, 597; 546/316; 548/577; 549/75; 558/408, 413; 560/12, 430
See application file for complete search history.

(56) References Cited

U.S. PATENT DOCUMENTS

| 4,186,129 A | 1/1980 | Huth et al. ............ 548/186 |
| 6,174,922 B1 | 1/2001 | Arnold et al. ............ 514/604 |
| 6,358,981 B1 * | 3/2002 | Arnold et al. ............ 514/331 |

FOREIGN PATENT DOCUMENTS

| WO | WO 96/18615 | 12/1994 |
| WO | WO 98/33496 | 2/1997 |

(Continued)

OTHER PUBLICATIONS

G. M. Alvernhe et al: *J. Org. Chem.*, vol. 46, No. 24, 1981, pp. 4938-4048, XP002155661.
H. O. House et al: *J. Am. Chem. Soc.*, vol. 81, 1959, pp. 4733-4737, XP002155662.
K. A. Van Houten et al: *J. Am. Chem. Soc.*, vol. 120, No. 24, 1998, pp. 5864-5872, XP002155663.
U.S. Appl. No. 60/224,573, Bender et al.
U.S. Appl. No. 60/229,394, Bender et al.
U.S. Appl. No. 60/205,822, Aikins et al.
U.S. Appl. No. 60/206,003, Arnold et al.
U.S. Appl. No. 60/211,365, Knoblesdorf et al.
U.S. Appl. No. 60/224,497, Forman et al.
U.S. Appl. No. 60/209,675, Knobelsdorf et al.
U.S. Appl. No. 60/240,422, Clemens et al.
U.S. Appl. No. 60/296,008, Davison et al.
I. Fleming et al: *J. Chem. Soc. Perkin Trans. I.*, 1979, pp. 829-837, XP002155664.

(Continued)

*Primary Examiner*—Peter O'Sullivan
(74) *Attorney, Agent, or Firm*—Danica Hostettler; Nelsen L. Lentz; John A. Cleveland, Jr.

(57) ABSTRACT

The present invention provides certain monofluoroalkyl derivatives useful for potentiating glutamate receptor function in a mammal and therefore, useful for treating a wide variety of conditions, such as psychiatric and neurological disorders.

25 Claims, No Drawings

FOREIGN PATENT DOCUMENTS

| | | |
|---|---|---|
| WO | WO 00/06148 | 7/1998 |
| WO | WO 00/06157 | 7/1998 |
| WO | WO 00/06158 | 7/1998 |
| WO | WO 00/06156 | 7/1999 |

OTHER PUBLICATIONS

H. Brunner et al: *Chem. Ber.*, vol. 123, 1990, pp. 1029-1038, XP002155665.

G. Drefahl et al: *Chem. Ber.*, vol. 94, 1961, pp. 915-922, XP002155666.

Database Chemabs Online, Chemical Abstracts Service, Columbus, Ohio, US, STN, Caplus accession No. 1993:56667, XP002155667.

Database Chemabs Online, Chemical Abstracts Service, Columbus, Ohio, STN, Caplus accession No. 1988:569967, XP002155668.

* cited by examiner

MONOFLUOROALKYL DERIVATIVES

This is a 371 of PCT/US00/08734 filed Apr. 17, 2000 which claims priority to U.S. Provisional Application No. 60/177,566 filed Jan. 21, 2000 and U.S. Provisional Application No. 60/131,771 filed Apr. 30, 1999.

The present invention relates to the potentiation of glutamate receptor function using certain monofluoroalkyl derivatives. It also relates to novel monofluoroalkyl derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are not fully understood.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulfonamides, S-oxides and homologs which are said to potentiate membrane currents induced by kainic acid and AMPA.

U.S. Pat. No. 3,143,549 discloses certain phenylalkylsulfamides, including 1-methyl-2-phenylethyl dimethylsulfamide. The compounds are said to have central nervous system activity, in particular antianxiety and tranquilizing properties.

U.S. Pat. No. 3,267,139 discloses certain N'-trimethylacetyl-N-phenylalkylsulfamides and -phenylcyclopropylsulfamides having central nervous system activity and anticonvulsant activity. The compounds are also said to produce Parkinson-like symptoms in experimental animals.

U.S. Pat. No. 3,860,723 discloses a method of increasing feed intake of healthy animals using certain phenylalkylsulfamides.

Foye et al., *J. Pharm. Sci.* (1971), 60(7), 1095–6 discloses certain phenylalkyl methylsulfonamides including N-1-methyl-2-phenylethyl methanesulfonamide, having hypotensive activity.

British Patent Specification Number 1,059,360 discloses certain phenylalkylsulfamides having activity as sedatives, narcotics and anticonvulsants, including 1-(1-methyl-2-phenylethylaminosulphonyl)piperidine.

U.S. Pat. No. 4,210,749 discloses N-1-methyl-2-phenyl-3-methoxy ethyl butane-sulfonamide.

Gualtieri et al., *J. Pharm. Sci.*, (1973), 62(5), 849–851 discloses N-1-methyl-2-phenylethyl butanesulfonamide and its evaluation as a mosquito repellent.

Foye et al., *J. Pharm. Sci.* (1979), 68(5), 591–5 discloses N-1-methyl-2-(4-chlorophenyl)ethyl methane-sulfonamide.

Foye and Sane, *J. Pharm. Sci.* (1977), 66(7), 923–6 discloses N-methanesulfonyl and N-trifluoromethanesulfonyl derivatives of amphetamines and certain 4-substituted analogs thereof, and their evaluation for central nervous system and anorexic effects.

European patent application publication no. EP-A1-0657442 discloses certain naphthyloxyacetic acid derivatives as PEG2 agonists and antagonists. N-( 2,2-diphenylethyl)-methanesulfonamide is disclosed as an intermediate at page 53, line 38.

U.S. Pat. No. 3,629,332 discloses certain N-aryl- and N-heteroarylalkyl fluoroalkane sulfonamides as plant growth modifiers, including N-(alpha-methylphenylethyl) trifluoromethanesulfonamide, difluoromethanesulfonamide and fluoromethanesulfonamide. Some of the compounds are also said to have other biological activity, including insecticidal, acaricidal, nematicidal, analgesic and anti-inflammatory activity.

Ampakines have been shown to improve memory in a variety of animal tests. Staubli et al., *Proc. Natl. Acad. Sci.*, Vol. 91, pp 777–781, 1994, *Neurobiology,* and Arai et al., *The Journal of Pharmacology and Experimental Therapeutics*, 278: 627–638, 1996.

In addition, certain sulfonamide derivatives which potentiate glutamate receptor function in a mammal have been disclosed in International Patent Application Publication WO 98/33496 published Aug. 6, 1998 and International Patent Application Publication WO 99/43285 published Sep. 2, 1999.

The present invention provides compounds of formula I:

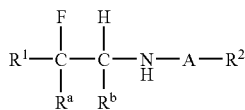

formula I wherein:
A represents $SO_2$, $CO_2$, or CONH;
$R^a$ represents (1–6C)alkyl, (2–6C)alkenyl, —(1–4C)alkyl (3–8C)cycloalkyl, or —(1–4C)alkylaromatic;
$R^b$ represents H, (1–6C)alkyl, (2–6C)alkenyl, —(1–4C)alkyl(3–8C)cycloalkyl, or —(1–4C)alkylaromatic; or
$R^a$ and $R^b$ together with the carbon atoms to which they are attached form a (3–8C) saturated carbocyclic ring, a (3–8C) saturated carbocyclic ring containing a heteroatom selected from the group consisting of sulfur or oxygen, or a (5–8C) carbocyclic ring containing one double bond;
$R^1$ represents an unsubstituted or substituted aromatic group, an unsubstituted or substituted heteroaromatic group, or an unsubstituted or substituted (5–8C)cycloalkyl group;
$R^2$ represents (1–6C)alkyl, (3–6C)cycloalkyl, (1–6C)fluoroalkyl, (1–6C)chloroalkyl, (2–6C)alkenyl, (1–4C) alkoxy(1–4C)alkyl, phenyl which is unsubstituted or substituted by halogen, (1–4C)alkyl or (1–4C)alkoxy, or when A represents $SO_2$, a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group;
or a pharmaceutically acceptable salt thereof.

The present invention further provides a method of potentiating glutamate receptor function in a patient, which comprises administering to said patient an effective amount of a compound of formula I.

The present invention provides a method of treating cognitive disorders in a patient, which comprises administering to said patient an effective amount of a compound of formula I.

In addition, the present invention further provides a method of treating cognitive deficits associated with psychosis in a patient, which comprises administering to said patient an effective amount of a compound of formula I.

According to another aspect, the present invention provides the use of a compound of formula I, or a pharmaceutically acceptable salt thereof for the manufacture of a medicament for potentiating glutamate receptor function.

In addition, the present invention provides the use of a compound of formula I or a pharmaceutically acceptable salt thereof for potentiating glutamate receptor function.

The invention further provides pharmaceutical compositions comprising, a compound of formula I and a pharmaceutically acceptable diluent or carrier.

The present invention further includes compounds of the formula:

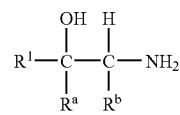

wherein
$R^a$ represents (1–6C)alkyl, (2–6C)alkenyl, —(1–4C)alkyl (3–8C)cycloalkyl, or —(1–4C)alkylaromatic;
$R^b$ represents H, (1–6C)alkyl, (2–6C)alkenyl, —(1–4C) alkyl(3–8C)cycloalkyl, or —(1–4C)alkylaromatic; or
$R^a$ and $R^b$ together with the carbon atoms to which they are attached form a (3–8C) saturated carbocyclic ring, a (3–8C) saturated carbocyclic ring containing a heteroatom selected from the group consisting of sulfur or oxygen, or a (5–8C) carbocyclic ring containing one double bond;
$R^1$ represents an unsubstituted or substituted aromatic group, an unsubstituted or substituted heteroaromatic group, or an unsubstituted or substituted (5–8C)cycloalkyl group;
or a pharmaceutically acceptable salt thereof;

with the proviso that when $R^a$ is methyl, then $R^1$ is other than 4-bromophenyl.

This invention also encompasses novel intermediates, and processes for the synthesis of the compounds of formula I.

In this specification, the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Hungtington's chorea, myoclonus and Parkinson's disease; reversal of drug-induced states (such as cocaine, amphetamines, alcohol-induced states); depression; attention deficit disorder; attention deficit hyperactivity disorder; psychosis; cognitive deficits associated with psychosis, drug-induced psychosis, and sexual dysfunction. The compounds of formula I may also be useful for improving memory (both short term and long term) and learning ability. The present invention provides the use of compounds of formula I for the treatment of each of these conditions.

It is understood that compounds of the formulas Ia', Ib', Ic', and In';

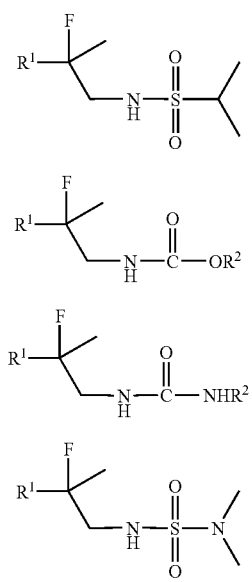

formula Ia' formula Ib' formula Ic' formula In' wherein R¹ represents an unsubstituted or substituted aromatic group, an unsubstituted or substituted heteroaromatic group, or an unsubstituted or substituted (5–8C)cycloalkyl group; or a pharmaceutically acceptable salt thereof; are included within the scope of formula I.

The present invention includes the pharmaceutically acceptable salts of the compounds defined by formula I. A compound of this invention can possess a sufficiently acidic group, a sufficiently basic group, or both functional groups, and accordingly react with any of a number of organic and inorganic bases, and inorganic and organic acids, to form a pharmaceutically acceptable salt. The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. Such salts include the pharmaceutically acceptable salts listed in *Journal of Pharmaceutical Science*, 66, 2–19 (1977) which are known to the skilled artisan. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, terephthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, 1-naphthalenesulfonate, 2-napthhalenesulfonate, 1,5-naphthalenedisulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as aryl, and includes phenyl and a polycyclic aromatic carbocyclic ring such as 1- or 2-naphthyl, 1,2-dihydronaphthyl, 1,2,3,4-tetrahydronaphthyl, and the like.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl, and quinolyl.

The term "substituted" as used in the term "substituted aromatic or heteroaromatic group" herein signifies that one or more (for example one or two) substituents may be present, said substituents being selected from atoms and groups which, when present in the compound of formula I, do not prevent the compound of formula I from functioning as a potentiator of glutamate receptor function.

It is understood that when $R^1$ represents an unsubstituted or substituted (5–8C)cycloalkyl group, mixtures of cis and trans isomers may result which can be separated into the individual cis and trans isomers by one of ordinary skill in the art, using standard techniques and procedures such as reverse phase or normal phase high performance liquid chromatography or flash chromatography, with a suitable stationary phase and a suitable eluent. Examples of suitable stationary phases are silica gel, alumina, and the like. Examples of suitable eluents are ethyl acetate/hexane, ethyl acetate/toluene, methanol/dichloromethane, and the like. Such individual cis and trans isomers are included within the scope of the present invention.

Examples of substituents which may be present in a substituted aromatic, heteroaromatic group or (5–8C)cycloalkyl group include halogen; nitro; cyano; hydroxyimino; (1–10C) alkyl; (2–10C)alkenyl; (2–10C)alkynyl; (3–8C) cycloalkyl; hydroxy(3–8C)cycloalkyl; oxo(3–8C)cycloalkyl; halo(1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C)alkoxycarbonyl dimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, $OCONR^{19}$ or $NR^{19}COO$, $R^{15}$ represents hydrogen, (1–10C)alkyl, phenyl(1–4C)alkyl, halo (1–10C)alkyl, (1–4C)alkoxycarbonyl(1–4C)alkyl, (1–4C) alkylsulfonylamino(1–4C)alkyl, N-(1–4C)alkoxycarbonyl) (1–4C)alkylsulfonylamino(1–4C)alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo (1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

The term (1–10C)alkyl includes (1–8C)alkyl, (1–6C)alkyl and (1–4C)alkyl. Particular values are methyl, ethyl, propyl, isopropyl, butyl, isobutyl, t-butyl, pentyl, hexyl, heptyl, octyl, nonyl and decyl.

The term (2–10C)alkenyl includes (3–10C)alkenyl, (2–8C)alkenyl, (2–6C)alkenyl and (2–4C)alkenyl. Particular values are vinyl and prop-2-enyl.

The term (2–10C)alkynyl includes (3–10C)alkynyl, (2–8C)alkynyl, (2–6C)alkynyl and (3–4C)alkynyl. A particular value is prop-2-ynyl.

The term C₁–C₆ alkoxy refers to a straight or branched alkyl chain having from one to six carbon atoms attached to an oxygen atom. Typical C₁–C₆ alkoxy groups include methoxy, ethoxy, propoxy, isopropoxy, butoxy, t-butoxy, pentoxy and the like. The term C₁–C₆ alkoxy includes within its definition the term C₁–C₄ alkoxy.

The term (3–8C)cycloalkyl, as such or in the term (3–8C) cycloalkyloxy, includes monocyclic and polycyclic groups. Particular values are cyclopropyl, cyclobutyl, cyclopentyl, cyclohexyl and bicyclo[2.2.2]octane. The term includes (3–6C)cycloalkyl: cyclopropyl, cyclobutyl, cyclopentyl and cyclohexyl.

As used herein the terms "integer of from 1 to 4" or "integer of from 1 to 3" includes the integers 1, 2, 3, and 4, or the integers 1, 2, and 3, respectively.

The term (5–8C)cycloalkyl includes cyclopentyl, cyclohexyl, cycloheptyl and cyclooctyl.

The term hydroxy(3–8C)cycloalkyl includes hydroxycyclopentyl, such as 3-hydroxycyclopentyl.

The term oxo(3–8C)cycloalkyl includes oxocyclopentyl, such as 3-oxocyclopentyl.

The terms "halogen", "Hal" or "halide" include fluorine, chlorine, bromine and iodine unless otherwise specified.

The term halo(1–10C)alkyl includes fluoro(1–10C)alkyl, such as trifluoromethyl and 2,2,2-trifluoroethyl, and chloro (1–10C)alkyl such as chloromethyl.

The term cyano(2–10C)alkenyl includes 2-cyanoethenyl.

The term (2–4C)alkylene includes ethylene, propylene and butylene. A preferred value is ethylene.

The term thienyl includes thien-2-yl and thien-3-yl.
The term furyl includes fur-2-yl and fur-3-yl.
The term oxazolyl includes oxazol-2-yl, oxazol-4-yl and oxazol-5-yl.
The term isoxazolyl includes isoxazol-3-yl, isoxazol-4-yl and isoxazol-5-yl.
The term oxadiazolyl includes [1,2,4]oxadiazol-3-yl and [1,2,4]oxadiazol-5-yl.
The term pyrazolyl includes pyrazol-3-yl, pyrazol-4-yl and pyrazol-5-yl.
The term thiazolyl includes thiazol-2-yl, thiazol-4-yl and thiazol-5-yl.
The term thiadiazolyl includes [1,2,4]thiadiazol-3-yl, and [1,2,4]thiadiazol-5-yl.
The term isothiazolyl includes isothiazol-3-yl, isothiazol-4-yl and isothiazol-5-yl.
The term imidazolyl includes imidazol-2-yl, imidazolyl-4-yl and imidazolyl-5-yl.
The term triazolyl includes [1,2,4]triazol-3-yl and [1,2,4]triazol-5-yl.
The term tetrazolyl includes tetrazol-5-yl.
The term pyridyl includes pyrid-2-yl, pyrid-3-yl and pyrid-4-yl.
The term pyridazinyl includes pyridazin-3-yl, pyridazin-4-yl, pyridazin-5-yl and pyridazin-6-yl.
The term pyrimidyl includes pyrimidin-2-yl, pyrimidin-4-yl, pyrimidin-5-yl and pyrimidin-6-yl.
The term benzofuryl includes benzofur-2-yl and benzofur-3-yl.
The term benzothienyl includes benzothien-2-yl and benzothien-3-yl.
The term benzimidazolyl includes benzimidazol-2-yl.
The term benzoxazolyl includes benzoxazol-2-yl.
The term benzothiazolyl includes benzothiazol-2-yl.
The term indolyl includes indol-2-yl and indol-3-yl.
The term quinolyl includes quinol-2-yl.

The term dihydrothiazolyl includes 4,5-dihydrothiazol-2-yl, and the term (1–4C)alkoxycarbonyldihydrothiazolyl includes 4-methoxycarbonyl-4,5-dihydrothiazol-2-yl.

The term —(1–4C)alkyl(3–8C)cycloalkyl includes the following:

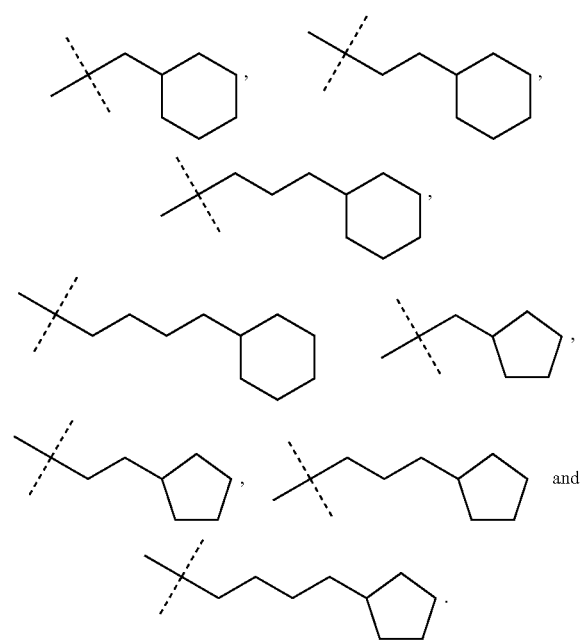

The term —(1–4C)alkylaromatic includes the following:

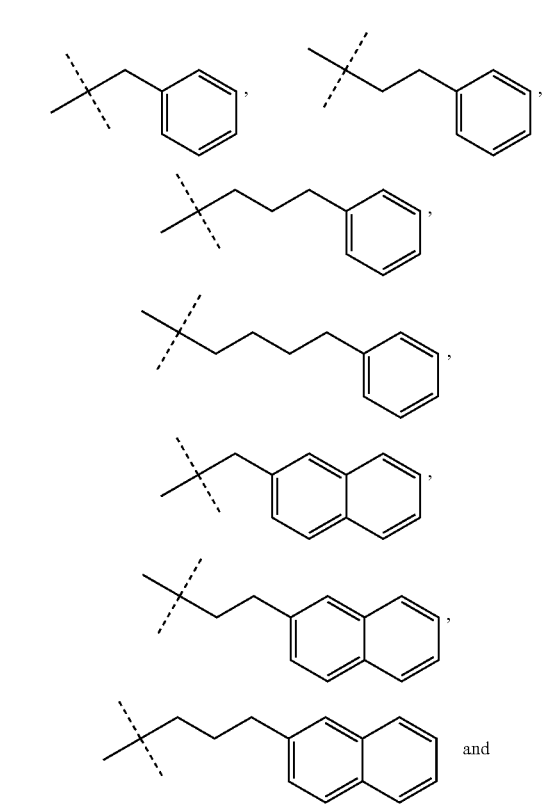

-continued

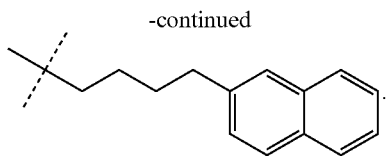

Preferably $R^a$ is methyl, ethyl, propyl, n-butyl, sec-butyl, pentyl, and hexyl with methyl being most preferred.

Preferably $R^b$ is hydrogen, methyl, ethyl, propyl, n-butyl, sec-butyl, pentyl, and hexyl, with hydrogen being most preferred.

Preferably $R^3$ and $R^4$ each represent methyl.

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2-enyl, methoxyethyl, phenyl, 4-fluorophenyl, or dimethylamino. Preferably $R^2$ is ethyl, 2-propyl or dimethylamino.

Examples of values for $R^9$ are hydrogen, methyl, ethyl, propyl, isopropyl, t-butyl, ethenyl, cyclopropyl, cyclobutyl, cyclopentyl, cyclohexyl, 2-pyrrolidinyl, morpholino or 2-tetrahydrofuryl.

$R^9$ is preferably (1–4C)alkyl, (2–4C)alkenyl, (3–6C)cycloalkyl, pyrrolidinyl, morpholino or tetrahydrofuryl.

Examples of values for $R^{15}$ are hydrogen, methyl, ethyl, propyl, isopropyl, butyl, t-butyl, benzyl, 2,2,2-trifluoroethyl, 2-methoxycarbonylethyl, cyclohexyl, 10-camphoryl, phenyl, 2-fluorophenyl, 3-fluorophenyl, 2-trifluoromethylphenyl, 4-trifluoromethylphenyl, 2-methoxyphenyl, 3-methoxyphenyl, 4-methoxyphenyl, 1-(5-dimethylamino)naphthyl, and 2-thienyl.

$X^1$ preferably represents O, CO, CONH or NHCO.

z is preferably 0.

Particular values for the groups $(CH_2)_y X^1 R^9$ and $(CH_2)_z X^3 R^{15}$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C)alkenyloxy, such as prop-2-enyloxy; (3–10C)alkynyloxy, including (3–6C)alkynyloxy, such as prop-2-ynyloxy; and (1–6C)alkanoyl, such as formyl and ethanoyl.

Examples of particular values for y are 0 and 1.

Examples of particular values for z are 0, 1, 2 and 3.

$L^a$ and $L^b$ preferably each independently represents $CH_2$.

$X^2$ preferably represents a bond, O, NH, CO, CH(OH), CONH, NHCONH or $OCH_2CONH$, with a bond, O, and CONH being especially preferred.

Preferably the group $(CH_2)_y X^1 R^9$ represents CHO; $COCH_3$, $OCH_3$; $OCH(CH_3)_2$; $NHCOR^9$ in which $R^9$ represents methyl, ethyl, isopropyl, t-butyl, ethenyl, cyclopropyl, cyclobutyl, cyclopentyl, cyclohexyl, 2-pyrolidinyl or morpholino; $CONHR^9$ in which $R^9$ represents cyclopropyl or cyclopentyl; $NHCOCOOCH3$; or 2-tetrahydrofurylmethoxy.

Preferably the group $(CH_2)_z X^3 R^{15}$ represents $NH_2$; $CH_2NH_2$; $(CH_2)_2NH_2$; $(CH_2)_3NH_2$; $CONH_2$; $CONHCH_3$; $CON(CH_3)_2$; $N(C_2H_5)_2$; $CH_2OH$; $CH(OH)CH_3$; $CH(OH)CH_2CH_3$; CHO; $COCH_3$; COOH; $COOCH_3$; $CH_2NHCOOC(CH_3)_3$; $(CH_2)_2NHCOOC(CH_3)_3$; $SO_2NH_2$; $NHSO_2CH_3$; $NHSO_2CH(CH_3)_2$; a group of formula $(CH_2)_2NHSO_2R^{15}$ in which $R^{15}$ represents $CH_3$, $CH_2CH_3$, $CH(CH_3)_2$, $(CH_2)_2CH_3$, $(CH_3)_3CH_3$, benzyl, $CH_2CF_3$, 2-methoxycarbonylethyl, cyclohexyl, 10-camphoryl, phenyl, 2-fluorophenyl, 4-fluorophenyl, 2-trifluoromethylphenyl, 4-trifluoromethylphenyl, 4-methoxyphenyl, 1-(2-dimethylamino)naphthyl or 2-thienyl; $CH(OH)CH_2NHSO_2CH_3$; $(CH_2)_3NHSO_2CH(CH_3)_2$; $COCH_2N(OCOC(CH_3)_2SO_2CH_3$; $COCH_2NHSO_2CH_3$; $(CH_2)_2NHCOR^{15}$ in which $R^{15}$ represents $CH_3$, $CH(CH_3)_2$, $CH_2CH(CH_3)_2$, phenyl, 3-fluorophenyl, 4-fluorophenyl, benzyl, 2-methoxyphenyl, 4-methoxyphenyl, 2-thienyl, CH=CH, CH=CHCN, $OCH_3$ or $O(CH_2)_3CH_3$.

Examples of particular values for $(L^a)_n—X^2—(L^b)_m$ are a bond, O, NH, S, SO, $SO_2$, CO, $CH_2$, $COCH_2$, COCONH, $CH(OH)CH_2$, CONH, NHCO, NHCONH, $CH_2O$, $OCH_2$, $OCH_2CONH$, $CH_2NH$, $NHCH_2$ and $CH_2CH_2$, with a bond, CONH, and $CH_2O$ being especially preferred.

$R^{14}$ is preferably an unsubstituted or substituted phenyl, naphthyl, furyl, thienyl, isoxazolyl, thiazolyl, tetrazolyl, pyridyl, pyrimidyl benzothienyl or benzothiazolyl group.

Examples of particular values for $R^{14}$ are phenyl, 2-fluorophenyl, 3-fluorophenyl, 4-fluorophenyl, 2-chloro-phenyl, 3-chlorophenyl, 4-chlorophenyl, 2-bromophenyl, 3-bromophenyl, 4-bromophenyl, 4-iodophenyl, 2,3-difluoro-phenyl, 2,4-difluorophenyl, 3,5-difluorophenyl, 3,4-dichlorophenyl, 3,5-dichlorophenyl, 4-cyanophenyl, 3-nitrophenyl, 4-hydroxyiminophenyl, 2-methylphenyl, 4-methylphenyl, 4-ethylphenyl, 3-propylphenyl, 4-t-butylphenyl, 2-prop-2-enylphenyl, 4-(4-(1,1-dioxotetrahydro-1,2-thiazinyl)phenyl, 2-trifluoromethylphenyl, 3-trifluoromethylphenyl, 4-trifluoromethylphenyl, 2-bromomethylphenyl, 2-fluoro-4-trifluoromethylphenyl, 4-(2-cyanoethenyl)phenyl, 4-phenyl, 2-formylphenyl, 3-formylphenyl, 4-formylphenyl, 2-acetylphenyl, 3-acetylphenyl, 4-acetylphenyl, 2-propanoylphenyl, 2-(2-methyl-propanoyl)phenyl, 2-methoxyphenyl, 3-methoxyphenyl, 4-methoxyphenyl, 4-butoxyphenyl, 2-hydroxymethylphenyl, 4-hydroxymethylphenyl, 2-(1-hydroxyethyl)phenyl, 3-(1-hydroxyethyl)phenyl, 4-(1-hydroxyethyl)phenyl, 2-(1-hydroxypropyl)phenyl, 4-(1-hydroxypropyl)phenyl, 2-(1-hydroxy-2,2-dimethyl-propyl)phenyl, 4-trifluoromethoxyphenyl, 2-aminophenyl,4-aminophenyl, 4-N,N-diethylaminophenyl, 4-aminomethylphenyl, 4-(2-aminoethyl)phenyl, 4-(3-aminopropyl)phenyl, 4-carboxyphenyl, 4-carbamoylphenyl, 4-N-methylcarbamoylphenyl, 4-N,N-dimethylcarbamoylphenyl, 2-isopropylaminomethylphenyl, 4-t-butoxycarbonylaminomethylphenyl, 4-(2-isopropoxy-carboxamido)ethylphenyl, 4-(2-t-butoxycarboxamido)ethyl-phenyl, 4-isopropylsulfonylaminophenyl, 4-(2-methane-sulfonylamino)ethylphenyl, 4-(2-ethylsulfonylamino)ethyl-phenyl, 4-(3-isopropylsulfonylamino)propylphenyl, 4-(1-(2-(2-propane)sulfonylamino)propyl)phenyl, 4-(2-propylsulfonylamino)ethylphenyl, 4-(2-isopropylsulfonylamino)ethylphenyl, 4-(2-butylsulfonylamino)ethylphenyl, 4-(1-isopropyl-sulfonylaminomethyl)ethylphenyl, 4-(1-hydroxy-2-methane-sulfonylamino)ethylphenyl, 4-(2-(2,2,2-trifluoroethyl)sulfonylaminoethyl)phenyl, 4-(2-cyclohexylsulfonylamino)-ethylphenyl, 4-(2-(2,2,2-trifluoroethyl)sulfonylamino)-ethylphenyl, 4-(2-N,N-dimethylaminosulfonylamino)-ethylphenyl, 4-(2-phenylsulfonylaminoethyl)phenyl, 4-(2-(2-fluorophenyl)sulfonylaminoethyl)phenyl, 4-(2-(4-fluorophenyl)sulfonylaminoethyl)phenyl, 4-(2-(2-trifluoromethylphenyl)sulfonylaminoethyl)phenyl, 4-(2-(4-trifluoromethylphenyl)sulfonylaminoethyl)phenyl, 4-(2-(4-methoxyphenyl)sulfonylaminoethyl)phenyl, 4-(2-(1-(5-dimethylamino)napthalenesulfonylamino)ethyl)phenyl, 4-(2-(2-thienyl)sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonyl-amino)ethyl)phenyl, 4-(2-phenylacetamido)ethyl)phenyl, 4-methanesulfonylaminoethanoylphenyl, 4-(N-(t-butoxy-carbonyl)methanesulfonylaminoethanoyl)phenyl, 4-(2-(2-thienylcarboxamido)ethyl)phenyl, thien-2-yl, 5-hydroxy-methylthien-2-yl, 5-formylthien-2-yl, thien-3-yl, 5-hydroxymethylthien-3-yl, 5-formylthien-3-yl, 2-bromothien-3-yl, fur-2-yl, 5-nitrofur-2-yl, fur-3-yl, isoxazol-5-yl, 3-bromoisoxazol-5-yl, isoxazol-3-yl, 5-trimethylsilylisoxazol-3-yl, 5-methylisoxazol-3-yl, 5-hydroxymethylisoxazol-3-yl, 5-methyl-3-phenylisoxazol-4-yl, 5-(2-hydroxyethyl)isoxazol-3-yl, 5-acetylisoxazol-3-yl, 5-carboxyisoxazol-3-yl, 5-N-methylcarbamoylisoxazol-3-yl, 5-methoxycarbonylisoxazol-3-yl, 3-bromo[1,2,4]oxadiazol-5-yl, pyrazol-1-yl, thiazol-2-yl, 4-hydroxymethylthiazol-2-yl, 4-methoxycarbonylthiazol-2-yl, 4-carboxythiazol-2-yl, imidazol-1-yl, 2-sulfhydrylimidazol-1-yl, [1,2,4]triazol-1-yl, tetrazol-5-yl, 2-methyltetrazol-5-yl, 2-ethyltetrazol-5-yl, 2-isopropyl-tetrazol-5-yl, 2-(2-propenyl)tetrazol-5-yl, 2-benzyl-tetrazol-5-yl, pyrid-2-yl, 5-ethoxycarbonylpyrid-2-yl, pyrid-3-yl, 6-chloropyrid-3-yl, pyrid-4-yl, 5-trifluoro-methylpyrid-2-yl, 6-chloropyridazin-3-yl, 6-methylpyridazin-3-yl, 6-methoxypyrazin-3-yl, pyrimidin-5-yl, benzothien-2-yl, benzothiazol-2-yl, and quinol-2-yl.

Examples of an unsubstituted or substituted aromatic or heteroaromatic group represented by $R^1$ are unsubstituted or substituted phenyl, furyl, thienyl (such as 3-thienyl) and pyridyl (such as 3-pyridyl).

Examples of an unsubstituted or substituted (5–8C)cycloalkyl group represented by $R^1$ are unsubstituted or substituted cyclopentyl, cyclohexyl, cycloheptyl and cyclooctyl, with cyclohexyl being preferred.

More preferably, $R^1$ represents 2-naphthyl or a group of formula

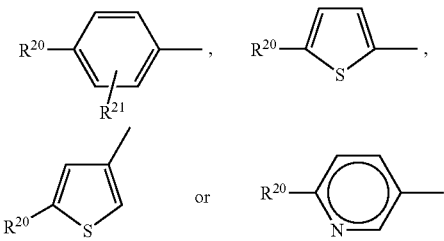

in which
$R^{20}$ represents halogen; nitro; cyano; hydroxyimino; (1–10C)alkyl; (2–10C)alkenyl; (2–10C)alkynyl; (3–8C)cyclo-alkyl; hydroxy(3–8C)cycloalkyl; oxo (3–8C)cycloalkyl; halo(1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; tetrazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyldihydrothiazolyl; (1–4C)alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; benzothiazolyl; and a group of formula $R^{14}-(L^a)_n-X^2-(L^b)_m$ in which $X^2$ represents a bond, O, NH, S, SO, $SO_2$, CO, CH(OH), CONH, NHCONH, NHCOO, COCONH, $OCH_2CONH$ or CH=CH, NHCO, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C) alkyl; cyano(2–10C)alkenyl; phenyl; $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl) (1–4C)alkylsulfonylamino(1–4C)alkyl, (3–10C)alkenyl, (3–10C)alkynyl, (3–8C)cycloalkyl, camphoryl or an aromatic or heteroaromatic group which is unsubstituted or substituted by one or two of halogen, (1–4C) alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and
$R^{21}$ represents a hydrogen atom, a halogen atom, a (1–4C) alkyl group or a (1–4C)alkoxy group.

Examples of particular values for $R^{20}$ are fluorine, chlorine, bromine, cyano, hydroxyimino, methyl, ethyl, propyl, 2-propyl, butyl, 2-methylpropyl, 1,1-dimethylethyl, cyclopentyl, cyclohexyl, 3-hydroxycyclopentyl, 3-oxocyclopentyl, methoxy, ethoxy, propoxy, 2-propoxy, acetyl, acetylamino, ethylcarboxamido, propylcarboxamido, 1-butanoylamido, t-butylcarboxamido, acryloylamido, 2-pyrrolidinylcarboxamido, 2-tetrahydrofurylmethoxy, morpholinocarboxamido, methyloxalylamino, cyclo-propylcarboxamido, cyclobutylcarboxamido, cyclopentyl-carboxamido, cyclohexylcarboxamido, cyclopropylcarbamoyl, cyclopentylcarbamoyl, pyrrolidin-1-yl, morpholino, piperidin-1-yl, N-methylpiperazinyl, N-benzylpiperazinyl, 2-thienyl, 3-thienyl, 2-furyl, 3-furyl, isoxazol-3-yl, thiazol-2-yl, tetrazol-5-yl, pyrid-2-yl, pyrid-3-yl, pyrid-4-yl, pyrimidin-5-yl, 4,5-dihydrothiazol-2-yl, 4,5-dihydro-4-methoxycarbonylthiazol-2-yl, 4,5-dihydro-4-methoxy-carbonyl-5,5-dimethylthiazol-2-yl, benzothien-2-yl, benzothiazol-2-yl, phenyl, 2-fluorophenyl, 3-fluorophenyl, 2,3-difluorophenyl, 4-chlorophenyl, 3,4-dichlorophenyl, 3,5-dichlorophenyl, 3-nitrophenyl, 4-cyanophenyl, 2-methylphenyl, 4-methylphenyl, 4-(4-(1,1-dioxotetrahydro-1,2-thiazinyl)phenyl, 3-trifluoromethylphenyl, 4-trifluoro-methylphenyl, 4-(2-cyanoethenyl)phenyl, 2-formylphenyl, 3-formylphenyl, 4-formylphenyl, 3-acetylphenyl, 4-acetylphenyl, 4-carboxphenyl, 2-methoxyphenyl, 4-methoxyphenyl, 2-hydroxymethylphenyl, 4-hydroxymethylphenyl, 3-(1-hydroxyethyl) phenyl, 4-(1-hydroxyethyl)phenyl, 4-(1-hydroxypropyl) phenyl, 2-aminophenyl, 4-aminophenyl, 4-N,N-diethylaminophenyl, 4-aminomethylphenyl, 4-(2-aminoethyl)-phenyl, 4-(3-aminopropyl)phenyl, 4-(2-acetylaminoethyl)-phenyl, 4-t-butoxycarboxylaminoethyl) phenyl, 4-(2-t-butoxycarboxylaminoethyl)phenyl, benzylsulfonylamino, 4-isopropylsulfonylaminophenyl, 4-(2-methanesulfonylaminoethyl)phenyl, 4-(2-ethylsulfonylaminoethyl)phenyl, 4-(2-propylsulfonylaminoethyl)phenyl, 4-(2-butylsulfonyl-aminoethyl)phenyl, 4-(2-isopropylsulfonylaminoethyl)phenyl, 4-(1-hydroxy-2-methanesulfonylaminoethyl)phenyl, 4-(2-dimethylaminosulfonylaminoethyl)phenyl, 4-(1-(2-(2-propyl)sulfonylaminopropyl)phenyl, 4-(2-(2,2,2-trifluoroethyl)sulfonylaminoethyl)phenyl, 4-(2-cyclohexylsulfonyl-aminoethyl)phenyl, 4-(2-phenylsulfonylaminoethyl)phenyl, 4-(2-(2-fluorophenyl)sulfonylaminoethyl)phenyl, 4-(2-(4-fluorophenyl)sulfonylaminoethyl) phenyl, 4-(2-(2-trifluoromethylphenyl)sulfonylaminoethyl) phenyl, 4-(2-(4-trifluoromethylphenyl)sulfonylaminoethyl) phenyl, 4-(2-(4-methoxyphenyl)sulfonylaminoethyl)phenyl, 4-(2-(1-(5-dimethylamino)napthalenesulfonylamino)ethyl) phenyl, 4-(2-(2-thienyl)sulfonylamino)ethyl)phenyl, 4-(2-benzamidoethyl)-phenyl, 4-(2-(4-fluorobenzamido)ethyl) phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(2-(2-thienylcarboxamido)ethyl)phenyl, 4-carbamoylphenyl, 4-methylcarbamoylphenyl, 4-dimethylcarbamoylphenyl, 4-(2-(2-methylpropaneamido)ethyl)phenyl, 4-(2-(3-methylbutaneamido)ethyl)phenyl, benzoylmethyl, benzamido, 2-fluorobenzamido, 3-fluorobenzamido, 4-fluorobenzamido, 2,4-difluorobenzamido, 3-chlorobenzamido, 4-chlorobenzamido, 4-bromobenzamido, 4-iodobenzamido, 4-cyanobenzamido, 3-methylbenzamido, 4-methylbenzamido, 4-ethylbenzamido, 4-propylbenzamido, 4-t-butylbenzamido, 4-vinylbenzamido, 2-trifluoromethylbenzamido, 3-trifluoromethylbenzamido, 4-trifluoromethylbenzamido, 2-fluoro-4-trifluoromethylbenzamido, 2-methoxybenzamido, 3-methoxybenzamido, 4-methoxybenzamido, 4-butoxybenzamido, 4-phenylphenyl-carboxamido, 4-benzylcarboxamido, 4-phenoxymethyl-carboxamido, 2-fluorobenzylamino, benzyloxy, 2-fluorobenzyloxy, 2-hydroxy-2-phenylethyl, 2-fluorophenylcarbamoyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonylamino)ethyl)phenyl, 4-(2-phenylacetamido)-ethyl)phenyl, 4-(methanesulfonylaminoethanoyl)phenyl, 4-(N-t-butoxycarbonyl)methanesulfonylaminoethanoyl)phenyl, 2-thienylcarboxamido, 2-furylcarboxamido, 3-(5-methyl-isoxazolyl)carboxamido, 5-isoxazolylcarboxamido, 2-benzothienylcarboxamido, 4-(5-methyl-3-phenylisoxazolyl)-carboxamido, 4-pyridylcarboxamido, 2-(5-nitrofuryl)carboxamido, 2-pyridylcarboxamido, 6-chloro-2-pyridyl-carboxamido, 2-thienylsulfonamido, 2-thienylmethylamino, 3-thienylmethylamino, 2-furylmethylamino, 3-furylmethylamino, 3-acetylureido and 2-(2-thienyl)ethylureido.

Examples of particular values for $R^{21}$ are hydrogen and chlorine. $R^{21}$ is preferably ortho to $R^{20}$.

Examples of particular values for $R^1$ are 2-naphthyl, 4-bromophenyl, 4-cyanophenyl, 4-benzamidophenyl, 4-methylphenyl, 4-isopropyl-phenyl, 4-isobutylphenyl, 4-t-butylphenyl, 4-methoxyphenyl, 4-isopropoxyphenyl, 4-cyclopentylphenyl, 4-cyclohexylphenyl, 4-(2-hydroxymethylphenyl)phenyl, 4-(4-hydroxymethylphenyl)-phenyl, 4-(2-furyl)phenyl, 4-(3-furyl)phenyl, 4-(2-thienyl) phenyl, 4-(3-thienyl)phenyl, 4-(pyrrolidin-1-yl)phenyl, 4-(piperidin-1-yl)phenyl, 3-chloro-4-piperidin-1-ylphenyl, 4-benzyloxyphenyl, 4-(2-fluorophenyl)phenyl, 4-(3-fluorophenyl)phenyl, 4-(2-formylphenyl)phenyl, 4-(3-formylphenyl)-phenyl, 4-(4-formylphenyl)phenyl, 4-(4-methylphenyl) phenyl, and 4-(2-methoxyphenyl)phenyl.

The compounds of formula I can be prepared following the various procedures set forth below. The reagents and starting materials are readily available to one of ordinary skill in the art. All substituents, unless otherwise specified are as previously defined.

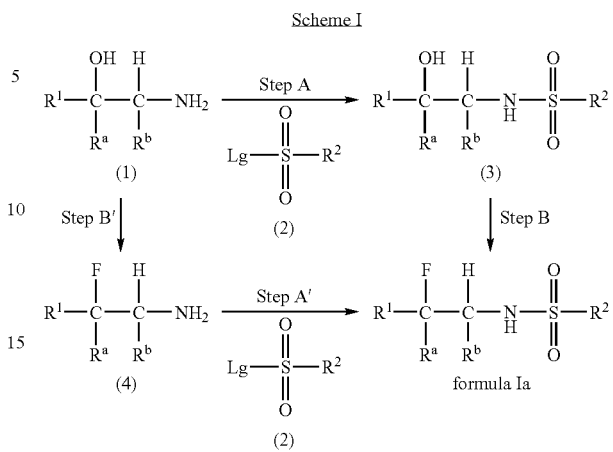

Scheme I

In Scheme I, step A the compound of structure (1) is combined with the compound of structure (2) under conditions well known in the art to provide the compound of structure (3). More specifically, for example, the compound (1) is dissolved in a suitable organic solvent. Examples of suitable organic solvents include methylene chloride, tetrahydrofuran, and the like. The solution is treated with a slight excess of a suitable base, and then cooled to about −78° C. to about 0° C. Examples of suitable bases include triethylamine, pyridine, 1,8-diazabicyclo[5.4.0]undec-7-ene (DBU), and the like. To the stirring solution is added one equivalent of compound (2). The term "Lg" as used herein refers to a suitable leaving group. Examples of suitable leaving groups include, Cl, Br, methanesulfonyloxy, trifluoromethanesulfonyloxy, benzenesulfonyloxy, p-toluenesulfonyloxy, and the like. Cl is the preferred leaving group. The reaction mixture is stirred at about 0° C. to about 50° C. for about 0.5 hours to about 16 hours. The compound (3) is then isolated and purified by techniques well known in the art, such as extraction techniques and chromatography. For example, the mixture is washed with 10% sodium bisulfate, the layers separated and the aqueous extracted with several times with a suitable organic solvent, such as methylene chloride. The organic extracts are combined, dried over anhydrous sodium sulfate, filtered and concentrated under vacuum. The residue is then purified by flash chromatography on silica gel with a suitable eluent such as ethyl acetate/hexane to provide the compound (3).

In Scheme I, step B the compound of structure (3) is fluorinated under conditions well known in the art to provide the compound of formula Ia. For example, compound (3) is dissolved in a suitable organic solvent, such as methylene chloride and the solution is cooled to about −78° C. under an inert atmosphere, such as nitrogen. To this solution is added slowly, about one equivalent of diethylaminosulfur trifluoride (DAST) dissolved in a suitable organic solvent, such as methylene chloride with stirring. The reaction is then allowed to warm to room temperature (about 22° C.) and the compound of formula Ia is then isolated and purified using techniques and procedures well known in the art, such as extraction techniques and chromatography. For example, the reaction is diluted with water and methylene chloride. The layers are separated and the organic layer is washed with water, dried over anhydrous sodium sulfate, filtered and concentrated under vacuum to provide the crude compound of formula Ia. This crude material can then be purified by standard techniques, such as recrystallization from a suitable eluent, or flash chromatography or radial chromatography (radial chromatography is carried out using a Chromatotron, Harrison Research Inc., 840 Moana Court, Palo Alto, Calif. 94306) on silica gel, with a suitable eluent, such as hexane/ethyl acetate to provide purified compound of formula Ia.

Alternatively, in Scheme I, step B' the compound (1) is fluorinated in a manner analogous to the procedure described in step B above with DAST to provide the compound of structure (4). In Scheme I, step A' compound (4) converted to the compound of formula Ia in a manner analogous to the procedure described in step A above.

Scheme II

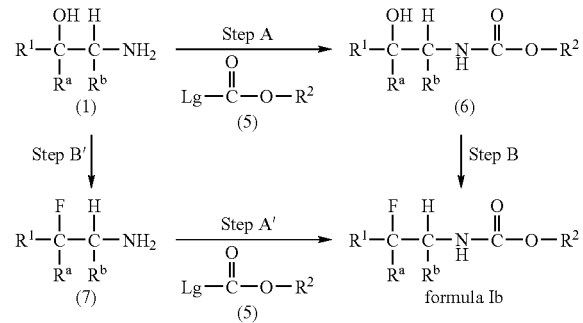

In Scheme II, step A compound (1) is converted to the carbamate (6) under standard carbamate forming conditions well known to one of ordinary skill in the art. For examples of standard carbamate forming conditions see J. March, "Advanced Organic Chemistry: Reactions, Mechanisms, and Structure," $2^{nd}$ Edition, McGraw Hill Inc., (1977) pages 382–383, and T. W Green, "Protective Groups in Organic Synthesis," John Wiley & Sons, Inc. (1981) pages 223–248.

More specifically, for example, compound (1) is dissolved in a suitable organic solvent, such as tetrahydrofuran or methylene chloride and treated with an equivalent of a compound (5) wherein "Lg" represents a suitable leaving group. Examples of suitable leaving groups are Cl, Br, I, and the like. The reaction can be performed at a temperature of from about –10° C. to about 50° C., preferably at a temperature of about 0° C. to about 25° C. After about 2 hours to about 12 hours, the carbamate (6) is isolated and purified by techniques well known in the art, such as extraction techniques and chromatography. For example, the reaction is diluted with a suitable organic solvent, such as methylene chloride, rinsed with saturated sodium bicarbonate, brine, dried over anhydrous magnesium sulfate, filtered and concentrated under vacuum. The crude product can then be purified by flash chromatography on silica gel with a suitable eluent, such ethyl acetate/hexanes to provide the purified carbamate (6).

In Scheme II, step B carbamate (6) is converted to the compound of formula Ib in a manner analogous to the procedure set forth in Scheme I, step B.

Alternatively, in Scheme II, step B' the compound (1) is fluorinated in a manner analogous to the procedure described in step B above with DAST to provide the compound of structure (7). In Scheme II, step A' compound (7) is converted to the compound of formula Ib in a manner analogous to the procedure described in step A above.

Scheme III

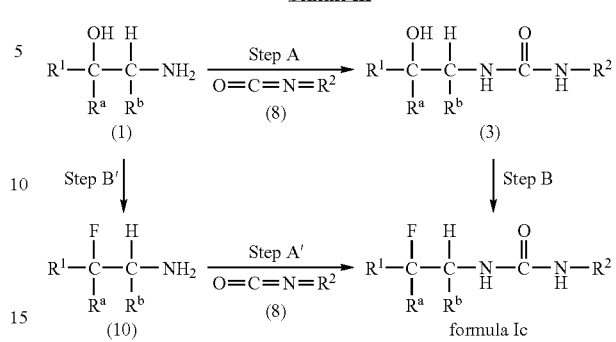

In Scheme III, step A urea (9) is prepared from compound (1) under standard urea forming conditions well known to one of ordinary skill in the art. For examples of standard urea forming conditions see J. March, "Advanced Organic Chemistry: Reactions, Mechanisms, and Structure," $2^{nd}$ Edition, McGraw Hill Inc., (1977) page 823, and T. W Green, "Protective Groups in Organic Synthesis," John Wiley & Sons, Inc. (1981) pages 248–49.

More specifically, for example, a compound (1) is dissolved in a suitable organic solvent, such as methylene chloride, and the solution is treated with about 1.1 equivalents of an isocyanate (8). The reaction can be performed at a temperature of about –10° C. to about 50° C. for about 2 hours to about 12 hours to provide the urea (9). The urea (9) can be isolated and purified by techniques well known in the art, such as extraction techniques and chromatography. For example, the reaction is diluted with a suitable organic solvent, such as methylene chloride, rinsed with water, brine, dried over anhydrous sodium sulfate, filtered and concentrated under vacuum. The crude product can then be purified by flash chromatography on silica gel with a suitable eluent, such ethyl acetate/hexanes to provide the purified urea (9).

In Scheme III, step B urea (9) is converted to the compound of formula Ic in a manner analogous to the procedure set forth in Scheme I, step B.

Alternatively, in Scheme III, step B' the compound (1) is fluorinated in a manner analogous to the procedure described in step B above with DAST to provide the compound of structure (10). In Scheme III, step A' compound (10) is converted to the compound of formula Ic in a manner analogous to the procedure described in step A above.

The compounds of formula I in which $R^1$ represents a 4-bromophenyl group, a 4-iodophenyl group or a 4-(triflate) phenyl group may conveniently be converted into other compounds of formula I in which R represents another 4-substituted phenyl group under conditions well known in the art, such as by reaction with an appropriate boronic acid derivative, for example, a benzeneboronic acid derivative. See for example, International Publication Number WO 98/33496, published Aug. 6, 1998, the disclosure of which is hereby incorporated by reference. More specifically, the reaction is conveniently performed in the presence of a tetrakis (triarylphosphine)palladium(0) catalyst, such as tetrakis (triphenylphosphine)palladium(0) and a base such as potassium carbonate. Convenient solvents for the reaction include aromatic hydrocarbons, such as toluene. The temperature at which the reaction is conducted is conveniently in the range of from 0 to 150° C., preferably 75 to 120° C. Bis aromatic intermediates useful in the preparation of compounds of formula I may be prepared by reacting a bromoaromatic or bromoheteroaromatic compound with an aromatic or heteroaromatic boronic acid in an analogous manner.

Alternatively, the coupling reaction may be carried out using palladium diacetate with a suitable organic solvent, such as n-propanol or acetone. See for example, *Organic Synthesis* 1998, 75, 61; Goodson, F. E.; Wallow, T. I.; Novak, B. M. and *Organic Synthesis* 1998, 75, 53; Huff, B. E.; Koenig, T. M.; Mitchell, D.; Staszak, M. A. wherein analogous coupling conditions are employed.

The boronic acid derivative used as a starting material may be prepared by reacting a trialkyl borate, such as triisopropyl borate with an appropriate organolithium compound at reduced temperature. For example, 2-fluorobenzeneboronic acid may be prepared by reacting 2-fluorobromobenzene with butyllithium in tetrahydrofuran at about −78° C. to afford 2-fluorophenyl lithium, and then reacting this organolithium compound with triisopropyl borate. This is followed by hydrolysis with aqueous HCl.

Alternatively, the compounds of formula I in which $R^1$ represents a 4-bromophenyl group may be converted to a 4-(trimethylstannyl)phenyl or 4-(tri-n-butylstannyl)phenyl group by treatment of the corresponding bromide with a palladium(0) catalyst, such as tetrakis(triphenylphosphine)-palladium(0) and hexaalkyldistannane, where the alkyl group is methyl or n-butyl, in an aprotic solvent such as toluene in the presence of a tertiary amine base such as triethylamine, at temperatures ranging from 80 to 140° C., preferably from 90 to 110° C.

The compounds of formula I in which $R^1$ represents a 4-(tri-n-butylstannyl)phenyl group may then be reacted with an aryl- or heteroarylbromide, such as 2-bromothiophene-5-carboxaldehyde, or an aryl- or heteroaryliodide, or an aryl- or heteroaryltriflate, in the presence of a palladium(0) catalyst, such as tetrakis(triphenylphosphine)palladium(0), or a palladium(II) catalyst, such as bis(triphenylphosphine)-palladium(II) dichloride, in an aprotic solvent, such as dioxane, at temperatures ranging from 80 to 140° C., preferably from 90 to 110° C., to afford the corresponding 4-(aryl)phenyl or 4-(heteroaryl)phenyl substituted compound.

The compounds of formula I in which $R^1$ represents a 4-bromophenyl group may be converted into other compounds of formula I in which $R^1$ represents a 4-substituted alkyl- or cycloalkylphenyl group, such as 4-cyclopentylphenyl by treatment of the corresponding bromide with an appropriate alkyl- or cycloalkyl Grignard reagent, such as cyclopentyl-magnesium bromide, in the presence of a palladium(II) catalyst, such as [1,1'-bis(diphenylphosphino)ferrocene]-dichloropalladium(II)(PdCl$_2$(dppf)), in an aprotic solvent, such as diethyl ether at temperatures ranging from −78° C. to 25° C.

The compounds of formula I in which $R^1$ represents a 4-bromophenyl group may be converted into a 4-substituted carboxyaldehydephenyl(formylphenyl) group by reaction of the corresponding bromide with the carbon monoxide gas which is bubbled into the reaction under atmospheric pressure in the presence of a palladium(II) catalyst, such as bis(triphenyl-phosphine)palladium(II) dichloride and sodium formate in an aprotic solvent, such as dimethylformamide at temperatures ranging from 70 to 110° C., preferably at 90° C.

The compounds of formula I in which $R^1$ represents a 4-hydroxyphenyl group may be converted into other compounds of formula I in which $R^1$ represents an alkoxy group by treatment of the corresponding hydroxyphenyl group with an appropriate alkylhalide such as benzylbromide in the presence of sodium hydride in an aprotic solvent such as dimethylformamide at temperatures ranging from 25 to 100° C., preferably from 50 to 90° C.

The compounds of structure (1a) can be prepared following the procedure described in Scheme IV. The reagents and starting materials are readily available to one of ordinary skill in the art. All substituents, unless otherwise specified are as previously defined.

Scheme IV

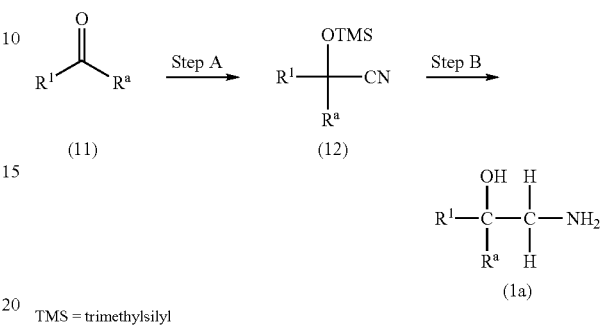

TMS = trimethylsilyl

In Scheme IV, step A the compound of structure (11) is converted to the compound of structure (12) under standard conditions. For example, see Greenlee and Hangauer, *Tetrahedron Lett.*, 24(42), 4559 (1983). For example, compound (11) is dissolved in a suitable organic solvent, such as dry tetrahydrofuran, containing excess 18-crown-6, and excess potassium cyanide. To this mixture at room temperature is added dropwise about 1.2 equivalents of cyanotrimethylsilane. The reaction mixture is allowed to stir for about 1 to 4 hours to provide compound (12). Compound (12) is then carried on directly to step B without isolation.

Alternatively, in Scheme IV, step A, for example, compound (11) is combined with a catalytic amount of zinc iodide followed by slow addition of excess trimethylsilyl cyanide with the generation of heat. The resulting solution is stirred at room temperature under nitrogen for about 8 to 16 hours. The mixture is then diluted with a suitable organic solvent, such as chloroform, washed with saturated sodium bicarbonate, water, brine, dried over anhydrous magnesium sulfate, filtered, and concentrated under vacuum to provide compound (12).

In Scheme IV, step B compound (12) is converted to compound of structure (1a). For example, compound (11) prepared above, still in solution, is treated with a solution of about 1.4 equivalents of borane in dimethylsulfide. The reaction mixture is then heated to reflux for about 16 hours and then cooled to room temperature. The reaction mixture is then cautiously treated with anhydrous HCl in methanol and allowed to stir for about one hour. The product (1a) is then isolated and purified using standard techniques and procedures. For example, the solvent is removed under vacuum and the residue triturated with a suitable organic solvent, such at methy t-butyl ether and the solid is collected by filtration. The solid is then suspended in methylene chloride/tetrahydrofuran mixture (1:2.4) and treated with 1N NaOH until about pH 12.3 is reached. The phases are separated and the organic phase is rinsed with brine. The organic phase is then concentrated under vacuum and the residue triturated with diethyl ether to provide the purified compound (1a). Compound (1a) is then used in Schemes I, II and III in a manner analogous to the procedures described for compound (1).

More specifically, compounds of structure (1a') can be prepared as disclosed in Scheme V. The reagents and starting materials are readily available to one of ordinary skill in the art. All substituents, unless otherwise specified are as previously defined.

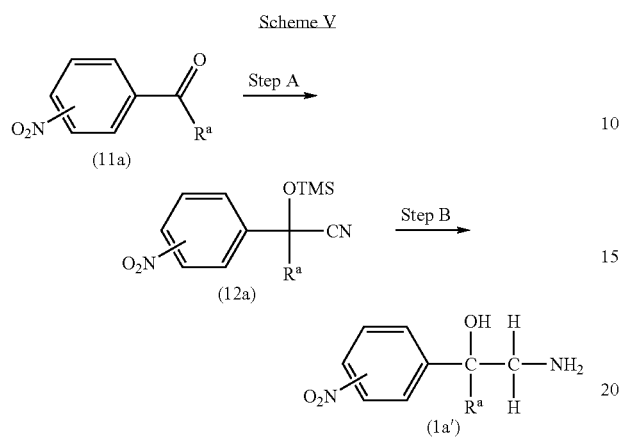

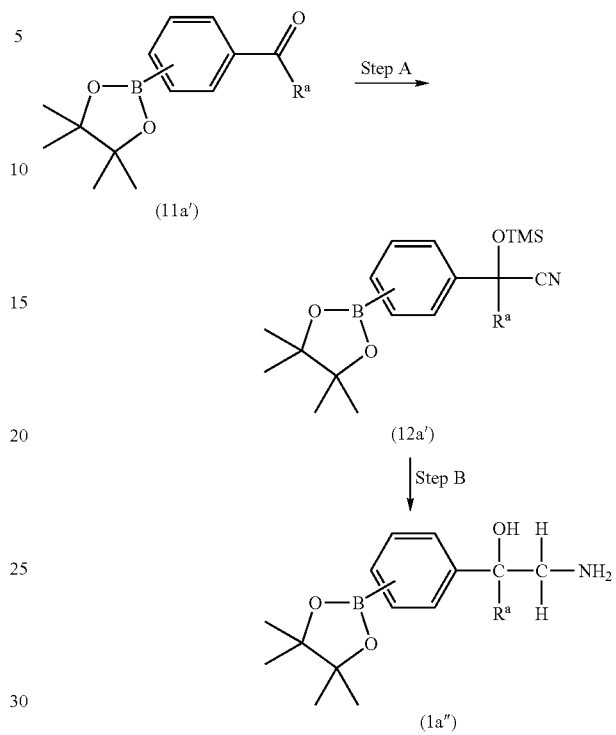

In Scheme V, step A, the compound of structure (11a) is converted to the compound of structure (12a) in a manner analogous to the procedure described in Scheme IV, step A.

In Scheme V, step B, the compound of structure (12a) is converted to the compound of structure (1a') in a manner analogous to the procedure described in Scheme IV, step B. Compound (1a') can then be converted to a sulfonamide, carbamate or urea in a manner analogous to the procedures described in Schemes I, II and III above. The resulting sulfonamide, carbamate, or urea can then be fluorinated with DAST in a manner analogous to the procedures set forth above in Schemes I, II and III. The resulting fluorinated product possessing a nitro substituent on the phenyl group can then be hydrogenated under standard conditions well known to one of ordinary skill in the art to provide the corresponding amino substituted compound. For example, see J. March, "Advanced Organic Chemistry: Reactions, Mechanisms, and Structure," second edition, 1977, 1968 McGraw-Hill, Inc., pages 1125–1126.

In addition, compounds of structure (1a") can be prepared as disclosed in Scheme Va. The reagents and starting materials are readily available to one of ordinary skill in the art. All substituents, unless otherwise specified are as previously defined.

In Scheme Va, step A, the compound of structure (11a') is converted to the compound of structure (12a') in a manner analogous to the procedure described in Scheme IV, step A.

In Scheme Va, step B, the compound of structure (12a') is converted to the compound of structure (1a") in a manner analogous to the procedure described in Scheme IV, step B. Compound (1a") can then be converted to a sulfonamide, carbamate or urea in a manner analogous to the procedures described in Schemes I, II and III above. The resulting sulfonamide, carbamate, or urea can then be fluorinated with DAST in a manner analogous to the procedures set forth above in Schemes I, II and III.

The compounds of formula Id and formula Ie can be prepared following the procedure described in Scheme VI. The reagents and starting materials are readily available to one of ordinary skill in the art. All substituents, unless otherwise specified are as previously defined.

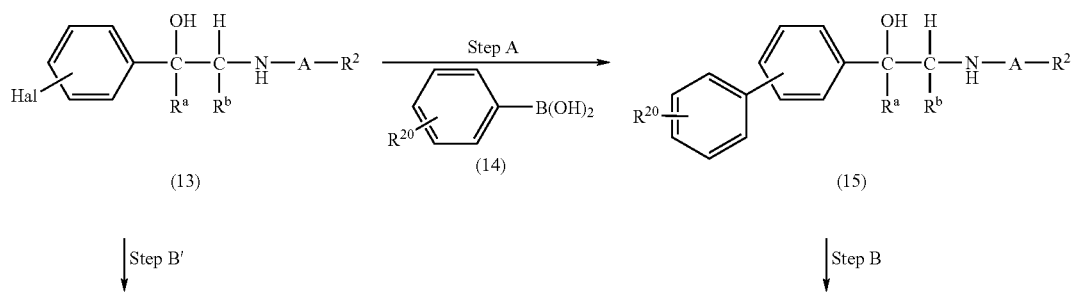

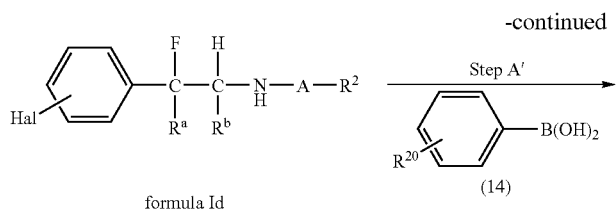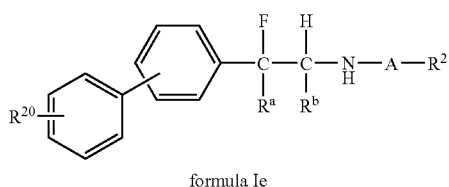

formula Id     (14)     formula Ie

In Scheme VI, step A the compound of structure (13) is coupled with compound of structure (14) under standard conditions to provide compound of structure (15). For example, compound (13) is combined with about 1.5 equivalents of compound (14), about 1.5 equivalents of potassium carbonate, and about 0.06 equivalents of tetrakis(triphenyl phosphine)palladium(0) in a suitable solvent or solvent mixture, such as dioxane/water (3:1). The mixture is then heated at about 100° C. for about 18 hours. The reaction is then cooled and compound (15) is isolated and purified using standard techniques and procedures, such as extraction techniques and chromatography. For example, the reaction mixture is extracted with a suitable organic solvent, such as ethyl acetate, the organic extracts are combined, washed with water, dried over anhydrous sodium sulfate, filtered, and concentrated under vacuum. The crude material is then purified by chromatography on silica gel with a suitable eluent, such as hexane/ethyl acetate to provide purified compound (15).

In Scheme VI, step B, compound (15) is fluorinated under standard conditions to provide the compound of formula Ie. For example, compound (15) is dissolved in a suitable organic solvent, such as methylene chloride is added to about one equivalent of DAST at about −78° C. with stirring under an atmosphere of nitrogen. The reaction is allowed to warm to room temperature and the compound of formula Ie is isolated and purified using standard techniques, such as extraction techniques and chromatography. For example, the reaction mixture is diluted with water and a suitable organic solvent, such as methylene chloride. The layers are separated and the organic layer is washed with water, dried over anhydrous sodium sulfate, filtered and concentrated under vacuum. The crude material is then purified by chromatography on silica gel with a suitable eluent, such as hexane/ethyl acetate to provide the purified compound of formula Ie.

Alternatively, in Scheme VI, step B' the compound (13) is fluorinated to provide the compound of formula Id in a manner analogous to the procedure described above in step B.

In addition, in Scheme VI, step A' the compound of formula Id is converted to the compound of formula Ie in a manner analogous to the procedure described above in step A.

More specifically, compounds of formula Ig and formula Ih can be prepared as shown in Scheme VII. Reagents and starting materials are readily available to one of ordinary skill in the art, for example, see International Patent Application No. PCT/US99/03449, published Sep. 2, 1999. All substituents, unless otherwise specified, are previously defined.

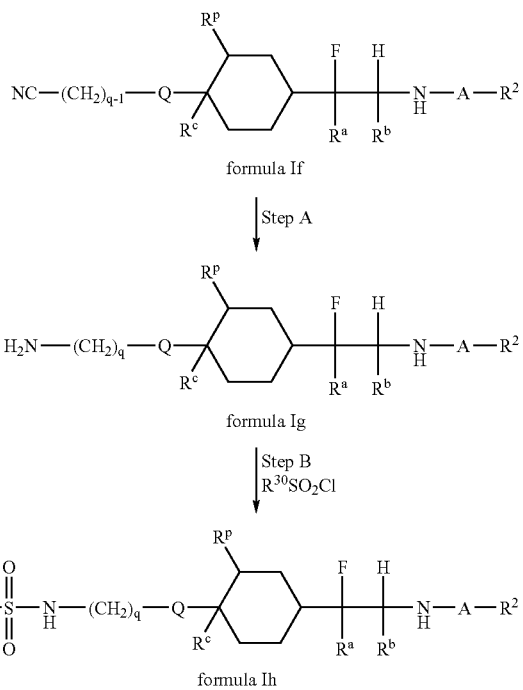

In Scheme VII, step A the compound of formula If wherein Q represents a (3–8C)cycloalkyl, an aromatic group, unsubstituted or substituted, such as phenyl, or a heteroaromatic group, unsubstituted or substituted, $R^c$ represents hydrogen, hydroxy, (1–4C)alkoxy, (1–4C)alkoxycarbonyl, or together with $R^p$ a bond, $R^p$ represents hydrogen, hydroxy, or together with $R^c$ a bond, q is an integer 1, 2, 3 or 4, $R^{30}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, and the remaining substituents are defined as hereinabove, is converted to the amine of formula Ig under conditions well known in the art. For example, compound If is dissolved in a suitable organic solvent, such as tetrahydrofuran and heat to reflux. To the refluxing solution is added about 1.1 equivalents of a borane reagent, such as borane dimethyl-sulfide complex. The reaction mixture is then heated at reflux for about 1 to 2 hours, cooled to room temperature and then treated with 6N HCl. The reaction is again heated at reflux for about 1 hour, cooled and the pH is adjusted to about pH 10 with aqueous sodium hydroxide. The product, compound Ig, is then isolated and purified by standard techniques such as extraction and chromatography.

For example, the reaction mixture is diluted with water and extracted with a suitable organic solvent, such as dichloromethane. The organic extracts are combined, dried over anhydrous magnesium sulfate, filtered and concentrated under vacuum to provide formula Ig.

In Scheme VII, step B the compound of formula Ig is sulfonylated to provide the compound of formula Ih under conditions well known in the art. For example, compound Ig is dissolved in a suitable organic solvent, such as dichloromethane, followed by addition of about 1.05 equivalents of triethylamine. The solution is cooled to about 0° C. and treated with about 1.05 equivalents of a suitable sulfonyl chloride of formula $R^{30}SO_2Cl$, such as methanesulfonyl chloride. The reaction is then allowed to warm to room temperature over 2 hours with stirring. The product compound Ih, is then isolated and purified using techniques well known to one of ordinary skill in the art, such as extraction and chromatography.

For example, the reaction mixture is then diluted with a suitable organic solvent, such as dichloromethane and 10% aqueous sodium bisulfate. The organic layer is separated and the aqueous layer is extracted with dichloromethane. The organic layer and extracts are then combined, dried over anhydrous sodium sulfate, filtered and concentrated under vacuum to provide compound Ih. Compound Ih can then be purified by flash chromatography on silica gel with a suitable eluent, such as ethyl acetate/hexane to provide purified compound Ih.

More specifically, compounds of formula Ij and formula Ik can be prepared as shown in Scheme VIII. Reagents and starting materials are readily available to one of ordinary skill in the art. All substituents, unless otherwise specified, are previously defined.

In Scheme VIII, step A the compound of formula If can be hydrolyzed under standard conditions to provide the compound of formula Ij. For example, compound If is dissolved in a suitable organic solvent, such as dioxane and treated with a suitable base, such as sodium hydroxide. The reaction mixture is then heated at about 100° C. for about 24 hours. The reaction mixture is then cooled to room temperature and acidified with 10% sodium bisulfate. Compound Ij is then isolated and purified by techniques well known in the art, such as extraction and chromatography.

For example, the reaction mixture is extracted with a suitable organic solvent, such as ethyl acetate, the organic extracts are combined, dried over anhydrous magnesium sulfate, filtered and concentrated under vacuum to provide compound Ij. Compound Ij can be purified by flash chromatography on silica gel with a suitable eluent, such as methanol/chloroform.

In Scheme VIII, step B the compound of formula Ij can be esterified under conditions well known in the art to provide the compound of formula Ik. For example, compound Ij is dissolved in a suitable organic solvent of formula $R^{40}OH$, wherein $R^{40}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C) alkoxy, such as ethanol and HCl gas is bubbled through the solution until the mixture is saturated. The reaction mixture is then heated at 60° C. for about 24 hours, then cooled to room temperature and concentrated under vacuum. Additional ethanol is added to the residue and the mixture is again concentrated under vacuum to provide the ethyl ester of compound Ik. Compound Ik can be then be purified by flash chromatography on silica gel with a suitable eluent, such ethyl acetate/hexane.

More specifically, compounds of formula Im can be prepared as shown in Scheme IX. Reagents and starting materials are readily available to one of ordinary skill in the art. All substituents, unless otherwise specified, are previously defined.

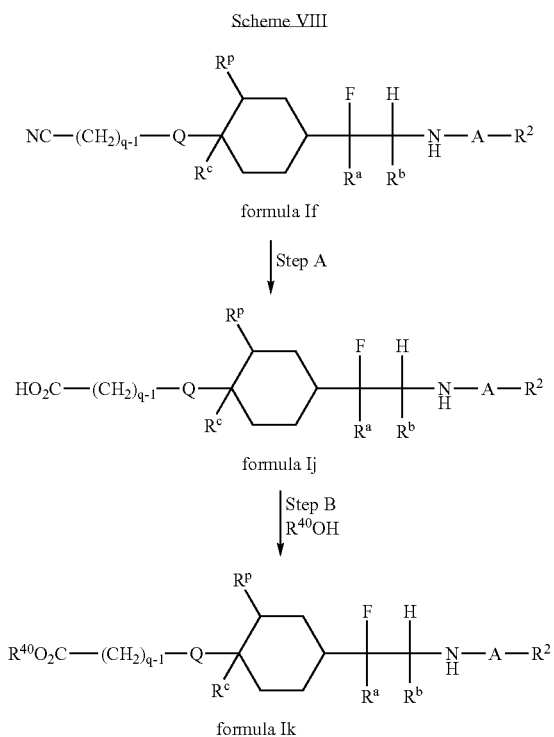

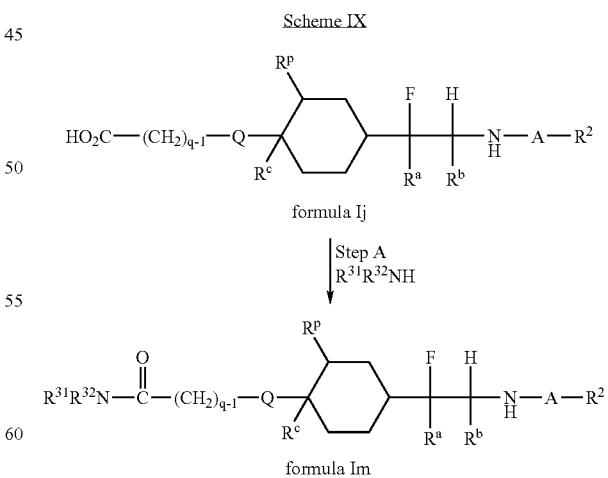

In Scheme IX, step A compound Ij is readily converted to the amide of formula Im under conditions well known in the art. For example, compound Ij is dissolved in a suitable organic solvent, such as tetrahydrofuran and treated with an excess of thionyl chloride. The reaction mixture is stirred at room temperature for about 16 hours and then concentrated under vacuum. The residue is then dissolved in a suitable organic solvent, such as methylene chloride. The solution is added to a solution of one equivalent of a suitable amine of formula $R^{31}R^{32}NH$, wherein $R^{31}$ and $R^{32}$ independently represent (1–4C)alkyl or together with the nitrogen atom to which they are attached form an azetidinyl, pyrrolidinyl, piperidinyl, morpholino, piperazinyl, hexahydroazepinyl or octahydroazocinyl group, such as dimethylamine in dichloromethane with stirring. The mixture is stirred for about 2 hours at about 0° C. and then 10% aqueous sodium bisulfate is added. Compound Im is then isolated and purified by techniques well known in the art, such as extraction and flash chromatography.

For example, the reaction mixture is then extracted with a suitable organic solvent, such as methylene chloride, the organic extracts are combined, dried over anhydrous sodium sulfate, filtered and concentrated under vacuum to provide compound Im. This can then be purified by flash chromatography on silica gel with a suitable eluent, such as ethyl acetate/hexane to provide the purified compound Im.

Compounds of formula In can be prepared as shown in Scheme X. Reagents and starting materials are readily available to one of ordinary skill in the art. All substituents, unless otherwise specified, are previously defined.

Compounds of formula Ip can be prepared as shown in Scheme XI. Reagents and starting materials are readily available to one of ordinary skill in the art. All substituents, unless otherwise specified, are previously defined.

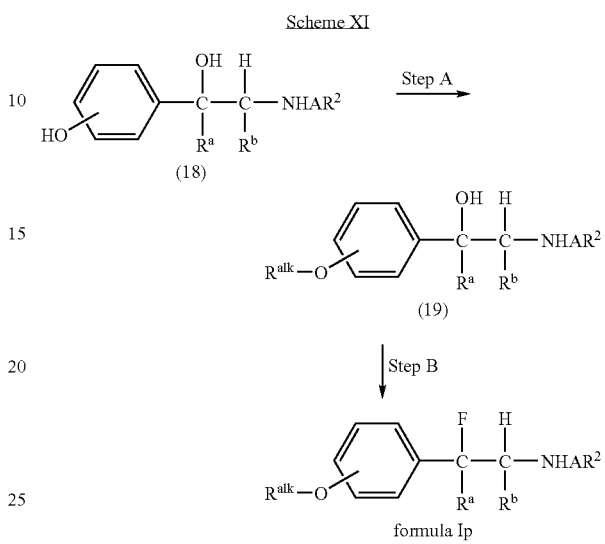

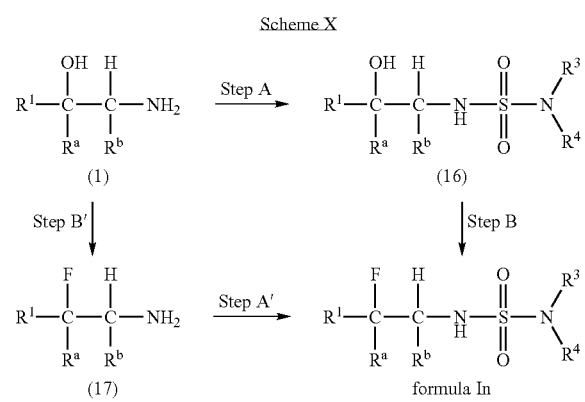

In Scheme X, step A, the compound of structure (1) is combined with a compound of formula $ClSO_2NR^3R^4$ under standard conditions to provide the compound of structure (16). For example, compound (1) is dissolved in a suitable organic solvent, such as tetrahydrofuran and treated with about one equivalent of a suitable base, such as DBU at about 0° C. The solution is then treated with about one equivalent of a compound of formula $ClSO_2NR^3R^4$. The reaction is then allowed to warm to room temperature and stirred for about 4 to 16 hours. The reaction is then concentrated under vacuum to provide the crude product (16) which can then be purified by chromatography on silica gel with a suitable eluent, such as ethyl acetate/hexane.

In Scheme X, step B, compound (16) is converted to the compound of formula In in a manner analogous to the procedure set forth in Scheme I, step B.

Alternatively, in Scheme X, step B' the compound (1) is fluorinated in a manner analogous to the procedure described in Scheme I, step B with DAST to provide the compound of structure (17). In Scheme X, step A' compound (17) is converted to the compound of formula In in a manner analogous to the procedure described above in step A.

In Scheme XI, step A, the phenol of structure (18) is alkylated with a suitable alkylating agent of structure $R^{alk}$-Hal under standard conditions wherein Hal is Br or Cl, and $R^{alk}$ is an unsubstituted or substituted aromatic group, an unsubstituted or substituted heteroaromatic group, an unsubstituted or substituted (5–8C)cycloalkyl group, (1–10C)alkyl; (2–10C)alkenyl; or (2–10C)alkynyl to provide the compound of structure (19). For example, compound (18) is added to about one equivalent of a suitable base, such as sodium hydride, in a suitable organic solvent, such as dimethylformamide. The reaction mixture is stirred for about 30 minutes at room temperature and treated with about one equivalent of a suitable alkylating agent $R^{alk}$-Hal followed by addition of sodium iodide. The reaction is heated at about 100° C. for about 2 hours and then cooled. The reaction is diluted with water, extracted with a suitable organic solvent, such as ethyl acetate, the organic extracts are combined, washed with water, dried over anhydrous sodium sulfate, filtered, and concentrated to provide crude compound (19). The crude material can be purified by chromatography on silica gel with a suitable eluent, such as ethyl acetate/hexane.

In Scheme X, step B, the compound (19) is fluorinated in a manner analogous to the procedure described in Scheme I, step B with DAST to provide the compound of formula Ip.

Compounds of formula Iq can be prepared as shown in Scheme XII. Reagents and starting materials are readily available to one of ordinary skill in the art. All substituents, unless otherwise specified, are previously defined.

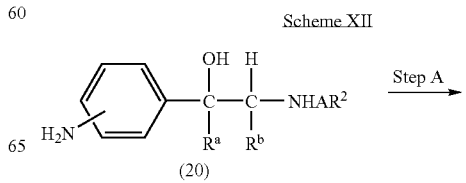

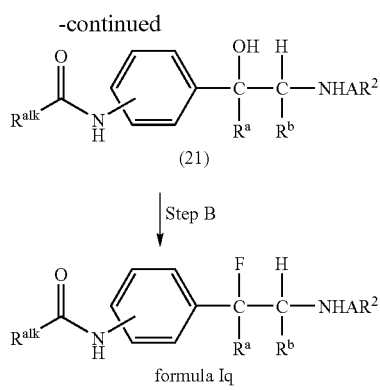

(21)

↓ Step B formula Iq

In Scheme XII, step A, the compound of structure (20) is converted to the amide of structure (21) under standard amide coupling conditions well known in the art. For example, the compound (20) is dissolved in a suitable organic solvent, such as methylene chloride, and treated with a catalytic amount of dimethylaminopyridine (DMAP), about 1.6 equivalents of 1-[3-(dimethylamino)propyl]-3-ethylcarbodiimide, and about one equivalent of a suitable acid of formula $R^{alk}CO_2H$. $R^{alk}$ is an unsubstituted or substituted aromatic group, an unsubstituted or substituted heteroaromatic group, an unsubstituted or substituted (5–8C)cycloalkyl group, (1–10C) alkyl; (2–10C)alkenyl; or (2–10C)alkynyl. The reaction mixture is stirred at room temperature for about 4 to 64 hours and poured into water. The quenched reaction mixture is then extracted with a suitable organic solvent, such as ethyl acetate, the combined organic extracts are washed with water, dried over anhydrous sodium sulfate, filtered, and concentrated under vacuum to provide crude (21). The crude material can be purified by chromatography on silica gel with a suitable eluent, such as ethyl acetate/hexane.

Alternatively, in Step A, compound 20 is dissolved in a suitable organic solvent, such as tetrahydrofuran with about 1.2 equivalents of triethylamine added. The solution is then treated dropwise with about one equivalent of an acid chloride of formula $R^{alk}COCl$. $R^{alk}$ is an unsubstituted or substituted aromatic group, an unsubstituted or substituted heteroaromatic group, an unsubstituted or substituted (5–8C)cycloalkyl group, (1–10C) alkyl; (2–10C)alkenyl; or (2–10C)alkynyl. The reaction mixture is stirred at room temperature for about 2 to 24 hours and poured into water. The quenched reaction mixture is then extracted with a suitable organic solvent, such as ethyl acetate, the combined organic extracts are washed with water, dried over anhydrous sodium sulfate, filtered, and concentrated under vacuum to provide crude (21). The crude material can be purified by chromatography on silica gel with a suitable eluent, such as ethyl acetate/hexane.

In Scheme XII, step B, the compound (21) is fluorinated in a manner analogous to the procedure described in Scheme I, step B with DAST to provide the compound of formula Iq.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK 293 cells stably expressing human GluR4B (obtained as described in European Patent Application Publication Number EP-A1-583917) are prepared. The tissue culture medium in the wells is then discarded, and the wells are each washed once with 200 µl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 µM Fluo3-AM dye (obtained from Molecular Probes Inc., Eugene, Oreg.) in buffer in each well. After the incubation, each well is washed once with 100 µl buffer, 200 µl of buffer is added and the plates are incubated for 30 minutes.

Solutions for use in the test are also prepared as follows. 30 µM, 10 µM, 3 µM and 1 µM dilutions of test compound are prepared using buffer from a 10 mM solution of test compound in DMSO. 100 µM cyclothiazide solution is prepared by adding 3 µl of 100 mM cyclothiazide to 3 ml of buffer. Control buffer solution is prepared by adding 1.5 µl DMSO to 498.5 µl of buffer.

Each test is then performed as follows. 200 µl of control buffer in each well is discarded and replaced with 45 µl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 µl of buffer and 45 µl of test compound in buffer in appropriate wells. A second fluorescent reading is taken after 5 minutes incubation. 15 µl of 400 µM glutamate solution is then added to each well (final glutamate concentration 100 µM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 µM cyclothiazide.

In another test, HEK293 cells stably expressing human GluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al. (1981) Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 µM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 µM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium Stearate | 10 |
| Total | 460 |

The above ingredients are mixed and filled into hard gelatin capsules in 460 mg quantities.

Formulation 2

Tablets each containing 60 mg of active ingredient are made as follows:

|  | Quantity (mg/tablet) |
| --- | --- |
| Active Ingredient | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein, the terms "treating" or "to treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds can be administered by a variety of routes including oral, rectal, transdermal, subcutaneous, intravenous, intramuscular, bucal or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following examples and preparations represent typical syntheses of the compounds of formula I as described generally above. These examples are illustrative only and are not intended to limit the invention in any way. The reagents and starting materials are readily available to one of ordinary skill in the art. As used herein, the following terms have the meanings indicated: "eq" refers to equivalents; "g" refers to grams; "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "EtOAc" refers to ethyl acetate; "aq" refers to aqueous; "iPrOAc" refers to isopropyl acetate; "methyl DAST" refers to dimethylaminosulfur trifluoride, "DAST" refers to diethylaminosulfur trifluoride, "DBU" refers to 1,8-diazabicyclo[5.4.0]undec-7-ene; and "RT" refers to room temperature.

EXAMPLE 1

Preparation of [2-Fluoro-2-(4-iodophenyl)propyl][(methylethyl)sulfonyl]amine

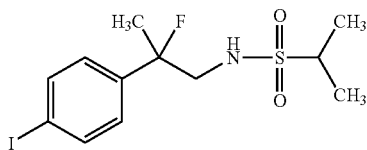

Preparation of 1-Amino-2-(4-iodophenyl)propan-2-ol

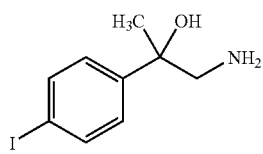

Scheme IV, Step A: The trimethylsilyl-protected cyanohydrin derivative of 4-iodoacetophenone was prepared in situ following generally the method disclosed by Greenlee and Hangauer, *Tetrahedron Lett.*, 24(42), 4559 (1983). Accordingly, cyanotrimethylsilane (21.4 g, 0.216 mol) was added dropwise over 5 minutes to a dry, room temperature solution containing 4-iodoacetophenone (44.3 g, 0.180 mol), 18-crown-6 (1.6 g, 6.1 mmoles) and KCN (1.17 g, 0.018 mol) in THF (100 mL). The resulting solution was allowed to stir for 2.5 h. TLC analysis (3:7 EtOAc/Hexanes) showed consumption of starting acetophenone.

Scheme IV, step B: A 10M solution of borane in dimethylsulfide (25 mL, 0.25 mol) was added rapidly to the reaction solution and the resulting mixture was heated at reflux for 16 h. The mixture was cooled to room temperature and anhydrous 10% (by wt) HCl in methanol was added slowly over 1 h (GAS EVOLUTION). The solution was allowed to stir for an additional hour, and was concentrated under reduced pressure to give the crude title compound as white solid and as the hydrochloride salt. This salt was triturated with methyl t-butyl ether and filtered. The free base was prepared by adding 1N NaOH to a suspension of the HCl salt in $CH_2Cl_2$ (150 mL) and THF (350 mL) until pH 12.3 was reached. The phases were separated and the organic phase was washed with brine (25 mL). The organic phase containing the free amine was concentrated under reduced pressure and the resulting solids were triturated with diethyl ether (30 mL) to afford the intermediate title compound (35.6 g, 71.3%) as an off-white powder after vacuum drying. $^1$H NMR ($CD_3OD$, 300 MHz): δ 7.68 (d, 2H, J=8.4), 7.24 (d, 2H, J=8.7), 2.78 (m, 2H), 1.46 (s, 3H).

Preparation of [2-Hydroxy-2-(4-iodophenyl)propyl][(methylethyl)sulfonyl]amine

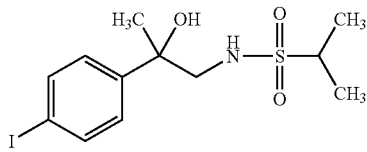

Scheme I, Step A: Into a 250 mL 3 necked flask fitted with a stirrer and thermometer, was added dropwise 2-propanesulfonyl chloride (1.60 g, 0.011 mol) to 1-amino-2-(4-iodophenyl)propan-2-ol (2.77 gm, 0.01 mol) in 125 mL $CH_2Cl_2$ while stirring at 0° C. under nitrogen. The reaction was then allowed to warm to room temperature and stirred overnight at this temperature. In the morning, the mixture was poured into $H_2O$ and the layers were separated. The organic layer was washed once with $H_2O$, dried over anhydrous $Na_2SO_4$, filtered, and concentrated under reduced vacuum. The resulting semi-solid was purified via silica gel chromatography employing the Prep. LC-2000 and eluting with a solvent of Hexane/EtOAc 3:1 to provide the intermediate title compound (744 mg, 19%) as a solid material. FDMS 382 (M*).

Analysis for $C_{12}H_{18}NO_3S$ I:

| | | | | | |
|---|---|---|---|---|---|
| Theory: | C, 37.61 | | H, 4.73 | | N, 3.65 |
| Found: | C, 38.08 | | H, 4.26 | | N, 3.55 |

Alternative Preparation of Title Compound

Scheme I, step A: In a 250 mL-3 neck flask fitted with a stirrer and thermometer, 2.10 g. of propanesulfonyl chloride was added dropwise to 2.77 g. of 1-amino-2-(4-iodophenyl)propan-2-ol and 2.30 g. of DBU in $CH_2Cl_2$ (150 mL) while stirring at 0° C. under a nitrogen atmosphere. The reaction was allowed to warm to room temperature and stirred overnight at this temperature. In the morning, the reaction was diluted with $CH_2Cl_2$ (100 mL) and the organic layer was washed two times with $H_2O$, dried over anhydrous $Na_2SO_4$, filtered, and concentrated under reduced vacuum to yield a viscous oil. This material was purified via silica gel chromatography employing the Chromatotron, using a 4000 micron rotor and eluting with a solvent of methylene chloride/methanol 19:1 to yield the intermediate title compound (1.0 g, 31%) as a viscous oil. Ion spray M.S. 382 (M*–1).

Preparation of Final Title Compound

Scheme I, Step B: Into a 10 mL single neck flask, a solution of [2-hydroxy-2-(4-iodophenyl)propyl][(methylethyl)sulfonyl]amine (158 mg, 0.41 mmol) in 1.7 mL $CH_2Cl_2$ was added syringe wise slowly to a solution of DAST (66 mg, 0.41 mmol) in 0.3 mL $CH_2Cl_2$ while stirring at −78° C. under nitrogen. The reaction was then allowed to warm to room temperature and the mixture was diluted with $H_2O$ and $CH_2Cl_2$. The layers were separated and the organic layer was washed twice with $H_2O$, dried over anhydrous $Na_2SO_4$, filtered, and concentrated under reduced vacuum to provide the final title compound (113 mg) as a solid. Ion spray M.S. 384 (M*−1).

Additional Preparation of Final Title Compound

Scheme I, step B: Into a 100 mL 3-neck flask fitted with a stirrer and thermometer, 1.0 g. of [2-hydroxy-2-(4-iodophenyl)propyl][(methylethyl)sulfonyl]amine in $CH_2Cl_2$ (15 mL) was added dropwise to 0.3 mL DAST in $CH_2CL_2$ (10 mL) while stirring at −78° C. under a nitrogen atmosphere. Reaction was allowed to warm to room temperature and diluted with $CH_2Cl_2$ (50 mL). This organic layer was washed with $H_2O$, dried over anhydrous $Na_2SO_4$, filtered, and concentrated under reduced vacuum to yield an oil. This material was purified via silica gel chromatography employing the Chromatotron and using a 4000 micron rotor while eluting with a gradient solvent of hexane/ethyl acetate 9:1 to hexane/ethyl acetate 3:1 to yield the final title compound (0.906 g) as a white solid. Ion spray M.S. 384 (M*−1).

Analysis for $C_{12}H_{17}NO_2SFI$:

| Theory: | C, 37.42 | H, 4.44 | N, 3.64 |
|---|---|---|---|
| Found: | C, 37.27 | H, 4.33 | N, 3.61 |

EXAMPLE 1a

Preparation of (+)-[2-Fluoro-2-(4-iodophenyl)propyl][(methylethyl)sulfonyl]amine and (−)-[2-Fluoro-2-(4-iodophenyl)propyl][(methylethyl)sulfonyl]amine

[2-fluoro-2-(4-iodophenyl)propyl][(methylethyl)sulfonyl]amine (2.0 g, prepared in example 1) was dissolved into 3A ethanol (30 mL) and was further diluted with heptane (20 mL). [As used herein the term "3A ethanol" refers to ethanol containing 5% methanol.] The mixture was agitated via ultrasound to form a clear, colorless solution. This lot was loaded upon a 8×28 cm preparative Chiralpak AD chromatographic column that was pre-equilibrated with 60% 3A ethanol/40% heptane. Eluent flow was 300 mL/min and detection wavelength was 240 nm. The first eluting substance was (+)-[2-fluoro-2-(4-iodophenyl)propyl][(methylethyl)sulfonyl]amine, $[\alpha]_D$=+18.5 (c=1.08, MeOH), and the subsequent eluting substance was (−)-[2-fluoro-2-(4-iodophenyl)propyl][(methylethyl)sulfonyl]amine, $[\alpha]_D$=−23.5 (c=1.02, MeOH). The above procedure was repeated twice in an analogous manner with [2-fluoro-2-(4-iodophenyl)propyl][(methylethyl)sulfonyl]amine (second run, 3.0 g dissolved in 50 mL 3A ethanol/heptane, 3:2 and a third run, 2.0 g dissolved in 0.8 g dissolved in 40 mL 3A ethanol/heptane, 3:2). Thus, in three runs, a total of 5.8 g of [2-fluoro-2-(4-iodophenyl)propyl][(methylethyl)sulfonyl]amine was resolved into its component enantiomers in the following yields after concentration (in vacuo) of fractions:

(+)-[2-fluoro-2-(4-iodophenyl)propyl][(methylethyl)sulfonyl]amine (2.38 g, 41.0%);

(−)-[2-fluoro-2-(4-iodophenyl)propyl][(methylethyl)sulfonyl]amine (1.2 g, 20.7%).

Analysis conditions: 0.46×35 cm Chiralpak AD 60% ethanol (5% methanol)/40% Heptane; Flow: 1.0 mL/min, detection wavelength: 240 nm.

For (+)-[2-fluoro-2-(4-iodophenyl)propyl][(methylethyl)sulfonyl]amine: $R_t$=5.4 min, MS (ES+) 384 (M−1). $^1H$ NMR ($CDCl_3$, 300 MHz): δ 7.73 (d, 2H, J=8.1), 7.09 (d, 2H, J=8.4), 4.27 (t, 1H, J=6.2), 3.50 (m, 2H), 3.03 (m, 1H), 1.69 (d, 3H, J=22), 1.30 (d, 3H, J=7), 1.27 (d, 3H, J=7). Analysis for $C_{12}H_{17}FINO_2S$: Theory: C, 37.41; H, 4.45; N, 3.64. Found: C, 37.54; H, 4.43; N, 3.64.

For (−)-[2-fluoro-2-(4-iodophenyl)propyl][(methylethyl)sulfonyl]amine: $R_t$=10.1 min. MS (ES+) 384 (M−1). $^1H$ NMR spectrum identical to that of (+)-[2-fluoro-2-(4-iodophenyl)propyl][(methylethyl)sulfonyl]amine. Analysis for $C_{12}H_{17}FINO_2S$: Theory: C, 37.41; H, 4.45; N, 3.64. Found: C, 37.56; H, 4.43; N, 3.59.

EXAMPLE 2

Preparation of [2-Fluoro-2-(4-phenylphenyl)propyl][(methylethyl)sulfonyl]amine

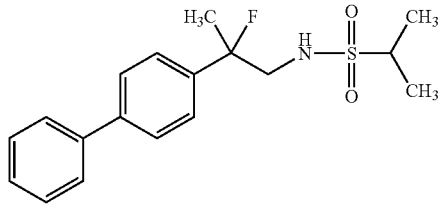

Scheme VI, Step A': Into a 10 mL single neck flask was placed [2-fluoro-2-(4-iodophenyl)propyl][(methylethyl)sulfonyl]amine (113 mg, 0.29 mmol, prepared in example 1), phenyl boric acid (54 mg, 0.44 mmol), potassium carbonate (61 mg, 0.44 mmol), and tetrakis(triphenyl phosphine)Pd(0) (17 mg, 0.02 mmol) in a mixture of dioxane/water (3:1, 7 mL). The mixture was then heated at 100° C. with stirring for 18 hours. The reaction was then cooled to room temperature and poured into $H_2O$. The mixture was extracted with EtOAc and the organic layer was washed twice with $H_2O$, dried over anhydrous $Na_2SO_4$, filtered, and concentrated under reduced vacuum. The resulting semi-solid was purified via radial chromatography (Chromatotron, Harrison Research Inc., 840 Moana Court, Palo Alto, Calif. 94306) using a 2000 micron rotor (silica gel) and eluting with a solvent of Hexane/EtOAc 4:1 to provide the title compound (33 mg, 34%) as a slowly crystallizing tan oil. Ion spray M.S. 335 (M*+1).

Analysis for $C_{18}H_{22}NO_2S$:

| Theory: | C, 64.45 | H, 6.61 | N, 4.18 |
|---|---|---|---|
| Found: | C, 65.50 | H, 6.46 | N, 4.05 |

EXAMPLE 3

Preparation of 4-[4-(1-Fluoro-1-methyl-2-{[(methylethyl)sulfonyl]amino}ethyl)phenyl]benzenecarbonitrile

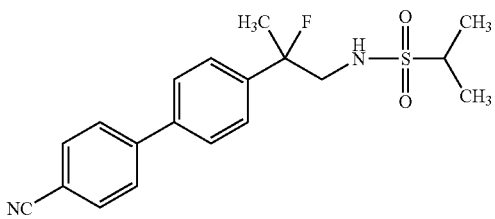

Preparation of 4-Cyanobenzene Boronic Acid

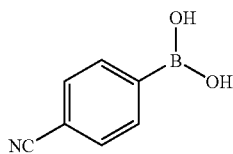

A solution of 4-bromobenzonitrile (91 g, 0.50 mole) in THF (1.1 L) was dried in the presence of activated 3 Å molecular sieves at room temp. This solution was filtered and cooled to −100° C. A 1.6 M solution of n-butyllithium in hexanes (355 mL. 0.567 mol) was added to the cold solution over 15 min while maintaining the internal temperature between −105 and −93° C. To the resulting orange reaction mixture was added trimethylborate (81 g, 0.78 mol) over 3 min, briefly increasing the reaction temperature to −72° C. The reaction mixture was recooled to −100° C. over 5 minutes and then was allowed to warm slowly to room temperature over 2.3 h. The reaction mixture was acidified with 4N HCl to pH 2.2, and was diluted with $CH_2Cl_2$ (200 mL). The aqueous layer was separated and the organic layer was washed with brine (2×200 mL), dried over anhydrous $MgSO_4$, filtered, and the solvent removed under reduced pressure to a pale yellow solid. This solid was additionally purified by dissolution in 1N NaOH and extraction into $CH_2Cl_2$/THF (1:1, 2×200 mL). The aqueous phase was acidified with 4N HCl to pH 2.2 and was extracted into $CH_2Cl_2$/THF (1:1, 500 mL). The combined organic extracts were concentrated to a crude solid (64.6 g) that was triturated with diethyl ether (160 mL) and dried under vacuum to afford the intermediate title compound (44.0 g, 59.9%) as a white powder. $^1$H NMR ($d_6$-acetone, 300 MHz): δ 8.03 (d, 2H, J=8.1), 7.75 (d, 2H, J=8.4), 7.54 (s, 2H).

Preparation of 4-[4-(1-Hydroxy-1-methyl-2-{[(methylethyl)sulfonyl]amino}ethyl)phenyl]benzenecarbonitrile

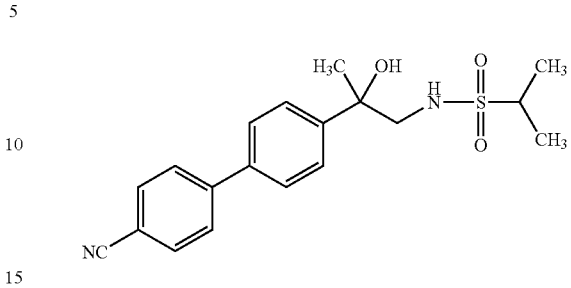

Scheme VI, Step A: Into a 50 mL single neck flask was placed 2-hydroxy-2-(4-iodophenyl)propyl][(methylethyl)sulfonyl]amine (350 mg, 0.90 mmol, intermediate prepared in example 1), 4-cyanobenzene boronic acid (206 mg, 1.40 mmol), potassium carbonate (193 mg, 1.40 mmol), and tetrakis(triphenyl phosphine)palladium(0) (52 mg, 0.045 mmol) in dioxane/water (3:1, 25 mL), and the mixture was heated at 100° C. with stirring for 18 hours. The reaction was cooled to room temperature and poured into $H_2O$. The reaction mixture was extracted with EtOAc and the organic layer was separated and washed twice with $H_2O$, dried over anhydrous $Na_2SO_4$, filtered, and concentrated under reduced vacuum. The resulting semi-solid was purified via radial chromatography (Chromatotron) using a 4000 micron rotor (silica gel) and eluting with a solvent of Hexane/EtOAc 3:1 to provide the intermediate title compound (265 mg, 82%) as a solid. Ion spray M.S. 357 (M*−1).

Analysis for $C_{19}H_{22}N_2O_3S$:

| Theory: | C, 63.66 | H, 6.18 | N, 7.81 |
| Found:  | C, 63.26 | H, 6.49 | N, 7.67 |

Preparation of Final Title Compound

Scheme VI, Step B: Into a 25 mL single neck flask, a solution of 4-[4-(1-hydroxy-1-methyl-2-{[(methylethyl)sulfonyl]amino}ethyl)phenyl]benzenecarbonitrile (253 mg, 0.70 mmol) in 8 mL $CH_2Cl_2$ was added syringe wise slowly to a solution of DAST (114 mg, 0.71 mmol) in 2 mL $CH_2Cl_2$ while stirring at −78° C. under an atmosphere of nitrogen. The reaction was then allowed to warm to room temperature and the mixture was diluted with $H_2O$ and $CH_2Cl_2$. The layers were separated and the organic layer was washed twice with $H_2O$, dried over anhydrous $Na_2SO_4$, filtered, and concentrated under reduced vacuum to provide the crude title compound as a solid. This crude material was then purified via radial chromatography using a 2000 micron rotor (silica gel) and eluting with a solvent of Hexane/EtOAc 3:1 to provide the title compound (174 mg, 69%) as a white solid. m.p. 123°–126° C. Ion spray M.S. 359 (M*−1).

Analysis for $C_{19}H_{21}N_2O_2SF$:

| Theory: | C, 63.31 | H, 5.87 | N, 7.77 |
| Found:  | C, 62.72 | H, 5.76 | N, 7.72 |

EXAMPLE 4

Preparation of 4-[4-(1-Fluoro-1-methyl-2-{[(methyl-ethyl)sulfonyl]amino}ethyl)phenyl]benzoic Acid

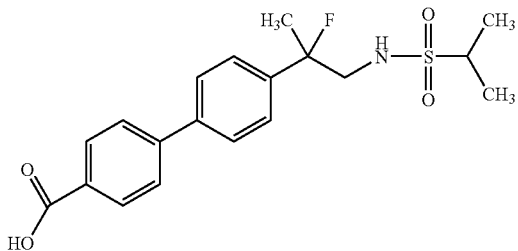

Scheme VI, Step A': Into a 50 mL single neck flask [2-fluoro-2-(4-iodophenyl)propyl][(methylethyl)sulfonyl]amine (300 mg, 0.78 mmol, prepared in example 1), 4-carboxybenzene boronic acid (188 mg, 1.13 mmol), potassium carbonate (156 mg, 1.13 mmol) and tetrakis(triphenyl phosphine)palladium(0) (52 mg, 0.05 mmol) were combined in dioxane/water (30 mL, 3:1). The mixture was then heated at 100° C. with stirring for 18 hours. The reaction was cooled to room temperature and poured into $H_2O$. The desired product was extracted with ethyl acetate and the organic layer was separated, washed twice with $H_2O$, dried over $K_2CO_3$, and concentrated under reduced vacuum to yield the crude material (350 mg) as a tan solid. The crude material was purified via silica gel chromatography employing the Chromatotron using a 4000 micron rotor and eluting with a solvent of methylene chloride/methanol 9:1 to yield the title compound (91 mg, 31%) as a white solid.

Ion spray M.S. 378 (M*–1)

EXAMPLE 4a

Preparation of 4-[4-(1-Fluoro-1-methyl-2-{[(methyl-ethyl)sulfonyl]amino}ethyl)phenyl]benzoic Acid (Enantiomer 1)

(+)-[2-Fluoro-2-(4-iodophenyl)propyl][(methylethyl)sulfonyl]amine (1.00 g, 2.6 mmol, prepared in example 1a), 4-carboxybenzene boronic acid (627 mg, 3.8 mmol), potassium carbonate (520 mg, 3.8 mmol), tetrakis(triphenyl phosphine)palladium(0) (206 mg, 0.2 mmol) and dioxane/water (112 mL, 3:1) were mixed together in a 250 mL single neck flask and stirred at 80° C. for 4 hours. The reaction was cooled to room temperature and poured into 1N HCl and the desired product was extracted with ethyl acetate. The organic layer was dried over $MgSO_4$, filtered, and concentrated under reduced pressure to yield 1.43 g as a dark oil. This material was purified via silica gel chromatography employing the chromatotron and using a 4000 micron rotor while eluting with a solvent of methylene chloride/methanol 9:1 to yield the title compound (355 mg, 36%) as a tan solid. Ion spray M.S. 378.3 (M*–1).

EXAMPLE 4b

Preparation of 4-[4-(1-Fluoro-1-methyl-2-{[(methyl-ethyl)sulfonyl]amino}ethyl)phenyl]benzoic Acid (Enantiomer 2)

(–)-[2-Fluoro-2-(4-iodophenyl)propyl][(methylethyl)sulfonyl]amine (1.00 g, 2.6 mmol, prepared in example 1a), 4-carboxybenzene boronic acid (485 mg, 2.9 mmol), $Na_2CO_3/H_2O$ (4.4 mL, excess), tetrakis(triphenyl phosphine)palladium(0) (206 mg, 0.2 mmol) and dioxane (20 mL) were mixed together in a 50 mL single neck flask and stirred at 80° C. for 4 hours. The reaction was cooled to room temperature and poured into 1N HCl and the desired product was extracted with ethyl acetate. The organic layer was dried over $MgSO_4$, filtered, and concentrated under reduced pressure to yield 871 mg as a foam. This material was purified via silica gel chromatography employing the chromatotron and using a 4000 micron rotor while eluting with a solvent of methylene chloride/methanol 9:1 to yield the title compound (500 mg, 51%) as a tan solid. Ion spray M.S. 378.1 (M*–1).

Calculated for: $C_{19}H_{22}NO_4S$ F—$H_2O$:

| | | | |
|---|---|---|---|
| Theory: | C 57.41, | H 6.09, | N 3.52. |
| Found: | C 57.20, | H 5.82, | N 3.52. |

EXAMPLE 5

Preparation of {2-[4-(3-Aminophenyl)phenyl]-2-fluoropropyl}[(methylethyl)sulfonyl]amine

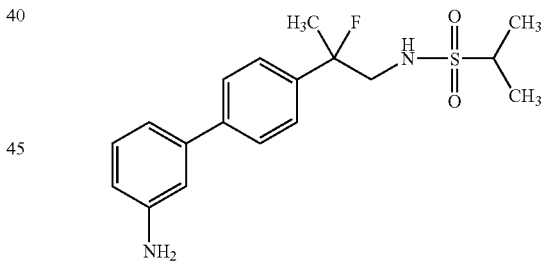

Scheme VI, Step A': Into a 50 mL single neck flask [2-fluoro-2-(4-iodophenyl)propyl][(methylethyl)sulfonyl]amine (200 mg, 0.53 mmol, prepared in example 1), 3-aminobenzene boronic acid (188 mg, 0.76 mmol), potassium carbonate (104 mg, 0.76 mmol) and tetrakis(triphenyl phosphine)palladium(0) (41 mg, 0.036 mmol) were combined in dioxane/water (20 mL, 3:1). The mixture was heated at 100° C. under stirring for 18 hours. The reaction was cooled to room temperature and poured into $H_2O$. The desired product was extracted with ethyl acetate and the organic layer was separated and washed twice with $H_2O$, dried over $K_2CO_3$, and concentrated under reduced vacuum to yield the crude material (276 mg) as a dark oil. The resulting oil was purified via silica gel chromatography employing the Chromatotron using a 4000 micron rotor and eluting with a solvent of Hexane/Ethyl Acetate 1:1 to yield the title compound (164 mg, 90%) as a viscous oil. Ion spray M.S. 351.4 (M*+1).

Analysis calculated for: $C_{18} H_{23} N_2 O_2 S F$:

| Theory: | C, 61.69 | H, 6.62 | N, 7.99 |
|---|---|---|---|
| Found: | C, 61.53 | H, 6.55 | N, 8.13 |

EXAMPLE 6

Preparation of [2-Fluoro-2-(4-{3-[(methylsulfonyl)amino]phenyl}phenyl)propyl][(methylethyl)sulfonyl]amine

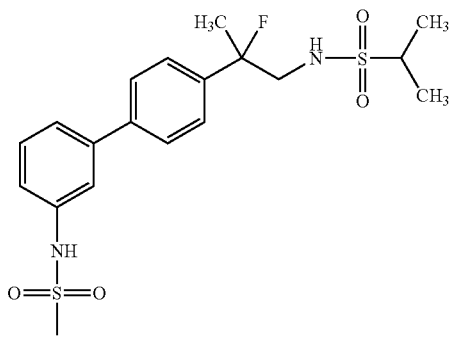

A 50 mL flask fitted with a stirrer and thermometer was charged with DBU (67 mg, 1.1 eq), {2-[4-(3-aminophenyl)phenyl]-2-fluoropropyl}[(methylethyl)sulfonyl]amine (140 mg, 0.44 mmol, prepared in example 5) and methylene chloride (10 mL) under an atmosphere of nitrogen, and cooled to 0° C. To this stirring solution was added dropwise chloro-methane sulfonyl chloride (69 mg, 1.5 eq). The reaction was allowed to warm to room temperature and stirred overnight at this temperature. In the morning, the mixture was poured into H₂O and the layers were separated. The organic layer was washed once with H₂O, dried over anhydrous Na₂SO₄, filtered, and concentrated under reduced vacuum to yield the crude material (192 mg) as a yellow oil. This crude material was purified via silica gel chromatography employing the Chromatotron using a 4000 micron rotor and eluting with a solvent of Methylene Chloride/ethyl acetate 9:1 to yield the title compound (50 mg, 29%) as a white foam. Ion spray mass spectra 427.1 (M*−1).

Analysis for $C_{19} H_{25} N_2 O_4 S_2 F$:

| Theory: | C, 53.25 | H, 5.88 | N, 6.54 |
|---|---|---|---|
| Found: | C, 53.56 | H, 6.11 | N, 6.29 |

EXAMPLE 6a

Preparation of [2-Fluoro-2-(4-{3-[(methylsulfonyl)amino]phenyl}phenyl)propyl][(methylethyl)sulfonyl]amine (Enantiomer 1)

(+)-[2-Fluoro-2-(4-iodophenyl)propyl][(methylethyl)sulfonyl]amine (300 mg, 0.78 mmol, prepared in example 1a), the borate of formula:

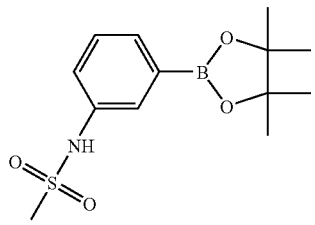

(347 mg, 1.5 eq.), potassium carbonate (156 mg, 1.5 eq), tetrakis(triphenyl phosphine)palladium(0) (75 mg, 0.06 mmol) and dioxane/water (36 mL, 3:1) were mixed together in a 100 mL single neck flask and stirred at 80° C. for 4 hours. The reaction was cooled to room temperature and poured into H₂O and the desired product was extracted with ethyl acetate. The organic layer was backwashed once with H₂O, dried over K₂CO₃, filtered, and concentrated under reduced pressure to yield 191 mg as a viscous oil. This material was purified via silica gel chromatography employing the chromatotron and using a 2000 micron rotor while eluting with a solvent of hexane/ethyl acetate 1:1 to yield the title compound (86 mg, 26%) as a white solid. Ion spray M.S. 427.1 (M*−1).

Calculated for: $C_{19}H_{25}N_2O_4S_2$ F—H₂O:

| Theory: | C 51.08, | H 6.09, | N 6.27. |
|---|---|---|---|
| Found: | C 51.29, | H 5.63, | N 6.29. |

EXAMPLE 6b

Preparation of [2-Fluoro-2-(4-{3-[(methylsulfonyl)amino]phenyl}phenyl)propyl][(methylethyl)sulfonyl]amine (Enantiomer 2)

(−)-[2-Fluoro-2-(4-iodophenyl)propyl][(methylethyl)sulfonyl]amine (493 mg, 1.28 mmol, prepared in example 1a), the borate of formula:

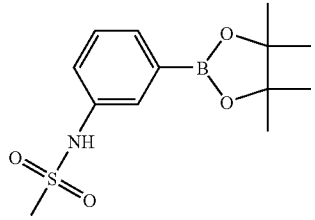

(385 mg, 1.30 mmol), 2.0 M Na₂CO₃/H₂O (2.2 mL, excess), tetrakis(triphenyl phosphine)palladium(0) (100 mg, 0.09 mmol) and dioxane (15 mL) were mixed together in a 50 mL single neck flask and stirred at 80° C. overnight. In the morning the reaction was cooled to room temperature and poured into H₂O and the desired product was extracted with ethyl acetate. The organic layer was backwashed once with H₂O, dried over K₂CO₃, filtered, and concentrated under reduced pressure to yield 571 mg as a foam. This material was purified via silica gel chromatography employing the chromatotron and using a 4000 micron rotor while eluting with a solvent of hexane/ethyl acetate 1:1 to yield the title compound (294 mg, 56%) as a brown solid. Ion spray M.S. 427.3 (M*−1).

Calculated for: $C_{19}H_{25}N_2O_4S_2$ F—H₂O: Theory: C, 51.08; H, 6.09; N, 6.27. Found: C, 51.29; H, 5.63; N, 6.29.

EXAMPLE 7

Preparation of [2-Fluoro-2-(4-(3-thienyl)phenyl)propyl][(methylethyl)sulfonyl]amine

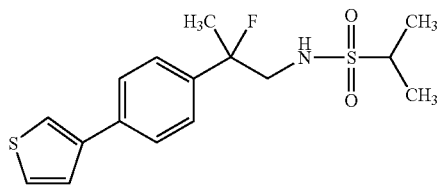

Scheme VI, Step A': Into a 50 mL single neck [2-fluoro-2-(4-iodophenyl)propyl][(methylethyl)sulfonyl]amine (150 mg, 0.39 mmol, prepared in example 1), thiophene-3-benzene boronic acid (74 mg, 0.56 mmol), potassium carbonate (80 mg, 0.56 mmol) and tetrakis(triphenyl phosphine)palladium(0) (31 mg, 0.027 mmol) were combined in dioxane/water (15 mL, 3:1). The mixture was heated at 100° C. under stirring for 18 hours. The reaction was cooled to room temperature and poured into H₂O. The desired product was extracted with ethyl acetate and the organic layer was separated and washed twice with H₂O, dried over K₂CO₃, and concentrated under reduced vacuum to yield the crude material (236 mg) as a dark oil. The resulting oil was purified via silica gel chromatography employing the Chromatotron using a 4000 micron rotor and eluting with a solvent of hexane/ethyl acetate 7:3 to yield the title compound (107 mg, 81%) as a white solid. Ion spray M.S. 340.0 (M*−1).

Analysis calculated for: $C_{16}H_{20}NO_2S_2F$:

| Theory: | C, 56.28 | H, 5.90 | N, 4.10 |
| Found: | C, 56.24 | H, 5.86 | N, 3.79 |

EXAMPLE 8

Preparation of [2-Fluoro-2-(4-(3-pyridyl)phenyl)propyl][(methylethyl)sulfonyl]amine

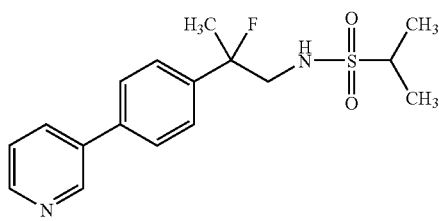

Scheme VI, Step A': [2-fluoro-2-(4-iodophenyl)propyl][(methylethyl)sulfonyl]amine (200 mg, 0.52 mmol, prepared in example 1), pyridyl boronic acid (93 mg, 0.76 mmol), potassium carbonate (104 mg, 0.76 mmol), tetrakis(triphenyl phosphine)palladium(0) (41 mg, 0.036 mmol), and dioxane/water (20 mL, 3:1) were mixed together in a 100 mL single neck flask and stirred at 90° C. over night. In the morning, the reaction was cooled to room temperature and poured into H₂O, and the desired product was extracted with ethyl acetate. The organic layer was backwashed once with H₂O, dried over K₂CO₃, filtered, and concentrated under reduced pressure to yield 235 mg. of a viscous oil. This material was purified via silica gel chromatography employing the Chromatotron and using a 4000 micron rotor while eluting with a solvent of methylene chloride/ethyl acetate 1:1 to yield the title compound (126 mg, 72%) as a semi-solid. Ion spray M.S. 337.2 (M*+1).

Calculated for $C_{17}H_{21}N_2O_2SF$:

| Theory: | C 60.69, | H 6.29, | N 8.33. |
| Found: | C 60.86, | H 6.17, | N 7.99. |

EXAMPLE 9

Preparation of 2-{4-[4-(1-Fluoro-1-methyl-2-{[(methylethyl)sulfonyl]amino}ethyl)phenyl]phenyl}ethanenitrile

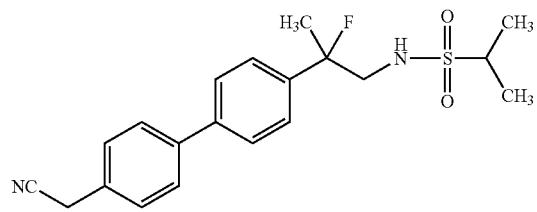

Scheme VI, step A': [2-fluoro-2-(4-iodophenyl)propyl][(methylethyl)sulfonyl]amine (500 mg, 1.3 mmol, prepared in example 1), 4-phenylacetonitrile boronic acid (193 mg, 1.4 mmol), potassium carbonate (193 mg, 1.4 mmol), tetrakis(triphenyl phosphine)palladium(0) (75 mg, 0.65 mmol), dioxane/water (30 mL, 3:1) were mixed together in a 100 mL single neck flask and stirred at 90° C. over night. In the morning, the reaction was cooled to room temperature and poured into H₂O and the desired product was extracted with ethyl acetate. The organic layer was backwashed once with H$_2$O, dried over K$_2$CO$_3$, and concentrated under reduced pressure to yield a viscous oil. This material was purified via silica gel chromatography employing the Chromatotron and using a 2000 micron rotor while eluting with a solvent of hexane/ethyl acetate 7:3 to yield the title compound (143 mg, 30%) as a yellow solid. Material was recrystallized from ethyl acetate-hexane 1:1. M.P. 155°–157° C. Ion spray M.S. 373 (M*–1).

Calculated for C$_{20}$H$_{23}$N$_2$O$_2$SF:

| Theory: | C 64.15, H 6.19, N 7.48. |
|---|---|
| Found: | C 63.91, H 5.96, N 7.37. |

EXAMPLE 10

Preparation of 4-[4-(1-Fluoro-1-methyl-2-{[(methylethyl)sulfonyl]amino}ethyl)phenyl]benzaldehyde

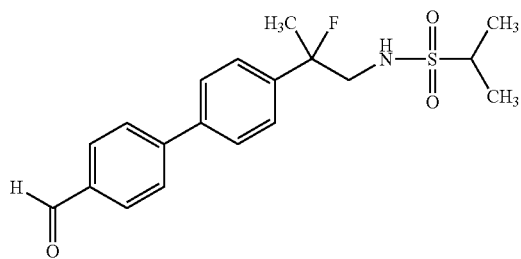

Preparation of 4-[4-(1-Hydroxy-1-methyl-2-{[(methylethyl)sulfonyl]amino}ethyl)phenyl]benzaldehyde

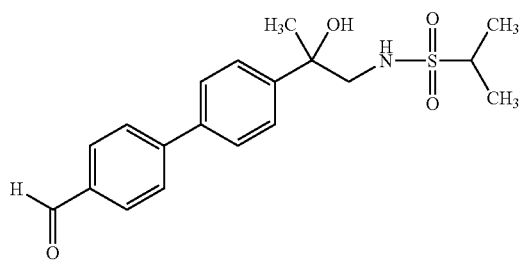

Scheme VI, step A: [2-hydroxy-2-(4-iodophenyl)propyl][(methylethyl)sulfonyl]amine (1.05 g, 2.7 mmol, intermediate prepared in example 1), 4-formylphenyl boronic acid (564 mg, 3.5 mmol), potassium carbonate (483 mg, 3.5 mmol), tetrakis(triphenyl phosphine)palladium(0) (162 mg, 1.4 mmol), and dioxane/water (60 mL, 3:1) were mixed together in a 250 mL single neck flask and stirred at 90° C. over night. In the morning, the reaction was cooled to room temperature and poured into H$_2$O and the desired product was extracted with ethyl acetate. The organic layer was backwashed once with H$_2$O, dried over K$_2$CO$_3$, and concentrated under reduced pressure to yield a viscous oil. This material was purified via silica gel chromatography employing the Chromatotron and using a 2000 micron rotor while eluting with a solvent of hexane/ethyl acetate 1:1 to yield the title compound as a pale yellow solid. This material was recrystallized from ethyl acetate-hexane 1:1 to yield the intermediate title compound (519 mg) as a solid. Ion spray M.S. 360 (M*–1).

Calculated for C$_{19}$H$_{23}$NO$_4$S:

| Theory: | C 63.13, H 6.41, N 3.87. |
|---|---|
| Found: | C 62.94, H 6.29, N 3.82. |

Preparation of Final Title Compound

Scheme VI, step B: Into a 250, 3 neck flask fitted with a stirrer and thermometer, 4-[4-(1-hydroxy-1-methyl-2-{[(methylethyl)sulfonyl]amino}ethyl)phenyl]benzaldehyde (519 mg) in CH$_2$Cl$_2$ (25 mL) was added dropwise to 0.19 mL DAST in CH$_2$Cl$_2$ (35 mL) while stirring at –78° C. under a nitrogen atmosphere. Reaction was allowed to warm to room temperature and diluted with CH$_2$Cl$_2$ (75 mL). This organic layer was washed with H$_2$O, dried over Na$_2$SO$_4$, filtered, and concentrated under reduced vacuum to yield an oil. This two spot material was purified via silica gel chromatography employing the Chromatotron and using a 2000 micron rotor while eluting with a solvent of hexane/ethyl acetate 3:1 to provide the final title compound (0.337 g, 66%, bottom spot) as a white solid. Ion spray M.S. 362 (M*–1).

Calculated for C$_{19}$H$_{22}$NO$_3$SF:

| Theory: | C 62.79, H 6.10, N 3.85. |
|---|---|
| Found: | C 65.22, H 6.13, N 3.21. |

EXAMPLE 11

Preparation of {4-[4-(1-Fluoro-1-methyl-2{[(methylethyl)sulfonyl]amino}ethyl)phenyl]phenyl}-N-methylcarboxamide

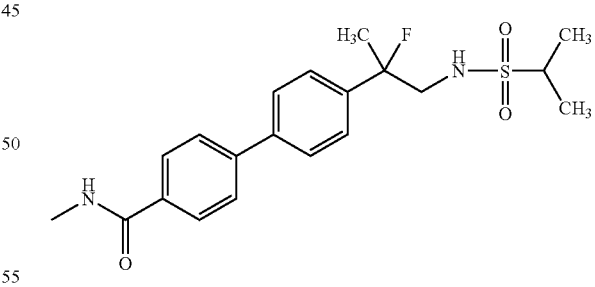

Into a 50 mL single neck flask, 1 mL oxalyl chloride was added syringe wise to 4-[4-(1-fluoro-1-methyl-2-{[(methylethyl)sulfonyl]amino}ethyl)phenyl]benzoic acid (150 mg, 0.40 mmol, prepared in example 4) in CH$_2$Cl$_2$ (10 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into THF (10 mL) and added dropwise to a stirring solution of 40% methylamine in water (5 mL) at room temperature and the mixture was stirred overnight. In the morning, the solution was concentrated under reduced vacuum and the resulting oil was taken into CH$_2$Cl$_2$ and the organic layer was washed once with H$_2$O, dried over K$_2$CO$_3$, and concentrated under reduced vacuum to yield 159 mg as a semi-solid. This material was purified via silica gel chromatography employing the Chromatotron and using a 2000 micron rotor while eluting with a solvent of methylene chloride/ethyl acetate 1:1 to yield the title compound (51 mg, 32%) as a white solid. Ion spray M.S. 393.1 (M*+1).

Calculated for C$_{20}$H$_{25}$N$_2$O$_3$SF:

| Theory: | C 61.21, H 6.42, N 7.14. |
|---|---|
| Found: | C 59.92, H 5.86, N 6.84. |

EXAMPLE 11a

Preparation of {4-[4-(1-Fluoro-1-methyl-2-{[(methylethyl)sulfonyl]amino}ethyl)phenyl]phenyl}-N-methylcarboxamide (Enantiomer 1)

Into a 50 mL single neck flask, 1 mL oxalyl chloride was added syringe wise to (+)-4-[4-(1-fluoro-1-methyl-2-{[(methylethyl)sulfonyl]amino}ethyl)phenyl]benzoic acid (300 mg, 0.79 mmol, prepared in example 1a) in CH$_2$Cl$_2$ (20 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into dioxane (20 mL) and added dropwise to a stirring solution of 40% methylamine (5 mL) at room temperature and the mixture was stirred overnight. In the morning, the solution was concentrated under reduced vacuum and the resulting oil was taken into methylene chloride and the organic layer was washed once with H$_2$O, dried over K$_2$CO$_3$, filtered, and concentrated under reduced vacuum to yield 271 mg as a semi-solid. This material was purified via silica gel chromatography employing the Chromatotron and using a 2000 micron rotor while eluting with a solvent of methylene chloride/ethyl acetate 1:1 to yield the title compound (100 mg, 32%) as a white solid. Ion spray M.S. 391.2 (M*−1).

Calculated for C$_{20}$H$_{25}$N$_2$O$_3$SF—½H$_2$O:

| Theory: | C 59.82, H 6.52, N 6.98. |
|---|---|
| Found: | C 59.69, H 6.29, N 6.81. |

EXAMPLE 11b

Preparation of {4-[4-(1-Fluoro-1-methyl-2-{[(methylethyl)sulfonyl]amino}ethyl)phenyl]phenyl}-N-methylcarboxamide (Enantiomer 2)

Into a 50 mL single neck flask, 1 mL oxalyl chloride was added syringe wise to (−)-4-[4-(1-fluoro-1-methyl-2-{[(methylethyl)sulfonyl]amino}ethyl)phenyl]benzoic acid (300 mg, 0.79 mmol, prepared in example 1a) in methylene chloride (15 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into dioxane (20 mL) and added dropwise to a stirring solution of 40% methylamine (5 mL) at room temperature and the mixture was stirred overnight. In the morning, the solution was concentrated under reduced vacuum and the resulting oil was taken into methylene chloride and the organic layer was washed once with H$_2$O, dried over K$_2$CO$_3$, filtered, and concentrated under reduced vacuum to yield 391 mg as a solid. This material was purified via recrystallization from hexane/ethyl acetate 1:1 to yield the title compound (231 mg, 49%) as a white solid. Ion spray M.S. 391.4 (M*−1).

Calculated for C$_{20}$H$_{25}$N$_2$O$_3$SF—½H$_2$O:

| Theory: | C 59.82, H 6.52, N 6.98. |
|---|---|
| Found: | C 59.78, H 6.53, N 6.89. |

EXAMPLE 12

Preparation of {4-[4-(1-Fluoro-1-methyl-2-{[(methylethyl)sulfonyl]amino}ethyl)phenyl]phenyl}-N,N-dimethylcarboxamide

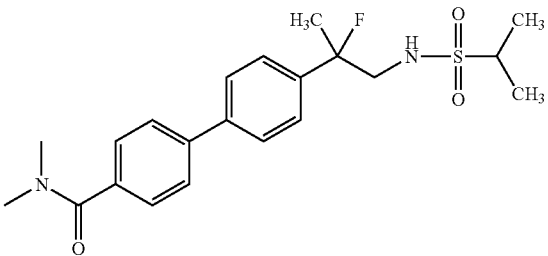

Into a 50 mL single neck flask, 1 mL oxalyl chloride was added syringe wise to 4-[4-(1-fluoro-1-methyl-2-{[(methylethyl)sulfonyl]amino}ethyl)phenyl]benzoic acid (150 mg, 0.40 mmol, prepared in example 4) in CH$_2$Cl$_2$ (10 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into THF (10 mL) and added dropwise to a stirring solution of 40% dimethylamine in water (5 mL) at room temperature and the mixture was stirred overnight. In the morning, the solution was concentrated under reduced vacuum and the resulting oil was taken into CH$_2$Cl$_2$ and the organic layer was washed once with H$_2$O, dried over K$_2$CO$_3$, and concentrated under reduced vacuum to yield 167 mg as an oil. This material was purified via silica gel chromatography employing the Chromatotron and using a 2000 micron rotor while eluting with a solvent of methylene chloride/ethyl acetate 1:1 to yield the title compound (97 mg, 60%) as a viscous oil. Ion spray M.S. 407.4 (M*+1).

Calculated for $C_{21}H_{27}N_2O_3SF$:

| Theory: | C 62.05, H 6.70, N 6.89. |
|---|---|
| Found: | C 61.32, H 6.69, N 6.85. |

EXAMPLE 13

Preparation of N-ethyl{4-[4-(1-Fluoro-1-methyl-2-{[(methylethyl)sulfonyl]amino}ethyl)phenyl]phenyl}carboxamide

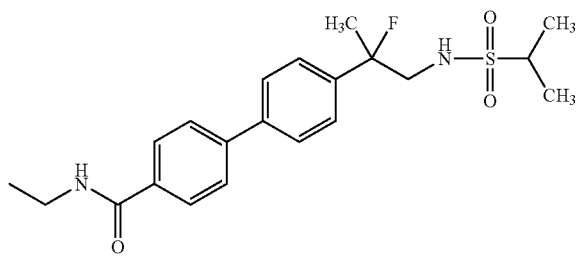

Into a 50 mL single neck flask, 1 mL oxalyl chloride was added syringe wise to 4-[4-(1-fluoro-1-methyl-2-{[(methylethyl)sulfonyl]amino}ethyl)phenyl]benzoic acid (140 mg, 0.37 mmol, prepared in example 4) in $CH_2Cl_2$ (10 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into THF (10 mL) and added dropwise to a stirring solution of 2.0 M ethylamine in THF (0.5 mL) at room temperature and the mixture was stirred overnight. In the morning, the solution was concentrated under reduced vacuum and the resulting oil was taken into $CH_2Cl_2$ and the organic layer was washed once with $H_2O$, dried over $K_2CO_3$, and concentrated under reduced vacuum to yield 151 mg as an oil. This material was purified via silica gel chromatography employing the Chromatotron and using a 2000 micron rotor while eluting with a solvent of methylene chloride/ethyl acetate 1:1 to yield the title compound (127 mg, 85%) as a viscous oil. Ion spray M.S. 407.4 (M*+1).

EXAMPLE 14

Preparation of 4-[4-(1-Fluoro-1-methyl-2-{[(methylethyl)sulfonyl]amino}ethyl)phenyl]phenyl Pyrrolidinyl Ketone

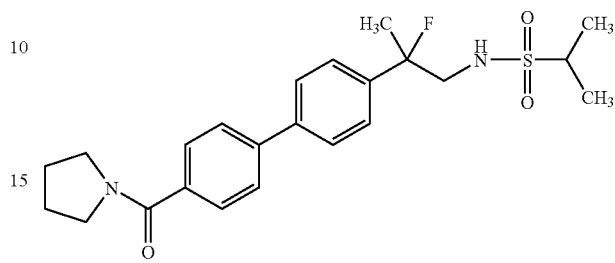

Into a 50 mL single neck flask, 1 mL oxalyl chloride was added syringe wise to 4-[4-(1-fluoro-1-methyl-2-{[(methylethyl)sulfonyl]amino}ethyl)phenyl]benzoic acid (200 mg, 0.53 mmol, prepared in example 4) in $CH_2Cl_2$ (15 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into THF (10 mL) and added dropwise to a stirring solution of 94 mg pyrolline in THF (10 mL) at room temperature and the mixture was stirred overnight. In the morning, the solution was concentrated under reduced vacuum and the resulting oil was taken into $CH_2Cl_2$ and the organic layer was washed once with $H_2O$, dried over $K_2CO_3$, and concentrated under reduced vacuum to yield 271 mg as an oil. This material was purified via silica gel chromatography employing the Chromatotron and using a 4000 micron rotor while eluting with a solvent of hexane/ethyl acetate 7:3 to yield the title compound (141 mg, 62%) as a viscous oil. Ion spray M.S. 433.3 (M*+1).

Calculated for $C_{23}H_{29}N_2O_3SF$:

| Theory: | C 63.86, H 6.76, N 6.48. |
|---|---|
| Found: | C 62.93, H 6.40, N 5.95. |

EXAMPLE 15

Preparation of N-{3-[4-(1-Fluoro-1-methyl-2-{[(methylethyl)sulfonyl]amino}ethyl)phenyl]phenyl}acetamide

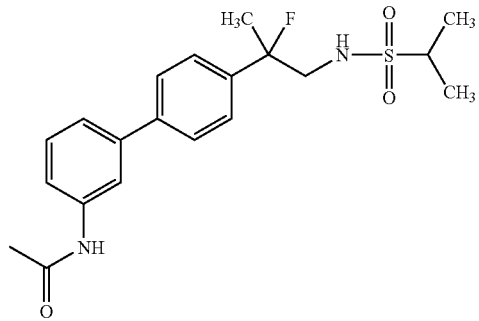

Into a 100 mL single-neck flask, 49 mg of acetyl chloride was added dropwise to 200 mg of {2-[4-(3-aminophenyl)phenyl]-2-fluoropropyl}[(methylethyl)sulfonyl]amine (prepared in example 5) and 63 mg of triethylamine in THF (25 mL) while stirring under a nitrogen atmosphere at room temperature. The reaction was allowed to stir at this temperature for 2 h. The mixture was then poured into H$_2$O and the desired product was extracted into ethyl acetate. The organic layer was backwashed once with H$_2$O, dried over K$_2$CO$_3$, and concentrated under reduced vacuum to yield 193 mg as a foam. This material was purified via silica gel chromatography employing the Chromatotron, using a 4000 micron rotor and eluting with a solvent of hexane/ethyl acetate 1:1 to yield the title compound (121 mg, 54%) as a white foam. Ion spray M.S. 391.2 (M*-1).

Calculated for: C$_{20}$H$_{25}$N$_2$O$_3$SF:

| | |
|---|---|
| Theory: | C 61.20, H 6.42, N 7.13. |
| Found: | C 60.28, H 6.40, N 6.76. |

EXAMPLE 16

Preparation of N-{3-[4-(1-Fluoro-1-methyl-2-{[(methylethyl)sulfonyl]amino}ethyl)phenyl]phenyl}propanamide

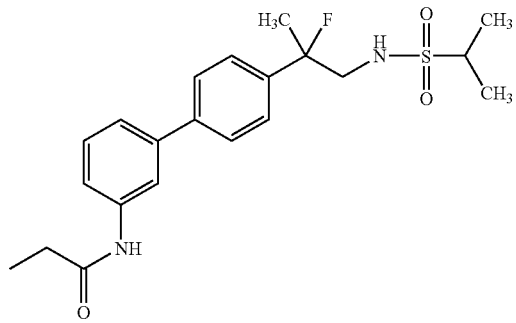

Into a 100 mL single-neck flask, 58 mg of propynyl chloride was added dropwise to 200 mg of {2-[4-(3-aminophenyl)phenyl]-2-fluoropropyl}[(methylethyl)sulfonyl]amine (prepared in example 5) and 63 mg of triethylamine in THF (25 mL) while stirring under a nitrogen atmosphere at room temperature. The reaction was allowed to stir at this temperature for 2 h. The mixture was then poured into H$_2$O and the desired product was extracted into ethyl acetate. The organic layer was backwashed once with H$_2$O, dried over K$_2$CO$_3$, and concentrated under reduced vacuum to yield 256 mg as a foam. This material was purified via silica gel chromatography employing the Chromatotron, using a 4000 micron rotor and eluting with a solvent of hexane/ethyl acetate 1:1 to yield the title compound (130 mg, 56%) as a white foam. Ion spray M.S. 405.5 (M*-1).

Calculated for: C$_{21}$H$_{27}$N$_2$O$_3$SF—½H$_2$O:

| | |
|---|---|
| Theory: | C 60.69, H 6.79, N 6.74. |
| Found: | C 60.95, H 6.49, N 6.77. |

EXAMPLE 17

Preparation of N-{3-[4-(1-Fluoro-1-methyl-2-{[(methylethyl)sulfonyl]amino}ethyl)phenyl]phenyl}butanamide

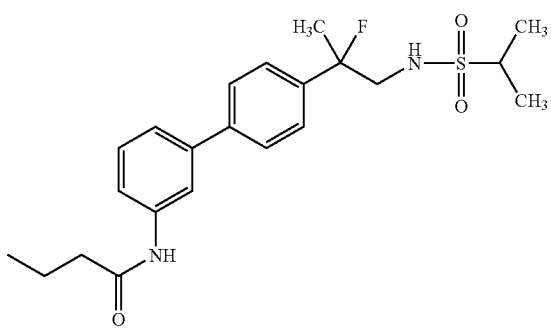

Into a 100 mL single-neck flask, 71 mg of butyryl chloride was added dropwise to 200 mg {2-[4-(3-aminophenyl)phenyl]-2-fluoropropyl}[(methylethyl)sulfonyl]amine (prepared in example 5) and 63 mg of triethylamine in THF (25 mL) while stirring under a nitrogen atmosphere at room temperature. The reaction was allowed to stir at this temperature for 2 h. The mixture was then poured into H$_2$O and the desired product was extracted into ethyl acetate. The organic layer was backwashed once with H$_2$O, dried over K$_2$CO$_3$, and concentrated under reduced vacuum to yield 211 mg as an oil. This material was purified via silica gel chromatography employing the Chromatotron, using a 4000 micron rotor and eluting with a solvent of hexane/ethyl acetate 1:1 to yield the title compound (130 mg, 54%) as a white foam. Ion spray M.S. 419.2 (M*-1).

Calculated for: C$_{22}$H$_{29}$N$_2$O$_3$SF:

| | |
|---|---|
| Theory: | C 62.83, H 6.95, N 6.66. |
| Found: | C 62.49, H 6.84, N 6.60. |

EXAMPLE 18

Preparation of Amino-N-{3-[4-(1-fluoro-1-methyl-2-{[(methylethyl)sulfonyl]amino}ethyl)phenyl]phenyl}amide

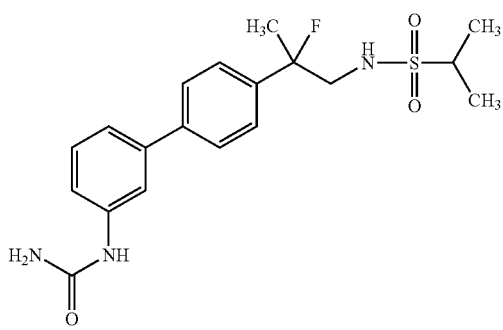

Into a 100-single neck flask, 0.1 mL of TFA in toluene (5 mL) was added dropwise to 200 mg {2-[4-(3-aminophenyl)phenyl]-2-fluoropropyl}[(methylethyl)sulfonyl]amine (prepared in example 5) and 56 mg of sodium cyanate in toluene (15 mL) while stirring under a nitrogen atmosphere at 45°–50° C. The reaction was then heated to 80° C. for 1 h. The solution was cooled to room temperature and concentrated under reduced vacuum to yield a solid. This TFA salt was liberated with 1N NaOH and the desired product was extracted into methylene chloride. The organic layer was backwashed once with H$_2$O, dried over K$_2$CO$_3$, and concentrated under reduced vacuum to yield 168 mg as a foam. This material was purified via silica gel chromatography employing the Chromatotron, using a 4000 micron rotor and eluting with a solvent of hexane/ethyl acetate 1:9 to yield the title compound (77 mg, 34%) as a yellow foam. Ion spray M.S. 392.2 (M*–1).

Calculated for: C$_{19}$H$_{24}$N$_3$O$_3$SF—H$_2$O:

| Theory: | C 55.45, H 6.37, N 10.21. |
|---|---|
| Found: | C 55.82, H 6.02, N 9.91. |

EXAMPLE 19

Preparation of N-[4-(1-Fluoro-1-methyl-2-{[(methylethyl)sulfonyl]amino}ethyl)phenyl]benzamide

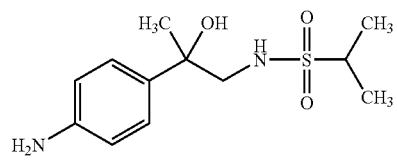

Preparation of [2-Hydroxy-2-(4-nitrophenyl)propyl][(methylethyl)sulfonyl]amine

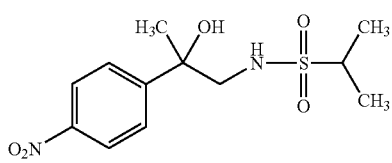

In a 500 mL, 3 neck flask fitted with a stirrer and thermometer, 2.98 g. of propanesulfonyl chloride was added dropwise to 3.92 g. of 2-hydroxy-2-(4-nitrophenyl)propylamine and 3.19 g. of DBU in CH$_2$Cl$_2$ (200 mL) while stirring at 0° C. under a nitrogen atmosphere. The reaction was allowed to warm to room temperature and stirred overnight at this temperature. In the morning, reaction was diluted with CH$_2$Cl$_2$ (100 mL) and the organic layer was washed two times with H$_2$O, dried over Na$_2$SO$_4$, and concentrated under reduced vacuum to yield a viscous oil. This material was purified via silica gel chromatography employing the Water's Prep 2000 and eluting with a solvent of hexane/ethyl acetate 1:1 to yield the intermediate title compound (940 mg, 16%) as a viscous oil. Ion spray M.S. 302.1 (M*–1).

Preparation of [2-(4-Aminophenyl)-2-hydroxypropyl][(methylethyl)sulfonyl]amine

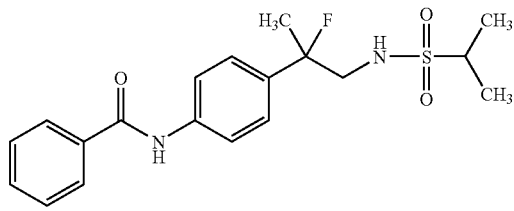

900 mg of [2-hydroxy-2-(4-nitrophenyl)propyl][(methylethyl)sulfonyl]amine and 1.2 equivalence of 10% Pd/C in ethyl acetate (50 mL) were subjected to a hydrogen atmosphere while shaking at 60 psi for 3 hours. Solution was filtered through a Celite® mat and the resulting filtrate was concentrated under reduced vacuum to yield 720 mg as an oil. This material was purified via silica gel chromatography employing the Chromatotron and using a 4000 micron rotor while eluting with a solvent of hexane/ethyl acetate 1:1 to yield the intermediate title compound (340 mg, 42%) as a tan solid. Ion spray M.S. 271.4 (M*–1).

Calculated for C$_{12}$H$_{20}$N$_2$O$_3$S:

| Theory: | C 52.92, | H 7.40, | N 10.29 |
|---|---|---|---|
| Found: | C 53.26, | H 7.40, | N 10.11 |

Preparation of N-[4-(1-Hydroxy-1-methyl-2-{[(methylethyl)sulfonyl]amino}ethyl)phenyl]benzamide

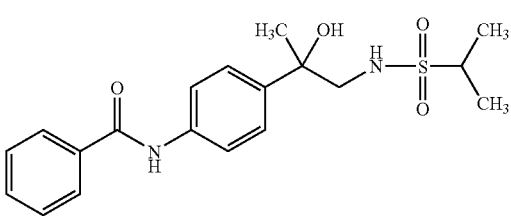

Scheme XII, Step A: Into a 100 mL single-neck flask, 77 mg of benzoyl chloride was added dropwise to 135 mg of [2-(4-aminophenyl)-2-hydroxypropyl][(methylethyl)sulfonyl]amine and 56 mg of triethylamine in THF (20 mL) while stirring under a nitrogen atmosphere at room temperature. The reaction was allowed to stir at this temperature for 2 h. The mixture was then poured into H$_2$O and the desired product was extracted into ethyl acetate. The organic layer was backwashed once with H$_2$O, dried over K$_2$CO$_3$, and concentrated under reduced vacuum to yield 233 mg as a solid. This material was purified via silica gel chromatography employing the Chromatotron, using a 2000 micron rotor and eluting with a solvent of ethyl acetate to yield the intermediate title compound (151 mg, 80%) as a white solid. Ion spray M.S. 375.2 (M*–1).

Preparation of Final Title Compound

Scheme XII, Step B: Into a 50 mL 3 neck flask fitted with a stirrer and thermometer, 130 mg of N-[4-(1-hydroxy-1-methyl-2-{[(methylethyl)sulfonyl]amino}ethyl)phenyl]benzamide in methylene chloride (5 mL) was added dropwise to 62 mg of DAST in methylene chloride (5 mL) while stirring at −78° C. under a nitrogen atmosphere. Reaction was allowed to warm to room temperature and diluted with methylene chloride (25 mL). This organic layer was washed with $H_2O$, dried over $Na_2SO_4$, and concentrated under reduced vacuum to yield 136 mg as a white foam. This material was purified via silica gel chromatography employing the Chromatotron and using a 2000 micron rotor while eluting with a solvent of hexane/ethyl acetate 1:1 to yield the final title compound (79 mg, 60%) as a white solid. Yield=60%. Ion spray M.S. 377.4 (M*−1).

Calculated for $C_{19}H_{23}N_2O_3SF$:

| Theory: | C 60.30, | H 6.13, | N 7.31. |
|---|---|---|---|
| Found: | C 60.20, | H 6.05, | N 7.30. |

EXAMPLE 20

Preparation of (3-Cyanophenyl)-N-[4-(1-fluoro-1-methyl-2-{[(methylethyl)sulfonyl]amino}ethyl)phenyl]carboxamide

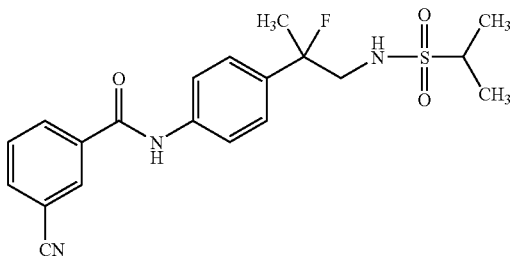

Preparation of (3-Cyanophenyl)-N-[4-(1-hydroxy-1-methyl-2-{[(methylethyl)sulfonyl]amino}ethyl)phenyl]carboxamide

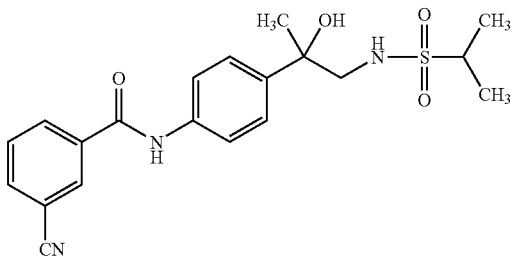

Scheme XII, Step A: Into a 100 mL single-neck flask, 91 mg of 3-cyanobenzoyl chloride was added dropwise to 135 mg of [2-(4-aminophenyl)-2-hydroxypropyl][(methylethyl)sulfonyl]amine (prepared in example 19) and 56 mg of triethylamine in THF (20 mL) while stirring under a nitrogen atmosphere at room temperature. The reaction was allowed to stir at this temperature for 2 h. The mixture was then poured into $H_2O$ and the desired product was extracted into ethyl acetate. The organic layer was backwashed once with $H_2O$, dried over $K_2CO_3$, and concentrated under reduced vacuum to yield 254 mg as a solid. This material was purified via silica gel chromatography employing the Chromatotron, using a 2000 micron rotor and eluting with a solvent of ethyl acetate to yield the intermediate title compound (131 mg, 66%) as an oil. Ion spray M.S. 400.1 (M*−1).

Calculated for: $C_{20}H_{23}N_3O_4S$:

| Theory: | C 59.83, | H 5.77, | N 10.47. |
|---|---|---|---|
| Found: | C 61.33, | H 5.64, | N 10.19. |

Preparation of Final Title Compound

Scheme XII, Step B: Into a 50 mL 3 neck flask fitted with a stirrer and thermometer, 110 mg of (3-cyanophenyl)-N-[4-(1-hydroxy-1-methyl-2-{[(methylethyl)sulfonyl]amino}ethyl)phenyl]carboxamide in methylene chloride (5 mL) was added dropwise to 48 mg of DAST in methylene chloride (5 mL) while stirring at −78° C. under a nitrogen atmosphere. Reaction was allowed to warm to room temperature and diluted with methylene chloride (25 mL). This organic layer was washed with $H_2O$, dried over $Na_2SO_4$, and concentrated under reduced vacuum to yield 110 mg as a tan solid. This material was purified via silica gel chromatography employing the Chromatotron and using a 2000 micron rotor while eluting with a solvent of hexane/ethyl acetate 1:1 to yield the final title compound (62 mg, 62%) as a yellow solid. Ion spray M.S. 402.2 (M*−1).

Calculated for $C_{20}H_{22}N_3O_3SF$: Theory: C, 59.54; H, 5.49; N, 10.41. Found: C, 58.74; H, 5.29; N, 10.03.

EXAMPLE 21

Preparation of N-[4-(1-Fluoro-1-methyl-2-{[(methylethyl)sulfonyl]amino}ethyl)phenyl]-4-pyridylcarboxamide

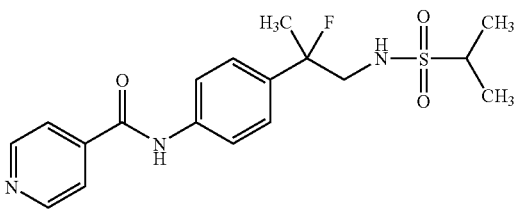

57

Preparation of N-[4-(1-Hydroxy-1-methyl-2-{[(methylethyl)sulfonyl]amino}ethyl)phenyl]-4-pyridyl-carboxamide

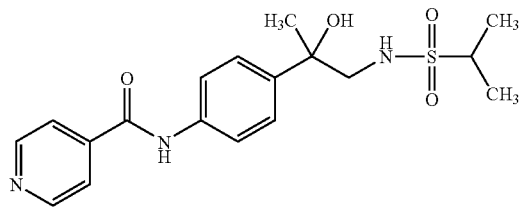

Scheme XII, Step A: [2-(4-aminophenyl)-2-hydroxypropyl][(methylethyl)sulfonyl]amine (350 mg, 1.3 mmol, prepared in example 19), isonicotinic acid (176 mg, 1 mmol), triethylamine (333 mg, 3.3 mmol), 4-dimethylamino pyridine (12.2 mg, DMAP), and 1-[3-(dimethylamino)propyl]-3-ethylcarbodiimide HCl (298 mg, 1.6 mmol, DCC) were mixed together with methylene chloride (15 mL) in a 50 mL single neck flask and stirred under a nitrogen atmosphere at room temperature for 64 hours. The solution was then poured into $H_2O$, and the desired product was extracted with ethyl acetate. The organic layer was backwashed once with $H_2O$, dried over $K_2CO_3$, and concentrated under reduced vacuum to yield 471 mg as an oil. This material was purified via silica gel chromatography employing the Chromatotron, using a 4000 micron rotor and eluting with a solvent of methylene chloride/methanol 19:1 to yield the intermediate title compound (131 mg, 27%) as an oil. Ion spray M.S. 378.5 (M*+1).

Calculated for: $C_{18}H_{23}N_3O_4S$:

| Theory: | C 57.27, | H 6.14, | N 11.13. |
| --- | --- | --- | --- |
| Found: | C 57.75, | H 5.97, | N 11.05. |

Preparation of Final Title Compound

Scheme XII, Step B: Into a 50 mL 3 neck flask fitted with a stirrer and thermometer, 80 mg of N-[4-(1-hydroxy-1-methyl-2-{[(methylethyl)sulfonyl]amino}ethyl)phenyl]-4-pyridylcarboxamide in methylene chloride (5 mL) was added dropwise to 0.1 mL of DAST in methylene chloride (5 mL) while stirring at −78° C. under a nitrogen atmosphere. Reaction was allowed to warm to room temperature and diluted with methylene chloride (25 mL). This organic layer was washed with $H_2O$, dried over $Na_2SO_4$, and concentrated under reduced vacuum to yield 62.2 mg as a yellow solid. This material was purified via silica gel chromatography employing the Chromatotron and using a 1000 micron rotor while eluting with a solvent of ethyl acetate to yield the final title compound (32 mg, 40%) as a pale yellow solid. Ion spray M.S. 380.4 (M*+1).

58

Calculated for $C_{18}H_{22}N_3O_3SF$—½$H_2O$:

| Theory: | C 55.56, | H 5.96, | N 10.81. |
| --- | --- | --- | --- |
| Found: | C 55.40, | H 5.73, | N 10.41. |

EXAMPLE 22

Preparation of N-[4-(1-Fluoro-1-methyl-2-{[(methylethyl)sulfonyl]amino}ethyl)phenyl]{4-[2-(methoxycarbonylamino)ethyl]phenyl}carboxamide

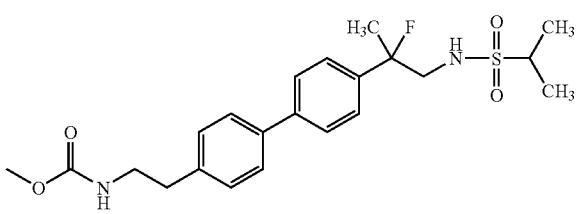

Preparation of N-[2-(4-Bromophenyl)ethyl]methoxycarboxamide

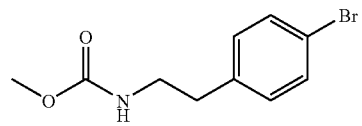

Into a 50 mL-single neck flask, 260 mg of methyl chloroformate in acetone (5 mL) was added dropwise to 500 mg of 4-bromophenethyl amine and 291 mg of $Na_2CO_3$ in acetone (20 mL) while stirring at room temperature under a nitrogen atmosphere. The reaction was then stirred overnight at this temperature. In the morning, the mixture was poured into $H_2O$ and the desired product was extracted with ethyl acetate. This organic layer was washed with $H_2O$, dried over $Na_2SO_4$, and concentrated under reduced vacuum to yield the intermediate title compound (714 mg) as a white solid. This material was taken to the next reaction without further purification. Ion spray M.S. 259.2 (M*+1).

Preparation of Final Title Compound

Into a 100 mL-single neck flask, 285 mg of [2-fluoro-2-(4-iodophenyl)propyl][(methylethyl)sulfonyl]amine (prepared in example 1), 200 mg of 4,4,5,5-tetramethyl-1,2,3-dioxaborolane (Dibron), and 215 mg of potassium acetate in DMF (15 mL) was stirred and degassed with argon for 10 minutes. Then, 15 mg of $PdCl_2$(dppf) was added portion wise and the reaction was stirred at 80° C. under a nitrogen atmosphere for 2 hours. The reaction was then cooled to room temperature and 3.40 mg of N-[2-(4-bromophenyl)ethyl]methoxycarboxamide, 1.80 mL $Na_2SO_3/H_2O$, and an additional 15 mg of $PdCl_2$(dppf) was added all portion wise and the mixture was then heated to 80° C. and stirred overnight. In the morning, the mixture was cooled to room temperature and poured into $H_2O$ and the desired product was extracted with ethyl acetate. This organic layer was washed with H$_2$O, dried over Na$_2$SO$_4$, and concentrated under reduced vacuum to yield 616 mg of a dark oil. This two spot material was purified via silica gel chromatography employing the Chromatotron and using a 4000 micron rotor while eluting with a solvent of methylene chloride/ethyl acetate 9:1. Collection of the bottom spot provided the final title compound (55 mg, 17%) as a slowly crystallizing oil. Ion spray M.S. 435.3 (M*−1).

Calculated for: C$_{22}$H$_{29}$N$_2$O$_4$SF:

| Theory: | C 60.53, | H 6.70, | N 6.42. |
|---|---|---|---|
| Found: | C 60.52, | H 6.77, | N 6.06. |

EXAMPLE 23

Preparation of (2-{4-[(3,5-Difluorophenyl)methoxy] phenyl}-2-fluoropropyl)[(methylethyl)sulfonyl] amine

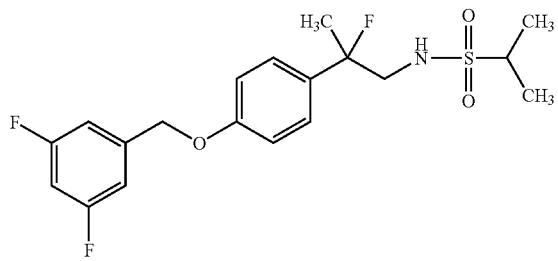

Preparation of [2-Hydroxy-2-(4-hydroxyphenyl) propyl][(methylethyl)sulfonyl]amine

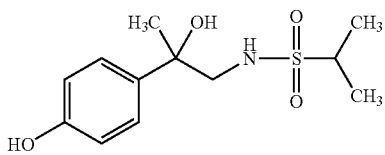

Into a 50 mL-3 neck flask fitted with a stirrer and thermometer was placed 1.0 gm. Of [2-(4-aminophenyl)-2-hydroxypropyl][(methylethyl)sulfonyl]amine (prepared in example 19) and 4.06 gm of 48% HBF$_4$ in H$_2$O (20 mL) at 0° C. The reaction was then stirred at this temperature for 30 minutes. 0.26 gm of sodium nitrite was then added portion wise to the mixture and stirring at this temperature continued for an additional 30 minutes. The reaction was then slowly heated to 70° C. and stirred at this temperature for 3 hours. The mixture was cooled to room temperature and the solution was taken to pH 12 with 1 N NaOH and the solution was filtered. The filtrate was the taken to pH 3.0 with 1 N HCl and the desired product was extracted into ethyl acetate. The organic layer was dried over Na$_2$SO$_4$, and concentrated under reduced vacuum to yield 1.20 gm of a dark oil. This two spot material was purified via silica gel chromatography employing the Chromatotron and using a 4000 micron rotor while eluting with a solvent of methylene chloride/ethyl acetate 9:1. Collection of the bottom spot provided the intermediate title compound (200 mg, 20%) as a slowly crystallizing oil. Ion spray M.S. 272.4 (M*−1).

Preparation of (2-{4-[(3,5-Difluorophenyl)methoxy] phenyl}-2-hydroxypropyl)[(methylethyl)sulfonyl] amine

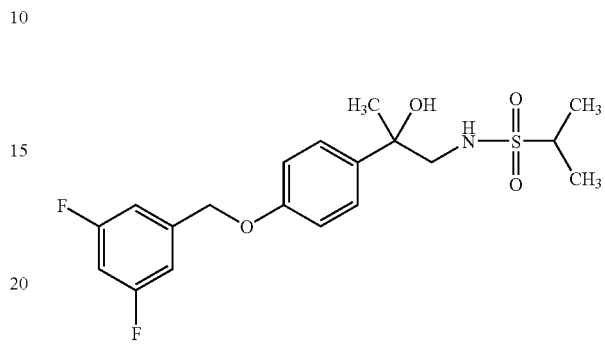

Scheme XI, Step A: Into a 100 mL-3 neck flask fitted with a stirrer and thermometer, 200 mg of [2-hydroxy-2-(4-hydroxyphenyl)propyl][(methylethyl)sulfonyl]amine in DMF (5 mL) was added dropwise to 35 mg of NaH in DMF (20 mL) while stirring at room temperature under a nitrogen atmosphere. After stirring at this temperature for 30 minutes, 153 mg of 3,5-difluorobenzyl bromide in DMF (5 mL) was added dropwise followed by the addition of 92 mg of NaI portion wise. The reaction was then heated at 100° C. for 2 hours. The mixture was cooled to room temperature and poured into H$_2$O and the desired product was extracted with ethyl acetate. This organic layer was washed with H$_2$O, dried over K$_2$CO$_3$, and concentrated under reduced vacuum to yield 410 mg of a brown oil. This two spot material was purified via silica gel chromatography employing the Chromatotron and using a 4000 micron rotor while eluting with a solvent of hexane/ethyl acetate 1:1. Collection of the bottom spot provided the intermediate title compound (70 mg, 24%) as an oil. Ion spray M.S. 398.1 (M*−1).

Preparation of Final Title Compound

Scheme XI, Step B: Into a 25-3 neck flask fitted with a stirrer and thermometer, 70 mg of (2-{4-[(3,5-difluorophenyl)methoxy]phenyl}-2 -hydroxypropyl)[(methylethyl)sulfonyl]amine in methylene chloride (5 mL) was added dropwise to 0.1 mL DAST in methylene chloride (5 mL) while stirring at −78° C. under a nitrogen atmosphere. The reaction was allowed to warm to room temperature and diluted with methylene chloride (25 mL). This organic layer was washed with H$_2$O, dried over Na$_2$SO$_4$, and concentrated under reduced vacuum to yield 64 mg of an oil. This material was purified via silica gel chromatography employing the Chromatotron and using a 1000 micron rotor while eluting with a solvent of hexane/ethyl acetate 1:1 to provide the final title compound (45 mg, 63%) as an orange oil. Ion spray M.S. 401.3 (M*).

EXAMPLE 24

Preparation of {2-Fluoro-2-[4-(4-{2-[(methylsulfonyl)amino]ethyl}phenyl)phenyl]propyl}[(methylethyl)sulfonyl]amine

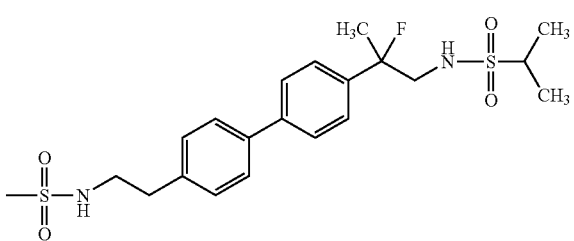

Preparation of {2-Hydroxy-2-[4-(4-{2-[(methylsulfonyl)amino]ethyl}phenyl)phenyl]propyl}[(methylethyl)sulfonyl]amine

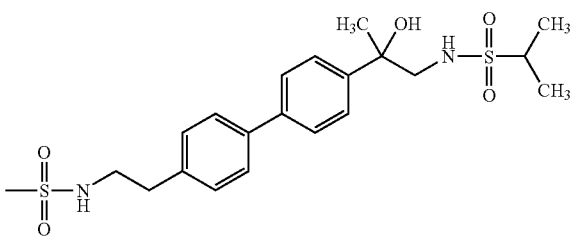

Scheme VI, Step A: [2-hydroxy-2-(4-iodophenyl)propyl][(methylethyl)sulfonyl]amine (383 mg, 100 mmol, intermediate prepared in example 1), BOC-4-(ethyl)methyl-phenyl boronic acid (688 mg, 200 mmol), potassium carbonate (276 mg, 200 mmol), tetrakis(triphenyl phosphine)palladium(0) (58 mg, 0.05 mmol), and dioxane/water (60 mL, 3:1) were mixed together in a 250 mL single neck flask and stirred at 90° C. over night. In the morning, the reaction was cooled to room temperature and poured into H$_2$O and the desired product was extracted with ethyl acetate. The organic layer was backwashed once with H$_2$O, dried over K$_2$CO$_3$, and concentrated under reduced pressure to yield a 3 spot material as a viscous oil. This material was purified via silica gel chromatography employing the Chromatotron and using a 4000 micron rotor while eluting with a solvent of hexane/ethyl acetate 7:3 to yield the intermediate title compound (383 mg, 72%, bottom spot) as an oil. Ion spray M.S. 453 (M*–1).

Calculated for $C_{21}H_{30}N_2O_5S_2$:

| Theory: | C 55.48, | H 6.65, | N 6.16. |
|---|---|---|---|
| Found: | C 55.11, | H 6.48, | N 6.04. |

Preparation of Final Title Compound

Scheme VI, Step B: Into a 50-3 neck flask fitted with a stirrer and thermometer, 383 mg of {2-hydroxy-2-[4-(4-{2-[(methylsulfonyl)amino]ethyl}phenyl)phenyl]propyl}[(methylethyl)sulfonyl]amine in methylene chloride (5 mL) was added dropwise to 0.1 mL DAST in methylene chloride (20 mL) while stirring at –78° C. under a nitrogen atmosphere. The reaction was allowed to warm to room temperature and diluted with methylene chloride (50 mL). This organic layer was washed with H$_2$O, dried over Na$_2$SO$_4$, and concentrated under reduced vacuum to yield an oil. This material was purified via silica gel chromatography employing the Chromatotron and using a 2000 micron rotor while eluting with a solvent of hexane/ethyl acetate 1:1 to yield the final title compound (228 mg, 56%) as an oil. Ion spray M.S. 455 (M*–1).

Calculated for $C_{21}H_{29}N_2O_4S_2F$:

| Theory: | C 55.24, | H 6.41, | N 6.13. |
|---|---|---|---|
| Found: | C 55.05, | H 6.41, | N 6.10. |

EXAMPLE 25

Preparation of (4-Chlorophenyl)-N-[4-(1-fluoro-1-methyl-2-{[(methylethyl)sulfonyl]amino}ethyl)phenyl]carboxamide

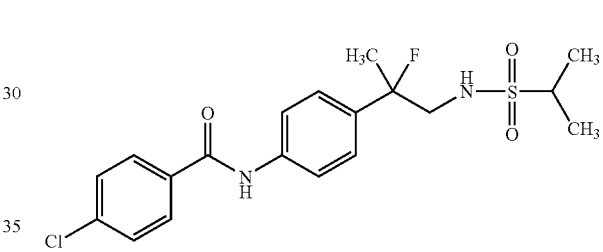

Preparation of (4-Chlorophenyl)-N-[4-(1-hydroxy-1-methyl-2-{[(methylethyl)sulfonyl]amino}ethyl)phenyl]carboxamide

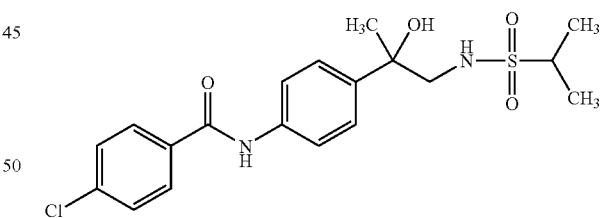

Scheme XII, Step A: Into a 100 mL single-neck flask, 142 mg of 4-chlorobenzoyl chloride was added dropwise to 200 mg of [2-(4-aminophenyl)-2-hydroxypropyl][(methylethyl)sulfonyl]amine (prepared in example 19) and 83 mg of triethylamine in THF (25 mL) while stirring under a nitrogen atmosphere at room temperature. The reaction was allowed to stir at this temperature for 2 h. The mixture was then poured into H$_2$O and the desired product was extracted into ethyl acetate. The organic layer was backwashed once with H$_2$O, dried over K$_2$CO$_3$, and concentrated under reduced vacuum to yield 310 mg as a white solid. This material was purified via recrystallization from hexane-ethyl acetate 1:1 to yield intermediate title compound (165 mg, 54%) as a white solid. Ion spray M.S. 409.2 (M*31 1).

Calculated for C$_{19}$ H$_{23}$ N$_2$ O$_4$ S Cl:

| Theory: | C 55.53, | H 5.64, | N 6.82. |
|---|---|---|---|
| Found: | C 55.33, | H 5.47, | N 6.75. |

Preparation of Final Title Compound

Scheme XII, Step B: Into a 25 mL 3 neck flask fitted with a stirrer and thermometer, 100 mg of (4-chlorophenyl)-N-[4-(1-hydroxy-1-methyl-2-{[(methylethyl)sulfonyl]amino}ethyl)phenyl]carboxamide in CH$_2$Cl$_2$ (5 mL) was added dropwise to 0.03 mL DAST in CH$_2$CL$_2$ (5 mL) while stirring at –78° C. under a nitrogen atmosphere. Reaction was allowed to warm to room temperature and diluted with CH$_2$Cl$_2$ (25 mL). This organic layer was washed with H$_2$O, dried over Na$_2$SO$_4$, and concentrated under reduced vacuum to yield 108 mg as a foam. This material was triturated in hexane/ethyl acetate 19:1 for ½ h and then filtered to yield the final title compound (90 mg, 87%) as a tan solid. Ion spray M.S. 413.1 (M*).

Calculated for: C$_{19}$H$_{22}$N$_2$O$_3$SFCl—½H$_2$O:

| Theory: | C 54.08, | H 5.49, | N 6.64. |
|---|---|---|---|
| Found: | C 53.91, | H 5.28, | N 6.75. |

EXAMPLE 26

Preparation of (6-Chloro(3-pyridyl))-N-[4-(1-fluoro-1-methyl-2-{[(methylethyl)sulfonyl]amino}ethyl)phenyl]carboxamide

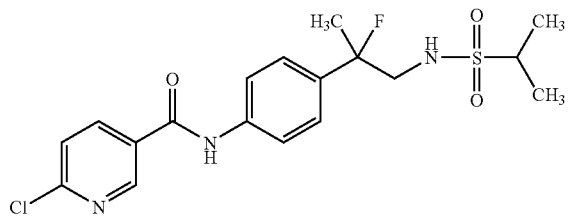

Preparation of (6-Chloro(3-pyridyl))-N-[4-(1-hydroxy-1-methyl-2-{[(methylethyl)sulfonyl]amino}ethyl)phenyl]carboxamide

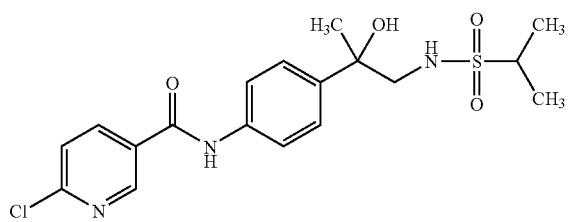

Scheme XII, Step A: Into a 100 mL single-neck flask, 142 mg of 6-chloronicotinoyl chloride was added dropwise to 200 mg of [2-(4-aminophenyl)-2-hydroxypropyl][(methylethyl)sulfonyl]amine (prepared in example 19) and 83 mg of triethylamine in THF (25 mL) while stirring under a nitrogen atmosphere at room temperature. The reaction was allowed to stir at this temperature for 2 h. The mixture was then poured into H$_2$O and the desired product was extracted into ethyl acetate. The organic layer was backwashed once with H$_2$O, dried over K$_2$CO$_3$, and concentrated under reduced vacuum to yield 294 mg as a white solid. This material was purified via recrystallization from ethyl acetate to yield the intermediate title compound (161 mg, 53%) as a white solid. Ion spray M.S. 412.1 (M*–1).

Calculated for C$_{18}$ H$_{22}$ N$_3$ O$_4$ S Cl:

| Theory: | C 52.49, | H 5.38, | N 10.20. |
|---|---|---|---|
| Found: | C 51.94, | H 5.20, | N 9.87. |

Preparation of Final Title Compound

Scheme XII, Step B: Into a 25-3n flask fitted with a stirrer and thermometer, 100 mg of (6-chloro(3-pyridyl))-N-[4-(1-hydroxy-1-methyl-2-{[(methylethyl)sulfonyl]amino}ethyl)phenyl]carboxamide in CH$_2$Cl$_2$ (5 mL) was added dropwise to 0.03 mL DAST in CH$_2$CL$_2$ (5 mL) while stirring at –78° C. under a nitrogen atmosphere. Reaction was allowed to warm to room temperature and diluted with CH$_2$Cl$_2$ (25 mL). This organic layer was washed with H$_2$O, dried over Na$_2$SO$_4$, and concentrated under reduced vacuum to yield 118 mg as a foam. This material was triturated in hexane/ethyl acetate 19:1 for ½ h and then filtered to yield the final title compound (80 mg, 81%) as a white solid. Ion spray M.S. 414.1 (M*).

Calculated for: C$_{18}$H$_{21}$N$_3$O$_3$SFCl:

| Theory: | C 52.23, | H 5.11, | N 10.15. |
|---|---|---|---|
| Found: | C 52.49, | H 5.26, | N 9.75. |

EXAMPLE 27

Preparation of (4-Cyanophenyl)-N-[4-(1-fluoro-1-methyl-2-{[(methylethyl)sulfonyl]amino}ethyl)phenyl]carboxamide

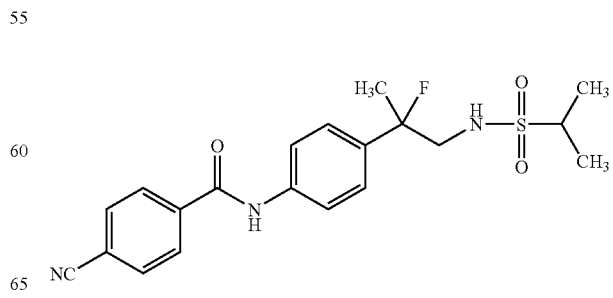

Preparation of (4-Cyanophenyl)-N-[4-(1-hydroxy-1-methyl-2-{[(methylethyl)sulfonyl]amino}ethyl)phenyl]carboxamide

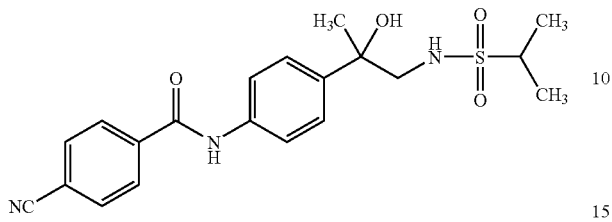

Scheme XII, Step A: Into a 100 mL single-neck flask, 135 mg of 4-cyanobenzoyl chloride was added dropwise to 200 mg of [2-(4-aminophenyl)-2-hydroxypropyl][(methylethyl)sulfonyl]amine (prepared in example 19) and 83 mg of triethylamine in THF (25 mL) while stirring under a nitrogen atmosphere at room temperature. The reaction was allowed to stir at this temperature for 2 h. The mixture was then poured into $H_2O$ and the desired product was extracted into ethyl acetate. The organic layer was backwashed once with $H_2O$, dried over $K_2CO_3$, and concentrated under reduced vacuum to yield 294 mg as a white solid. This material was purified via recrystallization from ethyl acetate/hexane 2:1 to yield intermediate title compound (131 mg, 55%) as a white solid. Ion spray M.S. 400.2 (M*−1).

Calculated for $C_{20} H_{23} N_3 O_4 S$:

| Theory: | C 59.83, | H 5.77, | N 10.46. |
| Found: | C 59.00, | H 5.53, | N 10.27. |

Preparation of Final Title Compound

Scheme XII, Step B: Into a 25 mL 3 neck flask fitted with a stirrer and thermometer, 100 mg of (4-cyanophenyl)-N-[4-(1-hydroxy-1-methyl-2-{[(methylethyl)sulfonyl]amino}ethyl)phenyl]carboxamide in $CH_2Cl_2$ (5 mL) was added dropwise to 0.03 mL DAST in $CH_2CL_2$ (5 mL) while stirring at −78° C. under a nitrogen atmosphere. The reaction was allowed to warm to room temperature and diluted with $CH_2Cl_2$ (25 mL). This organic layer was washed with $H_2O$, dried over $Na_2SO_4$, and concentrated under reduced vacuum to yield 107 mg as a yellow solid. This material was triturated in hexane/ethyl acetate 19:1 for ½ h and then filtered to yield the final title compound (65 mg, 65%) as a tan solid. Ion spray M.S. 404.1 (M*+1).

Calculated for: $C_{20}H_{22}N_3O_3SF—½H_2O$:

| Theory: | C 58.23, | H 5.62, | N 10.18. |
| Found: | C 58.36, | H 5.37, | N 10.16. |

EXAMPLE 28

Preparation of Ethoxy-N-[4-(1-fluoro-1-methyl-2-{[(methylethyl)sulfonyl]amino}ethyl)phenyl]carboxamide

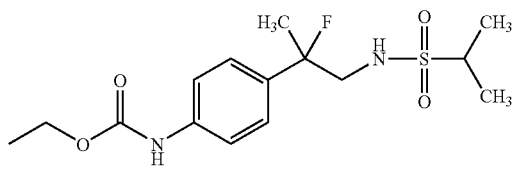

Preparation of Ethoxy-N-[4-(1-hydroxy-1-methyl-2-{[(methylethyl)sulfonyl]amino}ethyl)phenyl]carboxamide

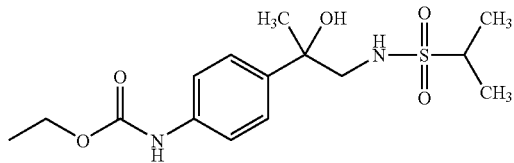

Scheme XII, Step A: Into a 100 mL single-neck flask, 89 mg of ethyl chloroformate was added dropwise to 200 mg of [2-(4-aminophenyl)-2-hydroxypropyl][(methylethyl)sulfonyl]amine (prepared in example 19) and 83 mg of triethylamine in THF (25 mL) while stirring under a nitrogen atmosphere at room temperature. The reaction was allowed to stir at this temperature for 2 h. The mixture was then poured into $H_2O$ and the desired product was extracted into ethyl acetate. The organic layer was backwashed once with $H_2O$, dried over $K_2CO_3$, and concentrated under reduced vacuum to yield 317 mg as an oil. This material was purified via silica gel chromatography employing the Chromatotron while using a 4000 micron rotor and eluting with an isocratic solvent of methylene chloride/ethyl acetate 7:3 to yield intermediate title compound (200 mg, 78%) as a viscous oil. Ion spray M.S. 343.2 (M*−1).

Calculated for $C_{15} H_{24} N_2 O_5 S$:

| Theory: | C 52.30, | H 7.02, | N 8.13. |
| Found: | C 52.01, | H 6.98, | N 7.95. |

Preparation of Final Title Compound

Scheme XII, Step B: Into a 25 mL, 3 neck flask fitted with a stirrer and thermometer, 175 mg of ethoxy-N-[4-(1-hydroxy-1-methyl-2-{[(methylethyl)sulfonyl]amino}ethyl)phenyl]carboxamide in $CH_2Cl_2$ (5 mL) was added dropwise to 0.04 mL DAST in $CH_2CL_2$ (10 mL) while stirring at −78° C. under a nitrogen atmosphere. The reaction was allowed to warm to room temperature and diluted with $CH_2Cl_2$ (25 mL). This organic layer was washed with $H_2O$, dried over $Na_2SO_4$, and concentrated under reduced vacuum to yield 181 mg as an oil. This material was purified via silica gel chromatography employing the Chromatotron, using a 2000 micron rotor and eluting with a solvent of hexane/ethyl acetate 7:3 to yield the final title compound (101 mg, 57%) as a viscous oil. Ion spray M.S. 345.1 (M*−1).

Calculated for: $C_{15}H_{23}N_2O_4SF$:

| Theory: | C 52.01, | H 6.69, | N 8.09. |
|---|---|---|---|
| Found: | C 51.82, | H 6.64, | N 8.22. |

EXAMPLE 29

Preparation of N-[4-(1-Fluoro-1-methyl-2-{[(methylethyl)sulfonyl]amino}ethyl)phenyl]isoxazol-5-ylcarboxamide

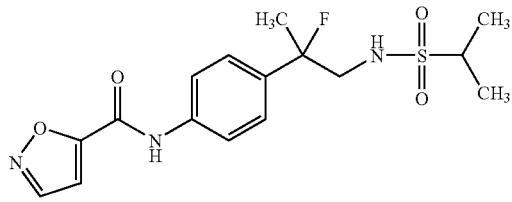

Preparation of N-[4-(1-Hydroxy-1-methyl-2-{[(methylethyl)sulfonyl]amino}ethyl)phenyl]isoxazol-5-ylcarboxamide

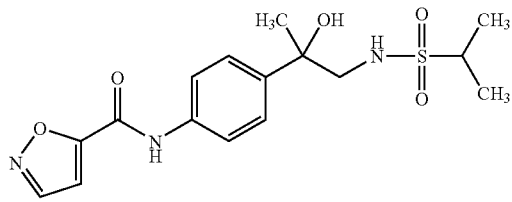

Scheme XII, Step A: Into a 100 mL single-neck flask, 159 mg of isoxazole-5-carbonyl chloride was added dropwise to 300 mg of [2-(4-aminophenyl)-2-hydroxypropyl][(methylethyl)sulfonyl]amine (prepared in example 19) and 122 mg of triethylamine in THF (35 mL) while stirring under a nitrogen atmosphere at room temperature. The reaction was allowed to stir at this temperature for 2 h. The mixture was then poured into $H_2O$ and the desired product was extracted into ethyl acetate. The organic layer was backwashed once with $H_2O$, dried over $K_2CO_3$, and concentrated under reduced vacuum to yield 416 mg as a solid. This material was purified via recrystallization from ethyl acetate/hexane 1:1 to yield intermediate title compound (207 mg, 51%) as a white solid. Ion spray M.S. 366.1 (M*−1).

Calculated for $C_{16} H_{21} N_3 O_5 S$

| Theory: | C 52.30, | H 5.76, | N 11.43. |
|---|---|---|---|
| Found: | C 52.25, | H 5.80, | N 11.25. |

Preparation of Final Title Compound

Scheme XII, Step B: Into a 25 mL 3 neck flask fitted with a stirrer and thermometer, 200 mg of N-[4-(1-hydroxy-1-methyl-2-{[(methylethyl)sulfonyl]amino}ethyl)phenyl] isoxazol-5-ylcarboxamide in $CH_2Cl_2$ (5 mL) was added dropwise to 0.07 mL DAST in $CH_2CL_2$ (10 mL) while stirring at −78° C. under a nitrogen atmosphere. The reaction was allowed to warm to room temperature and diluted with $CH_2Cl_2$ (25 mL). This organic layer was washed with $H_2O$, dried over $Na_2SO_4$, and concentrated under reduced vacuum to yield 321 mg as an oil. This material was purified via silica gel chromatography employing the Chromatotron, using a 2000 micron rotor and eluting with a solvent of hexane/ethyl acetate 1:1 to yield the final title compound (187 mg, 94%) as a semi-solid. Ion spray M.S. 368.2 (M*−1).

Calculated for: $C_{16}H_{20}N_3O_4SF$:

| Theory: | C 52.02, | H 5.46, | N 11.37. |
|---|---|---|---|
| Found: | C 51.70, | H 5.59, | N 10.88. |

EXAMPLE 30

Preparation of 4-(Dimethylamino)-N-[4-(1-fluoro-1-methyl-2-{[(methylethyl)sulfonyl]amino}ethyl)phenyl]butanamide

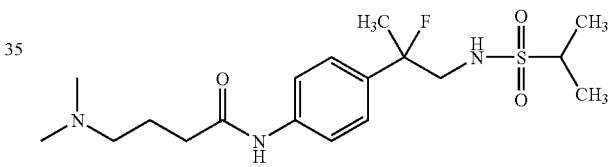

Preparation of 4-(Dimethylamino)-N-[4-(1-hydroxy-1-methyl-2-{[(methylethyl)sulfonyl]amino}ethyl) phenyl]butanamide

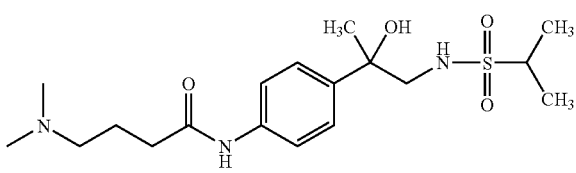

Into a 50 mL single-neck flask, 1 mL of oxalyl chloride was added syringe wise to 306 mg of 4-(dimethylamino) butyric acid hydrochloride in $CH_2Cl_2$ (20 mL) while stirring under a nitrogen atmosphere at room temperature. Then at this temperature. 1 drop of DMF was added by pipette and the mixture began to foam. The reaction was allowed to stir at this temperature for 1 h and was then concentrated under reduced vacuum to yield a yellow solid. This solid was added portion wise to a 100 mL single-neck flask containing 460 mg of [2-(4-aminophenyl)-2-hydroxypropyl][(methylethyl)sulfonyl]amine (prepared in example 19) and 183 mg of triethylamine in THF (25 mL) while stirring at room temperature under a nitrogen atmosphere. After 2 h at this temperature, the mixture was concentrated under reduced vacuum and the resulting solid was taken into ethyl acetate. The organic layer was backwashed once with $H_2O$, dried over $K_2CO_3$, and concentrated under reduced vacuum to yield 794 mg as an oil. This material was purified via silica gel chromatography employing the Chromatotron while using a 4000 micron rotor and eluting with an isocratic solvent of methanol/1% $NH_4OH$ to yield intermediate title compound (350 mg, 51%) as a viscous oil. Ion spray M.S. 385 (M*).

Preparation of Final Title Compound

Scheme I, Step B: Into a 25 mL 3 neck flask fitted with a stirrer and thermometer, 335 mg of 4-(dimethylamino)-N-[4-(1-hydroxy-1-methyl-2-{[(methylethyl)sulfonyl]amino}ethyl)phenyl]butanamide in $CH_2Cl_2$ (5 mL) was added dropwise to 0.11 mL DAST in $CH_2CL_2$ (10 mL) while stirring at −78° C. under a nitrogen atmosphere. Reaction was allowed to warm to room temperature and diluted with $CH_2Cl_2$ (25 mL). This organic layer was washed with $H_2O$, dried over $Na_2SO_4$, and concentrated under reduced vacuum to yield 160 mg as an oil. This material was purified via silica gel chromatography employing the Chromatotron, using a 2000 micron rotor and eluting with a solvent of methanol/1% $NH_4OH$ to yield the final title compound (100 mg, 30%) as a semi-solid. Ion spray M.S. 388.0 (M*+1).

EXAMPLE 31

Preparation of N-[4-(1-Fluoro-1-methyl-2-{[(methylethyl)sulfonyl]amino}ethyl)phenyl]-3-thienylcarboxamide

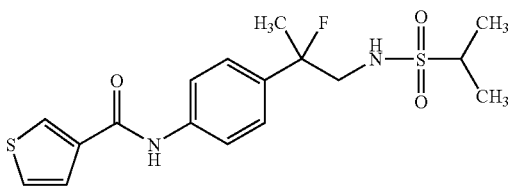

Preparation of N-[4-(1-Hydroxy-1-methyl-2-{[(methylethyl)sulfonyl]amino}ethyl)phenyl]-3-thienylcarboxamide

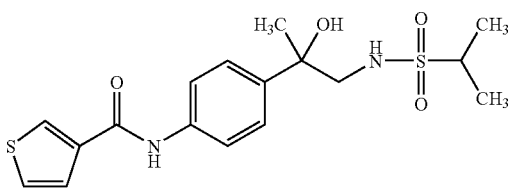

Scheme XII, Step A: [2-(4-aminophenyl)-2-hydroxypropyl][(methylethyl)sulfonyl]amine (300 mg, 1.1 mmol, prepared in example 19), 3-thiophenecarboxylic acid (169 mg, 1.2 mmol), triethylamine (333 mg, 3.0 mmol), 4-dimethylaminopyridine (15 mg, DMAP), 1-[3-(dimethylamino)propyl]-3-ethylcarbodiimide-HCl (260 mg, 1.2 mmol) and methylene chloride (25 mL) were mixed together in a 50 mL single neck flask and stirred under a nitrogen atmosphere at room temperature for 64 hours. The solution was then poured into $H_2O$, and the desired product was extracted with ethyl acetate. The organic layer was backwashed once with $H_2O$, dried over $K_2CO_3$, and concentrated under reduced vacuum to yield 634 mg as an oil. This material was purified via silica gel chromatography employing the Chromatotron, using a 4000 micron rotor and eluting with a solvent of hexane/ethyl acetate 1:1 to yield intermediate title compound (151 mg, 36%) as a white solid. Ion spray M.S. 381.1 (M*+1).

Calculated for: $C_{17}H_{22}N_2O_4S_2$:

| Theory: | C 53.38, | H 5.80, | N 7.32. |
| Found: | C 53.29, | H 5.79, | N 7.39. |

Preparation of Final Title Compound

Scheme XII, Step B: Into a 25 mL 3 neck flask fitted with a stirrer and thermometer, 100 mg of N-[4-(1-hydroxy-1-methyl-2-{[(methylethyl)sulfonyl]amino}ethyl)phenyl]-3-thienylcarboxamide in $CH_2Cl_2$ (5 mL) was added dropwise to 0.03 mL DAST in $CH_2CL_2$ (5 mL) while stirring at −78° C. under a nitrogen atmosphere. The reaction was allowed to warm to room temperature and diluted with $CH_2Cl_2$ (25 mL). This organic layer was washed with $H_2O$, dried over $Na_2SO_4$, and concentrated under reduced vacuum to yield 111 mg as a foam. This material was triturated in hexane/ethyl acetate 19:1 for ½ h and then filtered to yield the final title compound (80 mg, 70%) as a white solid. Ion spray M.S. 385.1 (M*+1).

Calculated for: $C_{17}H_{21}N_2O_3S_2F$:

| Theory: | C 53.11, H 5.51, N 7.29. |
| Found: | C 52.93, H 5.44, N 7.15. |

EXAMPLE 32

Preparation of {2-Fluoro-2-[4-(phenylmethoxy)phenyl]propyl}[(methylethyl)sulfonyl]amine

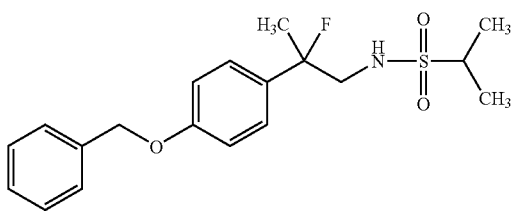

Preparation of 1-Amino-2-[4-(phenylmethoxy)phenyl]propan-2-ol

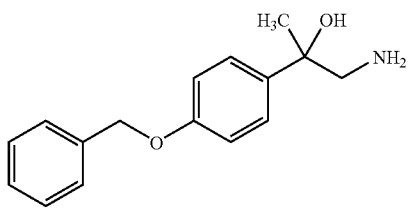

Into a 100 mL single-neck flask, 50 mL of trimethylsilyl cyanide was added dropwise to 26 g of 4'-benzyloxacetophenone and 3.9 g of zinc iodide while stirring under a nitrogen atmosphere at room temperature. The reaction was allowed to stir at this temperature overnight. In the morning, the mixture was diluted with methylene chloride (100 mL) and the organic layer was backwashed once with sat. $Na_2HCO_3$, dried over $MgSO_4$, and concentrated under reduced vacuum to yield 23.25 g. as an orange oil. Because of possible stability problems, this material was used immediately and placed into 300 mL THF in a 1000 mL single-neck flask. While stirring at room temperature under a nitrogen atmosphere, 100 mL of $BH_3$-THF complex was added syringe wise and the reaction was stirred overnight. In the morning, 10 mL of con. hydrochloric acid was added dropwise at room temperature and severe foaming was present. The mixture was then concentrated under reduced vacuum. The resulting HCl salt was liberated while being stirred in 1N NaOH and the free amine was extracted into ethyl acetate. This organic layer was washed with $H_2O$, dried over $Na_2SO_4$, and concentrated under reduced vacuum to yield 24.31 g. as a semi-solid. This material was purified via silica gel chromatography employing the Water's prep. 2000 and eluting with a gradient solvent of methylene chloride/methanol 9:1 to methanol/1% $NH_4OH$ to yield intermediate title compound (8.61 g, 27%) as a white solid. (FD) M.S. 256.9 (M*).

Calculated for: $C_{16}H_{19}NO_2$:

| | |
|---|---|
| Theory: | C 74.68, H 7.44, N 5.44. |
| Found: | C 74.20, H 7.29, N 5.44. |

Preparation of {2-Hydroxy-2-[4-(phenylmethoxy)phenyl]propyl}[(methylethyl)sulfonyl]amine

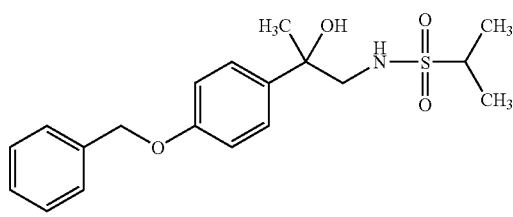

Scheme I, Step A: In a 1000 mL-3n flask fitted with a stirrer and thermometer, 5.69 g. of propanesulfonyl chloride was added dropwise to 8.60 g. of 1-amino-2-[4-(phenylmethoxy)phenyl]propan-2-ol and 6.21 g. of DBU in THF (300 mL) while stirring at 0° C. under a nitrogen atmosphere. The reaction was allowed to warm to room temperature and stirred overnight at this temperature. In the morning, reaction was concentrated under reduced vacuum. The resulting oil was taken into ethyl acetate and the organic layer was washed two times with $H_2O$, dried over $Na_2SO_4$, and concentrated under reduced vacuum to yield 10.2 g. as a solid. This material was purified via silica gel chromatography employing the Water's prep. 2000 and eluting with a solvent of hexane/ethyl acetate 9:1 to yield intermediate title compound (6.14 g, 50%) as a white solid. Ion spray M.S. 362.2 (M*-1).

Calculated for: $C_{19}H_{25}NO_4S$:

| | |
|---|---|
| Theory: | C 62.79, H 6.93, N 3.85. |
| Found: | C 62.85, H 6.89, N 3.88. |

Preparation of Final Title Compound

Scheme I, Step B: Into a 25 mL 3 neck flask fitted with a stirrer and thermometer, 400 mg of {2-hydroxy-2-[4-(phenylmethoxy)phenyl]propyl}[(methylethyl)sulfonyl]amine in $CH_2Cl_2$ (5 mL) was added dropwise to 0.1 mL DAST in $CH_2CL_2$ (5 mL) while stirring at −78° C. under a nitrogen atmosphere. The reaction was allowed to warm to room temperature and diluted with $CH_2Cl_2$ (25 mL). This organic layer was washed with $H_2O$, dried over $Na_2SO_4$, and concentrated under reduced vacuum to yield 340 mg as a yellow oil. This material was purified via silica gel chromatography employing the Chromatotron and using a 2000 micron rotor while eluting with a solvent of hexane/ethyl acetate 7:3 to yield the final title compound (271 mg, 68%) as a semi-solid. Ion spray M.S. 364.2 (M*-1).

Calculated for $C_{19}H_{24}NO_3SF$:

| | |
|---|---|
| Theory: | C 62.44, H 6.62, N 3.83. |
| Found: | C 62.39, H 6.58, N 3.92. |

EXAMPLE 33

Preparation of 2-{[4-(1-Fluoro-1-methyl-2-{[(methylethyl)sulfonyl]amino}ethyl)phenoxy]methyl}benzenecarbonitrile

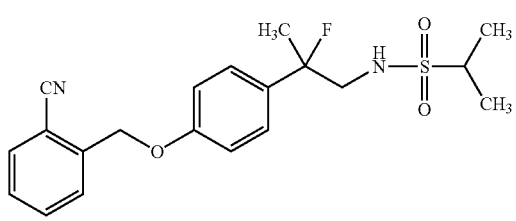

Preparation of [2-Hydroxy-2-(4-hydroxyphenyl)propyl][(methylethyl)sulfonyl]amine

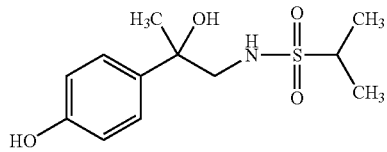

3.00 g of {2-hydroxy-2-[4-(phenylmethoxy)phenyl]propyl}[(methylethyl)sulfonyl]amine (prepared in example 32) and 3.10 g. of 10% Pd/C in ethyl acetate (300 mL) were subjected to a hydrogen atmosphere while shaking at 60 psi's for 4 hours. Solution was filtered through a Celite mat and the resulting filtrate was concentrated under reduced vacuum to yield intermediate title compound (2.48 g, 100%) as a foam. This material slowly crystallized and was used without further purification. Ion spray M.S. 272.1 (M*−1).

Calculated for $C_{12}H_{19}NO_4S-\frac{1}{2}H_2O$:

| Theory: | C 51.03, H 7.14, N 4.96 |
| Found:  | C 51.20, H 7.21, N 4.71 |

Preparation of 2-{[4-(1-Hydroxy-1-methyl-2-{[(methylethyl)sulfonyl]amino}ethyl)phenoxy]methyl}benzenecarbonitrile

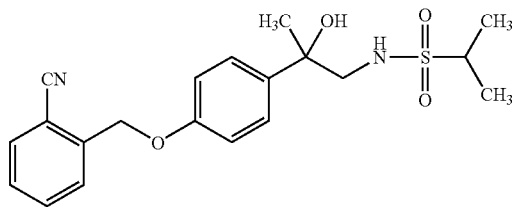

Scheme XI, Step A: Into a 250 mL-3 neck flask fitted with a stirrer and thermometer, 400 mg of [2-hydroxy-2-(4-hydroxyphenyl)propyl][(methylethyl)sulfonyl]amine in DMF (10 mL) was added dropwise to 40 mg of NaH in DMF (30 mL) while stirring at room temperature under a nitrogen atmosphere. After stirring at this temperature for 30 minutes, 290 mg of alpha-bromo 2-cyanotoluene in DMF (10 mL) was added dropwise followed by the addition of 184 mg of NaI portion wise. The reaction was then heated at 100° C. for 2 hours. The mixture was cooled to room temperature and poured into H₂O and the desired product was extracted with ethyl acetate. This organic layer was washed with H₂O, dried over K₂CO₃, and concentrated under reduced vacuum to yield 612 mg of a brown oil. This material was purified via silica gel chromatography employing the Chromatotron and using a 4000 micron rotor while eluting with a solvent of hexane/ethyl acetate 1:1 to yield intermediate title compound (161 mg, 28%) as a viscous oil. Ion spray M.S. 387.9 (M*−1).

Calculated for $C_{20}H_{24}N_2O_4S$:

| Theory: | C 61.84, H 6.23, N 7.21 |
| Found:  | C 59.83, H 5.65, N 7.36 |

Preparation of Final Title Compound

Scheme XI, Step B: Into a 25 mL 3 neck flask fitted with a stirrer and thermometer, 150 mg of 2-{[4-(1-hydroxy-1-methyl-2-{[(methylethyl)sulfonyl]amino}ethyl)phenoxy]methyl}benzenecarbonitrile in CH₂Cl₂ (5 mL) was added dropwise to 0.06 mL DAST in CH₂CL₂ (5 mL) while stirring at −78° C. under a nitrogen atmosphere. The reaction was allowed to warm to room temperature and diluted with CH₂Cl₂ (25 mL). This organic layer was washed with H₂O, dried over Na₂SO₄, and concentrated under reduced vacuum to yield 157 mg as a yellow oil. This material was purified via silica gel chromatography employing the Chromatotron and using a 2000 micron rotor while eluting with a solvent of hexane/ethyl acetate 9:1 to yield the final title compound (91 mg, 60%) as a solid. Ion spray M.S. 389.2 (M*−1).

Calculated for $C_{20}H_{23}N_2O_3SF$:

| Theory: | C 61.52, H 5.94, N 7.17. |
| Found:  | C 61.16, H 5.93, N 7.14. |

EXAMPLE 34

Preparation of [2-Fluoro-2-(4-methoxyphenyl)propyl][(methylethyl)sulfonyl]amine

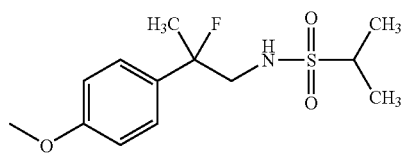

Preparation of 1-Amino-2-(4-methoxyphenyl)propan-2-ol

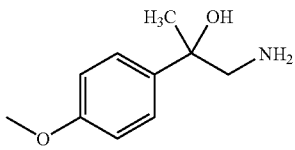

Into a 100 mL single-neck flask, 28.5 mL of trimethylsilyl cyanide was added dropwise to 10 g of 4'-methoxyacetophenone and 2.28 g of zinc iodide while stirring under a nitrogen atmosphere. The reaction was allowed to stir at this temperature overnight. In the morning, the mixture was diluted with methylene chloride (100 mL) and the organic layer was backwashed once with sat. Na₂HCO₃, dried over MgSO₄, and concentrated under reduced vacuum to yield 13 g. as a tan oil. Because of possible stability problems, this material was used immediately and placed into 200 mL THF in a 500 mL single-neck flask. While stirring at room temperature under a nitrogen atmosphere, 70 mL of BH$_3$-THF complex was added syringe wise and the reaction was stirred overnight. In the morning, 10 mL of concentrated hydrochloric acid was added dropwise at room temperature and severe foaming was present. The mixture was then concentrated under reduced vacuum. The resulting HCl salt was liberated while being stirred in 1N NaOH and the free amine was extracted into ethyl acetate. This organic layer was washed with H$_2$O, dried over Na$_2$SO$_4$, and concentrated under reduced vacuum to yield 7.31 g. of a 2 spot material. This material was purified via silica gel chromatography employing the Water's prep. 2000 and eluting with a solvent of methylene chloride/methanol 9:1 to yield intermediate title compound (3.01 g, 24%) as an oil as the top spot. (FD) M.S. 180.3 (M*−1).

Calculated for: C$_{10}$H$_{15}$NO$_2$

| | |
|---|---|
| Theory: | C 66.27, H 8.34, N 7.73. |
| Found: | C 64.46, H 7.94, N 7.50. |

Preparation of [2-Hydroxy-2-(4-methoxyphenyl)propyl][(methylethyl)sulfonyl]amine

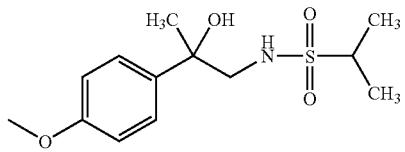

Scheme I, Step A: In a 500 mL-3n flask fitted with a stirrer and thermometer, 2.53 g. of propanesulfonyl chloride was added dropwise to 3.00 g. of 1-amino-2-(4-methoxyphenyl)propan-2-ol and 2.70 g. of DBU in THF (200 mL) while stirring at 0° C. under a nitrogen atmosphere. The reaction was allowed to warm to room temperature and stirred overnight at this temperature. In the morning, reaction was concentrated under reduced vacuum. The resulting oil was taken into ethyl acetate and the organic layer was washed two times with H$_2$O, dried over Na$_2$SO$_4$, and concentrated under reduced vacuum to yield 3.61 g. as a solid. This material was purified via silica gel chromatography employing the Water's prep. 2000 and eluting with a solvent of hexane/ethyl acetate 9:1 to yield intermediate title compound (2.71 g, 57%) as a white solid. Ion spray M.S. 286.2 (M*−1).

Preparation of Final Title Compound

Scheme I, Step B: Into a 50 mL 3 neck flask fitted with a stirrer and thermometer, 1.00 gm. of [2-hydroxy-2-(4-methoxyphenyl)propyl][(methylethyl)sulfonyl]amine in CH$_2$Cl$_2$ (5 mL) was added dropwise to 0.41 mL DAST in CH$_2$CL$_2$ (10 mL) while stirring at −78° C. under a nitrogen atmosphere. The reaction was allowed to warm to room temperature and diluted with CH$_2$Cl$_2$ (25 mL). This organic layer was washed with H$_2$O, dried over Na$_2$SO$_4$, and concentrated under reduced vacuum to yield 1.07 g. as a yellow oil. This material was purified via silica gel chromatography employing the Chromatotron and using a 4000 micron rotor while eluting with a solvent of hexane/ethyl acetate 7:3 to yield the final title compound (851 mg, 85%) as a viscous oil. Ion spray M.S. 288.1 (M*−1).

Calculated for C$_{13}$H$_{20}$NO$_3$SF:

| | |
|---|---|
| Theory: | C 53.96, H 6.97, N 4.84. |
| Found: | C 53.16, H 6.76, N 4.81. |

EXAMPLE 35

Preparation of {2-[4-(3,5-Difluorophenyl)phenyl]-2-fluoropropyl}[(methylethyl)sulfonyl]amine

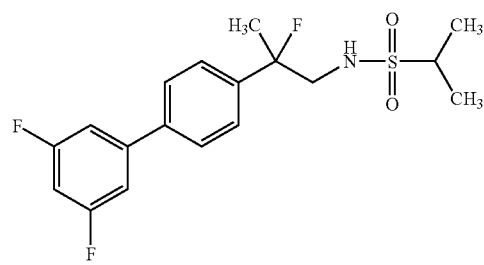

Preparation of

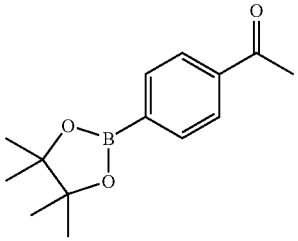

Into a 500 mL single-neck flask fitted with a stirrer and thermometer, 10.0 g. of 4'-iodoacetophenone, 1.0 g. of PdCl$_2$(dppf), and 17 mL triethylamine were placed in Dioxane (160 mL) and stirred at room temperature under a nitrogen atmosphere. This solution was then degassed with nitrogen for 15 minutes, followed by the addition of 8.8 mL pinacol borane syringe wise. Addition was exothermic and the solution turned dark immediately. The reaction was then heated at 85° C. for 6 h. The mixture was then cooled to room temperature and poured into H$_2$O and the desired product was extracted with ether. This organic layer was washed with H$_2$O, dried over MgSO$_4$, and concentrated under reduced vacuum to yield a white solid. This material was purified via silica gel chromatography employing the Water's prep. 2000 and eluting with hexane/ethyl acetate 19:1 to yield intermediate title compound, acetophenone derivative, (6.4 g, 64%) as a white powder.

Preparation of

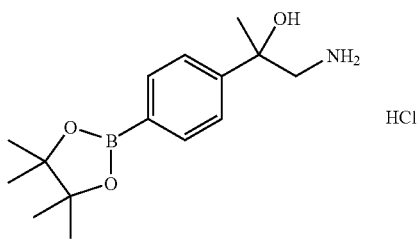

Into a 25 mL single-neck flask, 1.6 mL of trimethylsilyl cyanide was added dropwise to 1.0 g. of the acetophenone derivative prepared directly above and 131 mg of zinc iodide while stirring under a nitrogen atmosphere at room temperature. The reaction was then stirred overnight at this temperature. In the morning the mixture was diluted with methylene chloride (25 mL) and the organic layer was backwashed once with sat. $Na_2HCO_3$, dried over $MgSO_4$, and concentrated under reduced vacuum to yield 910 mg as a semi-solid. Because of possible stability problems, this material was used immediately and placed into 20 mL THF in a 100 mL single-neck flask. While stirring at room temperature under a nitrogen atmosphere, 4 mL of $BH_3$-DMS complex was added syringe wise and the reaction was refluxed for 4 hours. The reaction was cooled to room temperature and 2 mL of con. hydrochloric acid was added dropwise at room temperature and severe foaming was present. The mixture was diluted with ether (50 mL) and the reaction was stirred for an additional hour. The precipitate that formed was collected by filtration to yield intermediate title compound, amine derivative, (910 mg, 72%) as a white powder as the HCl salt.

Preparation of

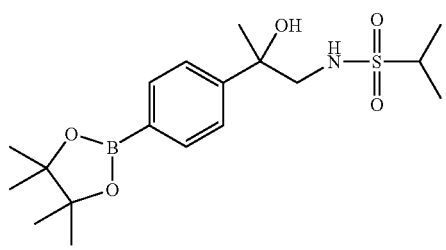

In a 250 mL 3 neck flask fitted with a stirrer and thermometer, 1.05 g. of propanesulfonyl chloride was added dropwise to 2.10 g. of the amine derivative prepared directly above, and 2.14 g. of DBU in THF (60 mL) while stirring at 0° C. under a nitrogen atmosphere. The reaction was allowed to warm to room temperature and stirred overnight at this temperature. In the morning, reaction was concentrated under reduced vacuum. The resulting oil was taken into ethyl acetate and the organic layer was washed two times with $H_2O$, dried over $Na_2SO_4$, and concentrated under reduced vacuum to yield 600 mg as an oil. This material was purified via silica gel chromatography employing the Chromatotron and using a 4000 micron rotor while eluting with a solvent of hexane/ethyl acetate 3:2 to yield intermediate title compound, sulfonyl derivative, (250 mg, 10%) as an oil. Ion spray M.S. 382.2 (M*–1).

Preparation of {2-[4-(3,5-difluorophenyl)phenyl]-2-hydroxypropyl}[(methylethyl)sulfonyl]amine

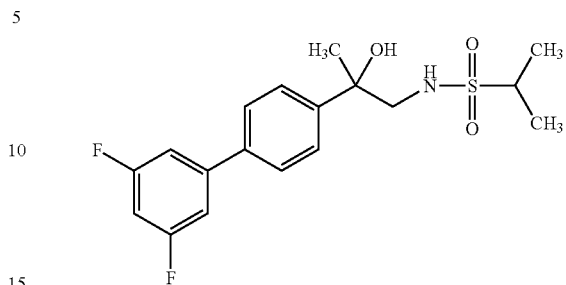

The sulfonyl derivative prepared directly above (250 mg, 0.65 mmol), 1-bromo-3,5-difluorobenzene (138 mg, 0.71 mmol), sodium carbonate (1.1 mL of a 2.0 M solution, 1.4 mmol), tetrakis(triphenyl phosphine)palladium(0) (50 mg, 0.65 mmol), and dioxane (10 mL) were mixed together in a 50 mL single neck flask and stirred at 70° C. over night. In the morning, the reaction was cooled to room temperature and poured into $H_2O$ and the desired product was extracted with ethyl acetate. The organic layer was backwashed once with $H_2O$, dried over $K_2CO_3$, and concentrated under reduced pressure to yield 286 mg of a viscous oil. This two spot material was purified via silica gel chromatography employing the Chromatotron and using a 2000 micron rotor while eluting with a solvent of hexane/ethyl acetate 1:1 to yield intermediate title compound (73 mg, 31%, top spot) as a clear oil. Ion spray M.S. 368.2 (M*–1).

Preparation of Final Title Compound

Scheme I, Step B: Into a 25 mL 3 neck flask fitted with a stirrer and thermometer, 22 mg of {2-[4-(3,5-difluorophenyl)phenyl]-2-hydroxypropyl}[(methylethyl)sulfonyl] amine in $CH_2Cl_2$ (2 mL) was added dropwise to 0.01 mL DAST in $CH_2CL_2$ (3 mL) while stirring at –78° C. under a nitrogen atmosphere. The reaction was allowed to warm to room temperature and diluted with $CH_2Cl_2$ (25 mL). This organic layer was washed with $H_2O$, dried over $Na_2SO_4$, and concentrated under reduced vacuum to yield 18.4 mg as a yellow oil. This material was purified via silica gel chromatography employing the Chromatotron and using a 1000 micron rotor while eluting with a solvent of hexane/ethyl acetate 7:3 to yield the final title compound (12 mg, 52%) as a viscous oil. Ion spray M.S. 370.2 (M*–1).

EXAMPLE 36

Preparation of [(Dimethylamino)sulfonyl][2-fluoro-2-(4-iodophenyl)propyl]amine

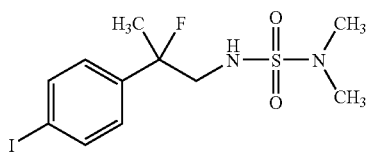

Preparation of [(Dimethylamino)sulfonyl][2-hydroxy-2-(4-iodophenyl)propyl]amine

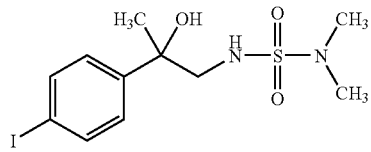

Scheme X, Step A: In a 500 mL-3 neck flask fitted with a stirrer and thermometer, 358 mg of dimethylsulfamoyl chloride was added dropwise to 554 mg of 1-amino-2-(4-iodophenyl)propan-2-ol (intermediate prepared in example 1) and 380 mg of DBU in THF (125 mL) while stirring at 0° C. under a nitrogen atmosphere. The reaction was allowed to warm to room temperature and stirred overnight at this temperature. In the morning, reaction was concentrated under reduced vacuum. The resulting oil was taken into ethyl acetate and the organic layer was washed two times with $H_2O$, dried over $Na_2SO_4$, and concentrated under reduced vacuum to yield an oil. This material was purified via silica gel chromatography employing the Chromatotron and using a 2000 micron rotor while eluting with a solvent of hexane/ethyl acetate 3:1 to yield intermediate title compound (257 mg, 33%) as a white solid. (Fd) M.S. 384 (M*).

Calculated for: $C_{11}H_{17}N_2O_3SI$:

| | |
|---|---|
| Theory: | C 34.39, H 4.46, N 7.29. |
| Found: | C 33.25, H 4.24, N 6.80. |

Preparation of Final Title Compound

Scheme X, Step B: Into a 50 mL 3 neck flask fitted with a stirrer and thermometer, 257 mg of [(dimethylamino)sulfonyl][2-hydroxy-2-(4-iodophenyl)propyl]amine in $CH_2Cl_2$ (10 mL) was added dropwise to 0.08 mL DAST in $CH_2CL_2$ (10 mL) while stirring at −78° C. under a nitrogen atmosphere. The reaction was allowed to warm to room temperature and diluted with $CH_2Cl_2$ (25 mL). This organic layer was washed with $H_2O$, dried over $Na_2SO_4$, and concentrated under reduced vacuum to yield a yellow oil. This material was purified via silica gel chromatography employing the Chromatotron and using a 2000 micron rotor while eluting with a solvent of hexane/ethyl acetate 3:1 to yield the final title compound (147 mg, 57%) as a white solid; m.p. 115°–117° C. Ion spray M.S. 385 (M*+1).

Calculated for: $C_{11}H_{16}N_2O_2SI$:

| | |
|---|---|
| Theory: | C 34.21, H 4.18, N 7.25. |
| Found: | C 34.04, H 4.41, N 7.59. |

EXAMPLE 37

Preparation of 4-[4-(2-{[(Dimethylamino)sulfonyl]amino}-1-fluoroisopropyl)phenyl]benzenecarbonitrile

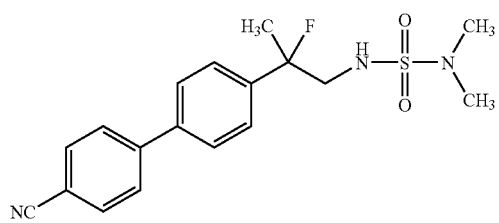

Preparation of 4-[4-(2-{[(Dimethylamino)sulfonyl]amino}-1-hydroxyisopropyl)phenyl]benzenecarbonitrile

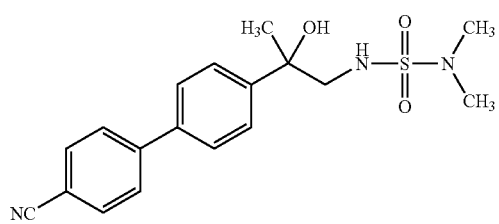

Scheme VI, Step A: [(Dimethylamino)sulfonyl][2-hydroxy-2-(4-iodophenyl)propyl]amine (384 mg, 1.0 mmol, prepared in example 36), 4-cyanobenzene boronic acid (191 mg, 1.3 mmol), potassium carbonate (179 mg, 1.3 mmol), tetrakis(triphenyl phosphine)palladium(0) (58 mg, 0.05 mmol), and dioxane/water (60 mL, 3:1) were mixed together in a 100 mL single neck flask and stirred at 70° C. over night. In the morning, the reaction was cooled to room temperature and poured into $H_2O$ and the desired product was extracted with ethyl acetate. The organic layer was backwashed once with $H_2O$, dried over $K_2CO_3$, and concentrated under reduced pressure to yield a viscous oil. This two spot material was purified via silica gel chromatography employing the Chromatotron and using a 2000 micron rotor while eluting with a solvent of methylene chloride/ethyl acetate 9:1 to yield intermediate title compound (255 mg, 71%, bottom spot) as a white solid. (FD) M.S. 359 (M*).

Calculated for: $C_{18}H_{21}N_3O_3S—¼H_2O$:

| | |
|---|---|
| Theory: | C 59.34, H 5.77, N 11.54. |
| Found: | C 58.89, H 5.63, N 11.26. |

Preparation of Final Title Compound

Scheme VI, Step B: Into a 25 mL 3 neck flask fitted with a stirrer and thermometer, 209 mg of 4-[4-(2-{[(dimethylamino)sulfonyl]amino}-1-hydroxyisopropyl)phenyl]benzenecarbonitrile in $CH_2Cl_2$ (2 ml) was added dropwise to 0.07 mL DAST in $CH_2CL_2$ (3 mL) while stirring at −78° C. under a nitrogen atmosphere. The reaction was allowed to warm to room temperature and diluted with CH₂Cl₂ (25 mL). This organic layer was washed with H₂O, dried over Na₂SO₄, and concentrated under reduced vacuum to yield a solid. This material was purified via silica gel chromatography employing the Chromatotron and using a 2000 micron rotor while eluting with a solvent of hexane/ethyl acetate 3:1 to yield the final title compound (132 mg, 63%) as a white solid. (FD) M.S. 361 (M*).

EXAMPLE 38

Preparation of {2-[4-(3-aminophenyl)phenyl]-2-fluoropropyl}[(dimethylamino)sulfonyl]amine

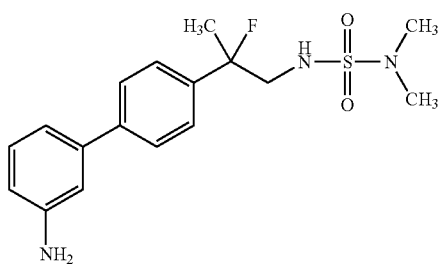

[(Dimethylamino)sulfonyl][2-fluoro-2-(4-iodophenyl) propyl]amine (386, 1.0 mmol, prepared in example 36), 3-aminobenzeneboronic acid (201 mg, 1.3 mmol), potassium carbonate (179 mg, 1.3 mmol), tetrakis(triphenyl phosphine)palladium(0) (58 mg, 0.05 mmol), and dioxane/water (60 mL, 3:1) are mixed together in a 100 mL single neck flask and stirred at 70° C. over night. In the morning, the reaction is cooled to room temperature and poured into H₂O, and the desired product is extracted with ethyl acetate. The organic layer is backwashed once with H₂O, dried over K₂CO₃, filtered, and concentrated under reduced pressure. The crude material is purified via silica gel chromatography employing the Chromatotron and using a 2000 micron rotor with hexane/ethyl acetate eluent to provide the title compound.

EXAMPLE 39

Preparation of [(Dimethylamino)sulfonyl][2-fluoro-2-(4-{3-[(methylsulfonyl)amino]phenyl}phenyl) propyl]amine

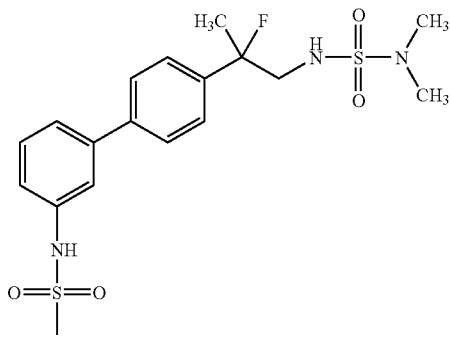

In a 250 mL 3 neck flask fitted with a stirrer and thermometer, 285 mg of methanesulfonyl chloride is added dropwise to 350 mg of {2-[4-(3-aminophenyl)phenyl]-2-fluoropropyl}[(dimethylamino)sulfonyl]amine (prepared in example 38) and 380 mg of DBU in THF (125 mL) while stirring at 0° C. under a nitrogen atmosphere. The reaction is allowed to warm to room temperature and then stirred overnight at this temperature. In the morning, the reaction is concentrated under reduced vacuum. The resulting material is taken into ethyl acetate and the organic layer is washed two times with H₂O, dried over Na₂SO₄, filtered, and concentrated under reduced vacuum. This crude material is purified via silica gel chromatography employing the Chromatotron and using a 4000 micron rotor with hexane/ethyl acetate eluent to provide the title compound.

EXAMPLE 40

Preparation of [(Dimethylamino)sulfonyl]{2-fluoro-2-[4-(3-{[(methylethyl)sulfonyl]amino}phenyl)phenyl]propyl}amine

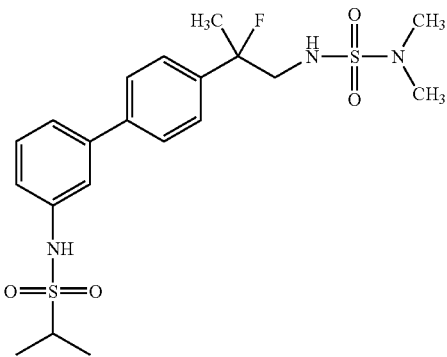

In a 250 mL 3 neck flask fitted with a stirrer and thermometer, 356 mg of 2-propanesulfonyl chloride is added dropwise to 350 mg of {2-[4-(3-aminophenyl)phenyl]-2-fluoropropyl}[(dimethylamino)sulfonyl]amine (prepared in example 38) and 380 mg of DBU in THF (125 mL) while stirring at 0° C. under a nitrogen atmosphere. The reaction is allowed to warm to room temperature and then stirred overnight at this temperature. In the morning, the reaction is concentrated under reduced vacuum. The resulting material is taken into ethyl acetate and the organic layer is washed two times with H₂O, dried over Na₂SO₄, filtered, and concentrated under reduced vacuum. This crude material is purified via silica gel chromatography employing the Chromatotron and using a 4000 micron rotor with hexane/ethyl acetate eluent to provide the title compound.

EXAMPLE 41

Preparation of 4-[4-(1-Fluoro-1-methyl-2-{[(methylethyl)sulfonyl]amino}ethyl)phenyl]benzenesulfonamide

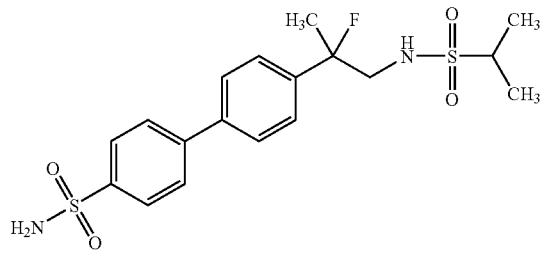

Preparation of 4-Bromobenzenesulfonamide

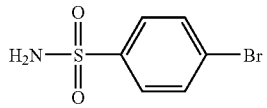

4-Bromobenzenesulfonyl chloride (1.0 g, 3.9 mmol), methanol/ammonia solution (5 mL, excess), and methanol (5 mL) were mixed together in a 25 mL-single neck flask and stirred overnight under a nitrogen atmosphere. In the morning, the reaction was concentrated under reduced vacuum to yield intermediate title compound (1.13 g, 100%) as a white solid. This material was used without further purification. Ion spray M.S. 235.9 (M*).

Preparation of 4-[4-(1-Hydroxy-1-methyl-2-{[(methylethyl)sulfonyl]amino}ethyl)phenyl]benzensulfonamide

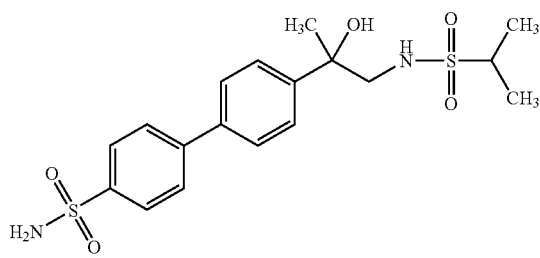

4-bromobenzenesulfonamide (236 mg, 1.0 mmol), the intermediate sulfonyl derivative prepared in example 35 of structure:

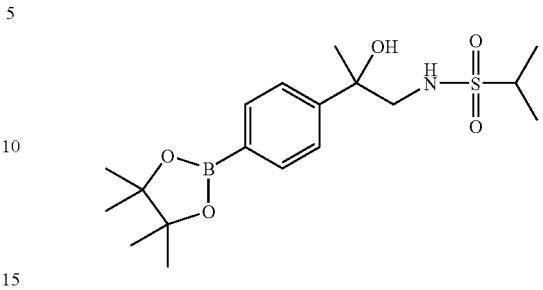

(575 mg, 1.5 mmol), sodium carbonate (1.2 mL of a 2.0 M solution, 1.5 mmol), tetrakis(triphenyl phosphine)palladium (0) (50 mg, 0.65 mmol), and dioxane (20 mL) are mixed together in a 50 mL single neck flask and stirred at 70° C. over night. In the morning, the reaction is cooled to room temperature and poured into H$_2$O and the desired product is extracted with ethyl acetate. The organic layer is back-washed once with H$_2$O, dried over K$_2$CO$_3$, filtered, and concentrated under reduced pressure. This crude material is purified via silica gel chromatography employing the Chromatotron and using a 4000 micron rotor to provide the title compound.

Preparation of Final Title Compound

Scheme I, Step B: Into a 50 mL 3 neck flask fitted with a stirrer and thermometer, 412 mg of 4-[4-(1-hydroxy-1-methyl-2-{[(methylethyl)sulfonyl]amino}ethyl)phenyl]benzenesulfonamide in CH$_2$Cl$_2$ (10 mL) is added dropwise to 0.14 mL DAST in CH$_2$CL$_2$ (10 mL) while stirring at −78° C. under a nitrogen atmosphere. The reaction is allowed to warm to room temperature and diluted with CH$_2$Cl$_2$ (25 mL). This organic layer is washed with H$_2$O, dried over Na$_2$SO$_4$, filtered, and concentrated under reduced vacuum. This crude material is purified via silica gel chromatography employing the Chromatotron and using a 4000 micron rotor with hexane/ethyl acetate eluent to provide the title compound.

EXAMPLE 42

Preparation of N-(2-{3-Fluoro-4'-[1-fluoro-1-methyl-2-(propane-2 Sulfonylamino)ethyl]-biphenyl-4-yl}-ethyl)-isobutyramide

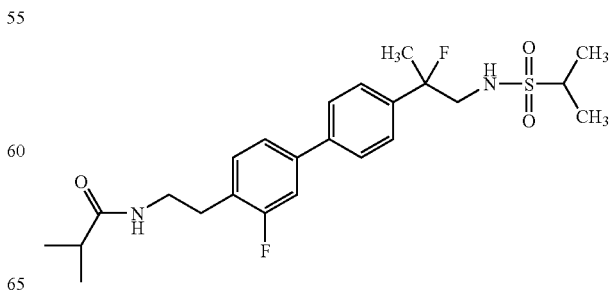

Preparation of
(4-Bromo-2-fluoro-phenyl)-acetonitrile

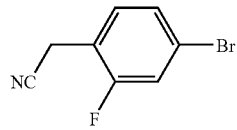

Sodium cyanide (1.37 g, 28.00 mmol) was added to a stirred solution of 2-fluoro-4-bromo benzyl bromide (5.0 g, 18.66 mmol) in dry DMSO (60 mL) at ambient temperature under nitrogen. The reaction was stirred for 4 h at ambient temperature then poured into $H_2O$ (150 mL) and extracted with EtOAc. The organic layer was washed with brine, dried ($MgSO_4$), filtered, and concentrated in vacuo to give the intermediate title compound as a brown oil (3.85 g, 96%). Electrospray mass spectrum: M=213, M+2=215

Preparation of 1-[4-(4,4,5,5-Tetramethyl-[1,3,2]dioxaborolan-2yl)phenylethanone

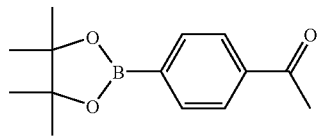

4-Iodo acetophenone (10.00 g, 40.64 mmol), $PdCl_2(dppf) \cdot CH_2Cl_2$ (1.00 g, 1.22 mmol) dry dioxane (160 mL) and $Et_3N$ (17.0 mL, 121.96 mmol) were combined in a dry flask which had been purged with $N_2$ several times. Pinacol borane (8.80 mL, 60.96 mmol) was added and the reaction mixture was heated at reflux for 4 h then cooled to ambient temperature, poured into Diethyl ether (250 mL) and extracted with $H_2O$ and washed with brine. The Diethyl ether was dried ($MgSO_4$), filtered and the filtrate concentrated in vacuo. Purification by gradient chromatography on silica (hexane, 5% EtOAc/hexane) followed by recrystallization (hexane) gave 6.4 g (64%) of the intermediate title compound as a white powder.

Preparation of 2-[4(4,4,5,5-Tetramethyl-[1,3,2]dioxaborolan-2-yl)-phenyl]-2-trimethylsilanyloxy-propionitrile

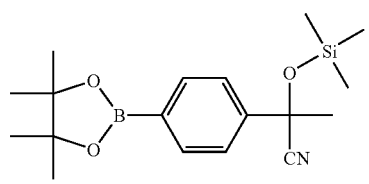

Scheme Va, Step A: 1-[4-(4,4,5,5-Tetramethyl-[1,3,2]dioxaborolan-2yl)phenyl-ethanone (1.0 g, 4.06 mmol) dissolved in THF (1.0 mL) was added to $ZnI_2$ (0.131 g, 0.41 mmol). To this stirred mixture under $N_2$ was added dropwise TMSCN (1.6 mL, 12.18 mmol) and the reaction mixture was stirred at ambient temperature overnight. The resulting mixture was extracted with $NaHCO_3$, $H_2O$, washed with brine, dried ($MgSO_4$), filtered, and concentrated in vacuo to give the intermediate title compound as a yellow oil 0.91 g (65%).

Preparation of 1-Amino-2-[4(4,4,5,5-tetramethyl-[1,3,2]dioxaborolan-2-yl)-phenyl]-propan-2-ol Hydrochloride

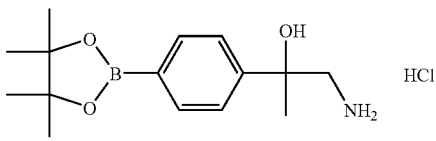

Scheme Va, Step B: Borane dimethyl sulfide 2.0 M (4.0 mL, 8.0 mmol) was added dropwise to 2-[4(4,4,5,5-tetramethyl-[1,3,2]dioxaborolan-2-yl)phenyl]-2-trimethylsilanyloxy-propionitrile (0.910 g, 2.64 mmol) in dry THF (20.0 mL) at ambient temperature. After the initial exotherm, the reaction mixture was heated and stirred at reflux for 4 h cooled to ambient temperature and quenched by a slow addition of concentrated HCl. The reaction was diluted with Diethyl ether and stirred for approximately 1 h. The resulting white precipitate was collected by filtration and used in the next reaction.

Preparation of N-{2-Hydroxy-2-[4(4,4,5,5-tetramethyl-[1,3,2]dioxaboralan-2-yl)phenyl]propyl}-2-propanesulfonamide

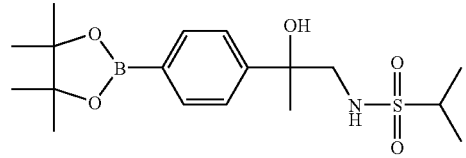

Isopropyl sulfonamide (0.313 g, 2.2 mmol) is added to 1-Amino-2-[4(4,4,5,5-tetramethyl-[1,3,2]dioxaborolan-2-yl)-phenyl]-propan-2-ol hydrochloride (0.627 g, 2.0 mmol) in $CH_2Cl_2$ (20 mL) at 0° C. Triethylamine (0.505 g, 5.0 mmol) is then added and the resulting mixture is stirred for 4 h at 0° C. The reaction mixture is extracted with $H_2O$, washed with brine, dried over magnesium sulfate, filtered, and concentrated in vacuo. The residue is purified by chromatography on silica gel with EtOAc/hexane to provide the intermediate title compound.

Preparation of N-[2-(4'-Cyanomethyl-3'-fluoro-biphenyl-4yl)-2-hydroxy-propyl]-2-propanesulfonamide

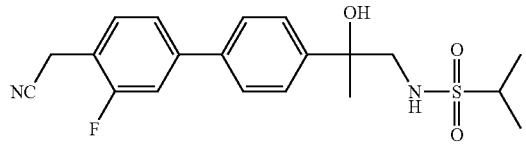

(4-Bromo-2-fluoro-phenyl)-acetonitrile (0.255 g, 1.19 mmol), PdCl₂(dppf).CH₂Cl₂ (0.039 g, 0.048 mmol) and N-{2-hydroxy-2-[4(4,4,5,5-tetramethyl-[1,3,2]dioxaboralan-2-yl)phenyl]propyl}-2-propanesulfonamide (0.383 g, 1.0 mmol) are mixed together in dry DMF (30 mL) under N₂ at ambient temperature. To this stirred mixture is added 2M Na₂CO₃ (1.25 mL, 2.5 mmol) and the resulting mixture is heated and stirred at 80° C. for 6 h. The mixture is cooled and poured into EtOAc. The EtOAc is extracted several times with H₂O, washed with brine, dried (MgSO₄), filtered, and the filtrate evaporated in vacuo. Chromatography on silica gel eluting with EtOAc/hexane gives the intermediate title compound.

Preparation of N-2-[4-(4'-Amino Ethyl-3'-fluorophenyl)phenyl]2-hydroxy-propyl-2-propanesulfonamide

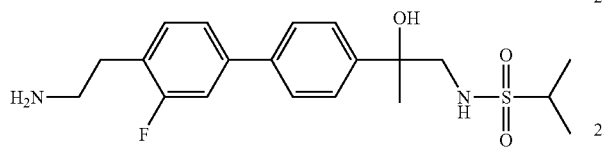

Borane dimethyl sulfide (3.0 mL, 6.0 mmol) is added to N-[2-(4'-cyanomethyl-3'-fluoro-biphenyl-4yl)-2-hydroxy-propyl]-2-propanesulfonamide (0.78 g, 2.0 mmol) in THF (20 mL) and the resulting solution is heated and stirred at reflux for 4 h. The resulting mixture is cooled and acidified cautiously with concentrated HCl. Collection of the precipitated solid by filtration yields the intermediate title compound.

Preparation of N-(2-{3-Fluoro-4'-[1-hydroxy-1-methyl-2-(propane-2-sulfonylamino)-ethyl]-biphenyl-4yl}-ethyl)-isobutyramide

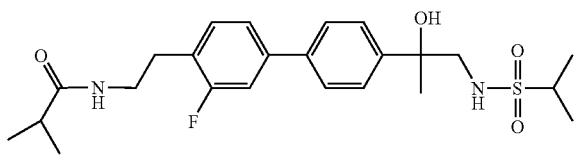

To N-2-[4-(4'-amino ethyl-3'-fluorophenyl)phenyl]2-hydroxy-propyl-2-propanesulfonamide (0.104 g, 0.26 mmol) in dry CH₂Cl₂ in a 12 mL vial is added Et₃N (81 µL, 0.50 mmol), and isobutyryl chloride (34 µL, 0.32 mmol) respectively. The reaction vial is stirred overnight at ambient temperature. The resulting mixture is diluted with CH₂Cl₂ washed successively with 1M HCl, saturated NaHCO₃, brine, dried (MgSO₄), filtered, and concentrated to give the intermediate title compound.

Preparation of Final Title Compound

Scheme I, Step B: To DAST (26 µL, 0.20 mmol) in CH₂Cl₂(0.3 mL) under N₂ at −78° C. is added dropwise N-(2-{3-fluoro-4'-[1-hydroxy-1-methyl-2-(propane-2-sulfonylamino)-ethyl]-biphenyl-4yl}-ethyl)-isobutyramide (0.0928 g, 0.20 mmol) in CH₂Cl₂ (1.0 mL). Following addition the dry ice acetone-cooling bath is replaced with an ice water bath and the reaction mixture allowed to warm to ambient temperature. The reaction mixture is diluted with CH₂Cl₂, extracted with H₂O, dried (Na₂SO₄), filtered, and the filtrate is evaporated to dryness to give the title compound.

EXAMPLE 43

Preparation of N-(2-{3-Fluoro-4'-[1-fluoro-1-methyl-2-(propane-2-sulfonylamino)ethyl]-biphenyl-4-yl}-ethyl)-acetamide

Preparation of N-(2-{3-Fluoro-4'-[1-hydroxy-1-methyl-2-(propane-2-sulfonylamino)ethyl]-biphenyl-4yl}-ethyl)-acetamide

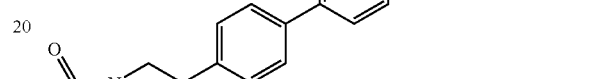

To N-2-[4-(4'-Amino ethyl-3'-fluorophenyl)phenyl]2-hydroxy-propyl-2-propanesulfonamide (0.104 g, 0.26 mmol, intermediate prepared in example 42), in dry CH₂Cl₂ in a 12 mL vial is added Et₃N (81 µL, 0.50 mmol) and acetyl chloride (23 µL, 0.32 mmol) respectively. The reaction vial is stirred overnight at ambient temperature. The resulting mixture is diluted with CH₂Cl₂, washed successively with 1M HCl, saturated NaHCO₃, brine, dried (MgSO₄), filtered, and concentrated to provide the intermediate title compound.

Preparation of Final Title Compound

Scheme I, Step B: To DAST (26 µL, 0.20 mmol) in CH₂Cl₂(0.3 mL) under N₂ at −78° C is added dropwise N-(2-{3-fluoro-4'-[1-hydroxy-1-methyl-2-(propane-2-sulfonylamino)ethyl]-biphenyl-4yl}-ethyl)-acetamide (0.087 g. 0.20 mmol) in CH₂Cl₂(1.0 mL). Following addition the dry ice acetone-cooling bath is replaced with an ice water bath and the reaction mixture allowed to warm to ambient temperature. The reaction mixture is diluted with CH₂Cl₂, extracted with H₂O, dried (Na₂SO₄), filtered, and the filtrate is evaporated to dryness to give the final title compound.

EXAMPLE 44

Preparation of N-{2-(2-Fluoro-2-[3'-fluoro-4'-(2-methanesulfonylamino)-ethyl)-biphenyl-4-yl]propyl}-2-propane Sulfonamide

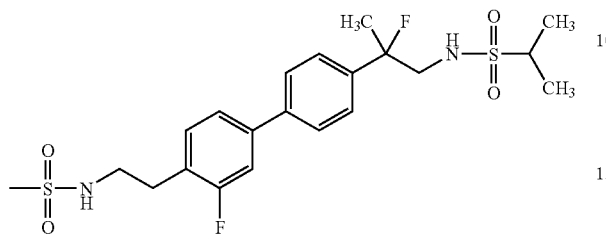

Preparation of N-(2-{3'-Fluoro-4'-[2-methanesulfonylamino)-ethyl]-biphenyl}-2-hydroxy-propyl)-2-propanesulfonamide

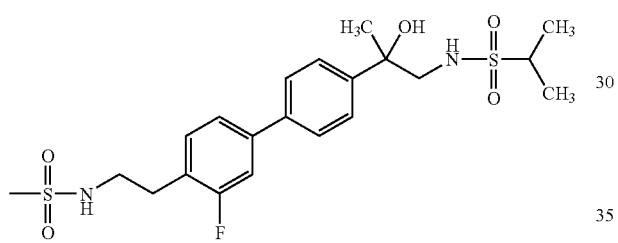

N-2-[4-(4'-Amino ethyl-3'-fluorophenyl)phenyl]2-hydroxy-propyl-2-propanesulfonamide (0.104 g, 0.26 mmol, prepared in example 42), Et₃N (81 µL, 0.50 mmol) and methane sulfonyl chloride (23 µL, 0.30 mmol) are combined with methylene chloride in a 12 mL vial. The reaction vial is stirred overnight at ambient temperature. The resulting mixture is diluted with CH₂Cl₂, washed successively with 1M HCl, saturated NaHCO₃, brine, dried (MgSO₄), filtered, and concentrated to provide the intermediate title compound.

Preparation of Final Title Compound

Scheme I, Step B: To a solution of DAST (26 µL, 0.20 mmol) in CH₂Cl₂ (0.3 mL) under N₂ is added dropwise N-(2-{3'-fluoro-4'-[2-methanesulfonylamino)ethyl]-biphenyl}-2-hydroxy-propyl)-2-propanesulfonamide (0.094 g, 0.20 mmol) in CH₂Cl₂ (1.0 mL) at −78° C. Following addition the dry ice acetone-cooling bath is replaced with an ice water bath and the reaction mixture allowed to warm to ambient temperature. The reaction mixture is diluted with CH₂Cl₂, extracted with H₂O, dried (Na₂SO₄), filtered, and the filtrate is evaporated to dryness to give the final title compound.

EXAMPLE 45

Preparation of N-{2-(2-Fluoro-2-[3'-fluoro-4'-(2-(propane-2-sulfonylamino)-ethyl)-biphenyl-4-yl]propyl}-2-propane Sulfonamide

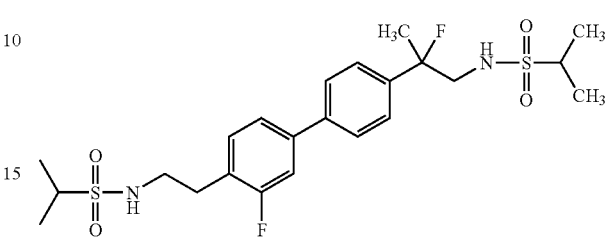

Preparation of N-(2-{3'-Fluoro-4'-[2-(propane-2-sulfonylamino)-ethyl]-biphenyl-4-yl}-2-hydroxy-propyl)-2-propane Sulfonamide

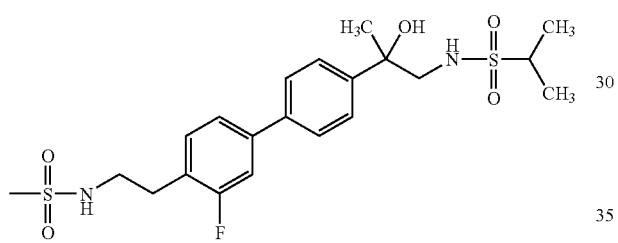

N-2-[4-(4'-Amino ethyl-3'-fluorophenyl)phenyl]2-hydroxy-propyl-2-propanesulfonamide (0.104 g, 0.26 mmol, prepared in example 42), Et₃N (81 µL, 0.50 mmol) and isopropyl sulfonyl chloride (34 µL, 0.30 mmol) are combined with methylene chloride in a 12 mL vial. The reaction vial is stirred overnight at ambient temperature. The resulting mixture is diluted with CH₂Cl₂, washed successively with 1M HCl, saturated NaHCO₃, brine, dried (MgSO₄), filtered, and concentrated to provide the intermediate title compound.

Preparation of Final Title Compound

Scheme I, Step B: To a solution of DAST (26 µL, 0.20 mmol) in CH₂Cl₂ (0.3 mL) under N₂ is added dropwise N-(2-{3'-fluoro-4'-[2-(propane-2-sulfonylamino)-ethyl]-biphenyl}-2-hydroxy-propyl)-2-propanesulfonamide (0.100 g, 0.20 mmol) in CH₂Cl₂ (1.0 mL) at −78° C. Following addition the dry ice acetone-cooling bath is replaced with an ice water bath and the reaction mixture allowed to warm to ambient temperature. The reaction mixture is diluted with CH₂Cl₂, extracted with H₂O, dried (Na₂SO₄), filtered, and the filtrate is evaporated to dryness to give the final title compound.

EXAMPLE 46

Preparation of N-{2-Fluoro-2-[4(2-oxo-2,3-dihydro-1H-indolo-5 yl)-phenyl]-propyl}-2-propane sulfonamide

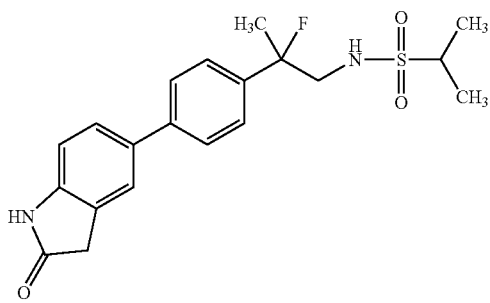

Preparation of 5-Bromo-oxindole

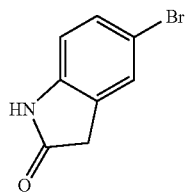

Oxindole (1.30 g, 0.010 mmol) was suspended in dry acetonitrile (22.0 mL) under $N_2$ and cooled to −10° C. To this stirred mixture was added recrystallized NBS (2.00 g, 0.011 mol) portionwise. The resulting suspension was stirred at −10 to 10° C. for 3 h. The precipitated solid was collected by filtration, washed with $H_2O$ and dried to give the intermediate title compound as an off white solid 1.75 g (82%). Electrospray mass spectrum (M−1)=210, (M−1) =211

Preparation of N-{2-Hydroxy-2-[4(2-oxo-2,3-dihydro-1H-indolo-5 yl)-phenyl]-propyl}-2-propane sulfonamide

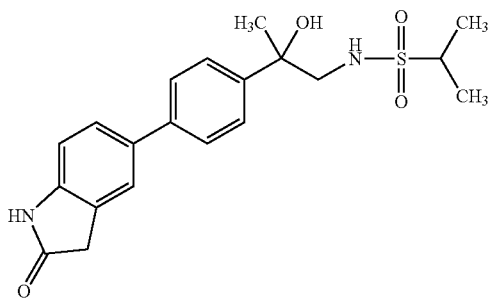

To a stirred mixture of N-{2-hydroxy-2-[4(4,4,5,5-tetramethyl-[1,3,2]dioxaboralan-2-yl)phenyl]propyl}-2-propanesulfonamide (0.383 g, 1.0 mmol, intermediate prepared in example 42), $PdCl_2$(dppf). $CH_2Cl_2$ (0.033 g, 0.04 mmol) and 5-bromo-oxindole (0.276 g, 1.3 mmol) in DMF (20 mL) under $N_2$ is added 2M $Na_2CO_3$ (1.35 mL, 2.7 mmol) and the reaction mixture is heated and stirred under $N_2$ for 6 h. The reaction mixture is allowed to warm to ambient temperature and poured into EtOAc (100 mL). The organic layer is washed with $H_2O$ and brine, dried ($MgSO_4$) filtered and the filtrate evaporated in vacuo. Chromatography on silica gel with EtOAc/hexane gives the intermediate title compound.

Preparation of Final Title Compound

Scheme I, Step B: To a stirred solution of DAST (26 μL, 0.20 mmol) in (0.3 mL) of $CH_2Cl_2$ under $N_2$ at −78° C. is added N-{2-hydroxy-2-[4(2-oxo-2,3-dihydro-1H-indolo-5 yl)-phenyl]-propyl}-2-propane sulfonamide (0.077 g, 0.20 mmol). Following addition the dry ice acetone-cooling bath is replaced with an ice water bath and the reaction mixture allowed to warm to ambient temperature. The reaction mixture is diluted with $CH_2Cl_2$, extracted with $H_2O$, dried ($Na_2SO_4$), filtered, and the filtrate is evaporated to dryness to provide the final title compound.

EXAMPLE 47

Preparation of {4'-[1-Fluoro-1-methyl-2-(propane-2-sulfonylamino)-ethyl]-3-nitro-biphenyl-4-yl}-acetic Acid Ethyl Ester

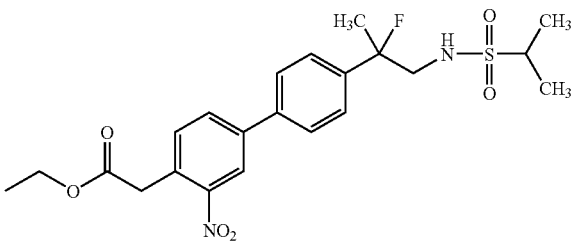

Preparation of 2-(4-Bromo-2-nitro-phenyl)-malonic Acid Diethyl Ester

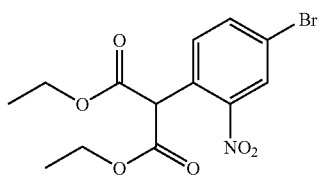

Diethyl malonate (3.34 mL, 22 mmol) was added cautiously to a stirred suspension of 60% NaH (0.96 g, 24 mmol) in dry DMF (50 mL) at −10° C. under $N_2$. The resulting mixture was stirred at −10 to 10° C. for 1 h. To this mixture at 0° C. was added 2,4-dibromo-nitrobenzene (3.34 mL, 0.022 mol) portionwise. The mixture was allowed to warm to ambient temperature and stirred overnight. Evaluation by TLC (EtOAc-hexane 4:1) showed only a trace of starting material. The reaction mixture was poured into a two phase Diethyl ether-1M HCl mixture. The yellow Diethyl ether layer was dried ($MgSO_4$), filtered, and evaporated in vacuo. Chromatography on silica gel, eluting with Preparation of (4-Bromo-2-nitro-phenyl)-acetic Acid Ethyl Ester

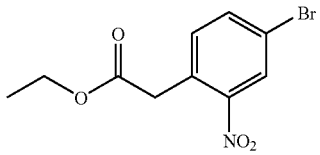

To a stirred solution of concentrated HCl (18.00 mL) diluted to 72.00 mL with 95% Ethanol was added 2-(4-bromo-2-nitro-phenyl)-malonic acid diethyl ester (2.50 g, 6.94 mmol). The resulting mixture was then heated at reflux under $N_2$ for 4 h. The reaction mixture was allowed to cool to ambient temperature and poured into $H_2O$ (250 mL). This aqueous mixture was then extracted with 2×150 mL of Diethyl ether. The $Et_2O$ layer was extracted with $H_2O$ and 5% $NaHCO_3$ washed with brine, dried ($MgSO_4$), and filtered. Evaporation of the filtrate in vacuo gave the intermediate title compound as a yellow liquid (1.52 g, 76%).

Preparation of {4'-[1-Hydroxy-1-methyl-2-(propane-2-sulfonylamino)-ethyl]-3-nitro-biphenyl-4-yl}-acetic Acid Ethyl Ester

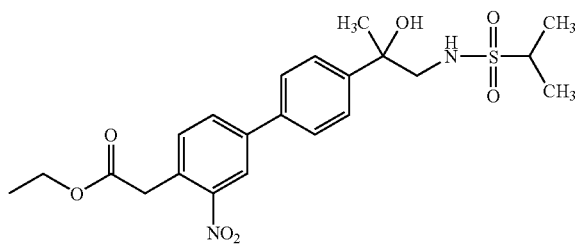

$PdCl_2(dppf).CH_2Cl_2$ (0.077 g, 0.90 mmol) and N-{2-hydroxy-2-[4(4,4,5,5-tetramethyl-[1,3,2] dioxaboralan-2-yl)phenyl]propyl}-2-propanesulfonamide (0.383, 1.0 mmol, intermediate prepared in example 42) are mixed together in a dry flask under $N_2$ followed by (4-bromo-2-nitro-phenyl)-acetic acid ethyl ester (0.300 g, 1.04 mmol), $CsCO_3$ (0.68 g, 2.09 mmol) and toluene(65 mL) respectively. The resulting mixture is heated and stirred at 96° C. for 5 h. The reaction mixture is allowed to cool to ambient temperature and is stirred overnight. The toluene is diluted with EtOAc (100 mL) and filtered through celite. The resulting filtrate is extracted with 2×200 mL of $H_2O$, washed with brine, dried ($MgSO_4$), and filtered. The filtrate is evaporated and chromatographed on silica gel, eluting with EtOAc-hexane to give the intermediate title compound.

Preparation of Final Title Compound

Scheme I, Step B: To a solution of DAST (118 µL, 0.998 mmol) in $CH_2Cl_2$ (0.8 mL) under $N_2$ at −78° C. is added {4'-[1-hydroxy-1-methyl-2-(propane-2-sulfonylamino)-ethyl]-3-nitro-biphenyl-4-yl}-acetic acid ethyl ester (0.465 g, 1.00 mmol) in $CH_2Cl_2$ (3.0 mL). Following addition the dry ice acetone-cooling bath is replaced with an ice water bath and the reaction mixture allowed to warm to ambient temperature. The reaction mixture is diluted with $CH_2Cl_2$, extracted with $H_2O$, dried ($Na_2SO_4$), filtered, and the filtrate is evaporated to dryness to provide the final title compound.

EXAMPLE 48

Preparation of {4'-[1-Fluoro-1-methyl-2-(propane-2-sulfonylamino)-ethyl]-3-nitrobiphenyl-4-yl}-acetic Acid

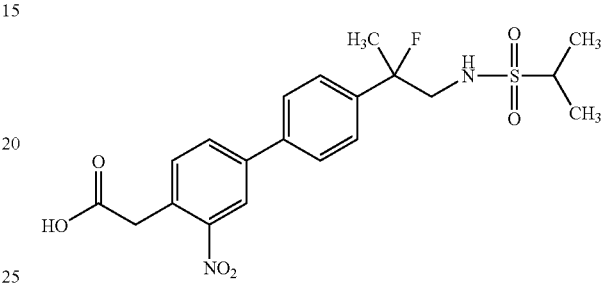

To a solution of {4'-[1-fluoro-1-methyl-2-(propane-2-sulfonylamino)-ethyl]-3-nitro-biphenyl-4-yl}-acetic acid ethyl ester. (0.341 g, 0.731 mmol, prepared in example 47) in Ethanol (5.0 mL) is added a solution of 6.7% NaOH (15.0 mL) and the resulting mixture is stirred under $N_2$ at ambient temperature for 72 h. The mixture is diluted with $H_2O$ (100 mL) and acidified with 37% HCl. Extraction with EtOAc followed by drying ($MgSO_4$), filtration, and evaporation of the filtrate in vacuo gives the title compound.

EXAMPLE 49

Preparation of N-{2-Fluoro-2-[4-(2-oxo-2,3-dihydro-1H-indol-6-yl)-phenyl]-propyl}-2-propanesulfonamide

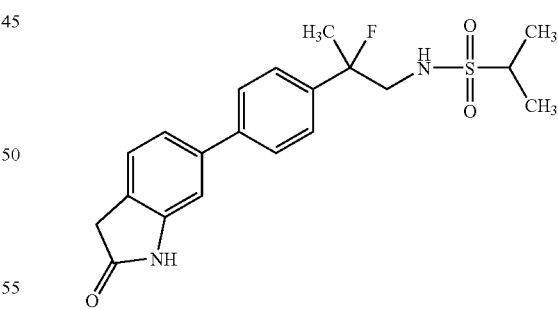

To a stirred solution of {4'-[1-fluoro-1-methyl-2-(propane-2-sulfonylamino)ethyl]-3-nitro-biphenyl-4-yl}-acetic acid (0.311 g, 0.71 mmol, prepared in example 48) dissolved in Ethanol (4.0 mL)/50% $H_2SO_4$ (3.0 mL) at ambient temperature then heated to 90° C. is added Zn (0.186 g, 2.84 mmol) in divided portions over 30 minutes. Heating and stirring is continued for 2 h after addition of the Zn. The mixture is allowed to cool to ambient temperature. It is then extracted (EtOAc) and the EtOAc is extracted with 5% $NaHCO_3$, washed with brine, dried ($MgSO_4$), filtered and the filtrate concentrated in vacuo. Chromatography of the residue (silica gel, EtOAc/hexane) provides the title compound.

EXAMPLE 50

Preparation of Methyl 6-{N-[4-(1-Fluoro-1-methyl-2-{[(methylethyl)sulfonyl]amino}ethyl)phenyl]carbamoyl}pyridine-3-carboxylate

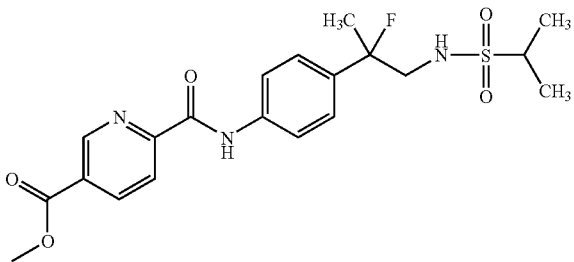

Preparation of Methyl 6-{N-[4-(1-Hydroxy-1-methyl-2-{[(methylethyl)sulfonyl]amino}ethyl)phenyl]carbamoyl}pyridine-3-carboxylate

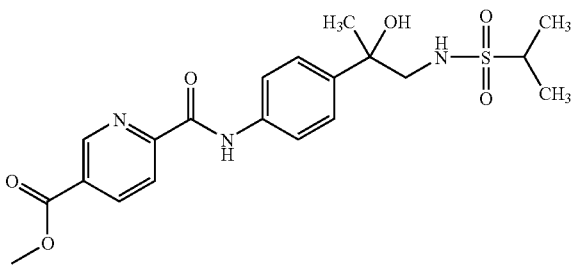

Scheme XII, Step A: Into a 50 mL single neck flask, 1 mL oxalyl chloride was added syringe wise to 5-(methoxycarbonyl)-pyridine-2-carboxylic acid (271 mg, 1.5 mmol) in methylene chloride (10 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into THF (5 mL) and added dropwise to a stirring solution of [2-(4-aminophenyl)-2-hydroxypropyl][(methylethyl)sulfonyl]amine (400 mg, 1.5 mmol, intermediate prepared in example 19) and triethylamine (152 mg) in THF (20 mL) at room temperature and the mixture was stirred overnight. In the morning, the solution was concentrated under reduced vacuum and the resulting oil was taken into methylene chloride and the organic layer was washed once with H₂O, dried over K₂CO₃, filtered, and concentrated under reduced vacuum to yield 244 mg as an orange solid. This material was purified via silica gel chromatography employing the chromatotron and using a 4000 micron rotor while eluting with a solvent of ethyl acetate to yield the intermediate title compound (165 mg, 25%) as a yellow solid. Ion spray M.S. 434.2 (M*−1).

Calculated for $C_{20}H_{25}N_3O_6S—H_2O$:

| Theory: | C 52.95, H 6.00, N 9.27. |
| Found: | C 53.14, H 5.67, N 9.01. |

Preparation of Final Title Compound

Scheme XII, Step B: Into a 50 mL, 3 necked flask fitted with a stirrer and thermometer, 200 mg of methyl 6-{N-[4-(1-hydroxy-1-methyl-2-{[(methylethyl)sulfonyl]amino}ethyl)phenyl]carbamoyl}pyridine-3-carboxylate in methylene chloride (5 mL) is added dropwise to 0.06 mL DAST in methylene chloride (5 mL) while stirring at −78° C. under a nitrogen atmosphere. Reaction is allowed to warm to room temperature and diluted with methylene chloride (25 mL). This organic layer is washed with H₂O, dried over Na₂SO₄, filtered, and concentrated under reduced vacuum to yield a slowly crystallizing yellow oil (80% yield). This material was used without further purification. Ion spray M.S. 436.3 (M*−1).

Calculated for $C_{20}H_{24}N_3O_5SF$:

| Theory: | C 54.91, H 5.53, N 9.60. |
| Found: | C 54.10, H 5.66, N 9.12. |

EXAMPLE 51

Preparation of 6-{N-[4-(1-Fluoro-1-methyl-2-{[(methylethyl)sulfonyl]amino}ethyl)phenyl]carbamoyl}pyridine-3-carboxylic Acid

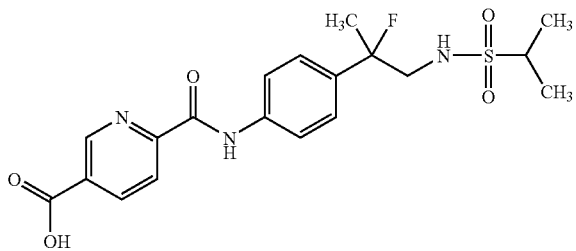

Methyl 6-{N-[4-(1-fluoro-1-methyl-2-{[(methylethyl)sulfonyl]amino}ethyl)phenyl]carbamoyl}pyridine-3-carboxylate (150 mg, 0.35 mmol, prepared in example 50), lithium hydroxide (52 mg, 1.24 mmol), tetrahydrofuran (6 mL), methanol (2 mL), and water (2 mL) were mixed together in a 25 mL 3 neck flask and stirred over night at room temperature. In the morning, the mixture was concentrated under reduced vacuum to yield a white solid. This material was taken into 1N HCl and the desired material was extracted into methylene chloride. The acidic solution was taken to pH 10 with 1N NaOH and the resulting precipitate was again extracted with methylene chloride. Both organic layers were combined and washed once with H₂O, dried over MgSO₄, filtered, and concentrated under reduced vacuum to yield the title compound (125 mg, 84%) as a tan solid. This material was used without further purification. Ion spray M.S. 403.9 (M*−19 Fluorine).

EXAMPLE 52

Preparation of N-[4-(1-Fluoro-1-methyl-2-{[(methylethyl)sulfonyl]amino}ethyl)phenyl][5-(N-methylcarbamoyl)(2-pyridyl)]carboxamide

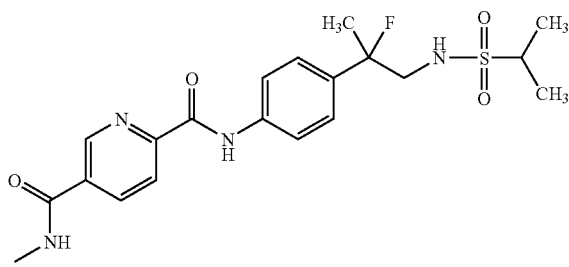

Into a 50 mL single neck flask, 1 mL oxalyl chloride was added syringe wise to 6-{N-[4-(1-fluoro-1-methyl-2-{[(methylethyl)sulfonyl]amino}ethyl)phenyl]carbamoyl}pyridine-3-carboxylic acid. (110 mg, 0.26 mmol, prepared in example 51) in methylene chloride (10 mL) while stirring under nitrogen at room temperature. Immediately, 1 drop of DMF was added by pipette initiating a foaming of the mixture. The reaction was stirred one hour at this temperature and then concentrated under reduced vacuum to yield a white semi-solid. This material was placed into dioxane (10 mL) and added dropwise to a stirring solution of 40% methylamine in water (3 mL, excess) at room temperature and the mixture was stirred overnight. In the morning, the solution was concentrated under reduced vacuum and the resulting oil was taken into methylene chloride and the organic layer was washed once with $H_2O$, dried over $K_2CO_3$, filtered, and concentrated under reduced vacuum to yield 78 mg as an oil. This material was purified via silica gel chromatography employing the chromatotron and using a 1000 micron rotor while eluting with a solvent of ethyl acetate to yield the title compound (28 mg, 25%) as a white solid. Ion spray M.S. 435.2 (M*–1) and 417.1 (M*–19 Fluorine).

Calculated for $C_{20}H_{25}N_4O_4SF$:

| | |
|---|---|
| Theory: | C 55.03, H 5.77, N 12.83. |
| Found: | C 55.85, H 6.09, N 12.02. |

EXAMPLE 53

Preparation of Propane-2-sulfonic Acid [2-Fluoro-2-(2-fluoro-4-methoxy-phenyl)propyl]-amide

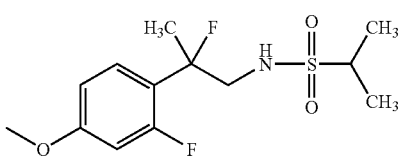

Preparation of 2-(2-Fluoro-4-methoxy-phenyl)-2-trimethylsilanyloxy-propionitrile

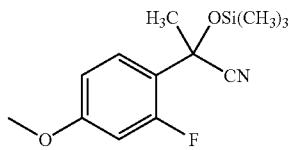

Scheme IV, Step A: 2'-Fluoro-4'-methoxy acetophenone (2.0 g, 11.89 mmol) was combined with zinc iodide (0.38 g, 1.19 mmol) in a 50 mL round bottom flask. Trimethylsilyl cyanide (4.8 mL, 35.67 mmol) was slowly added dropwise to the solid mixture, with the generation of heat. The resulting dark brown solution was stirred at room temperature under nitrogen overnight. The mixture was diluted with $CHCl_3$ and washed with $NaHCO_3$, water and brine, dried ($MgSO_4$), filtered, and concentrated to a yellow oil that was used in the next step without purification.

Preparation of 2-(2-Fluoro-4-methoxy-phenyl)-2-hydroxy-propylamine Hydrochloride

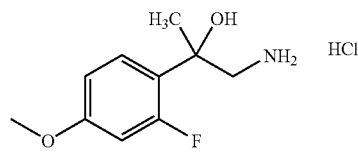

Scheme IV, Step B: 2-(2-Fluoro-4-methoxy-phenyl)-2-trimethylsilanyloxy-propionitrile (2.8 g, 10.47 mmol) was dissolved in dry THF (30 mL) and stirred at room temperature under nitrogen. A 2.0 M solution of borane-dimethylsulfide complex (15.7 mL, 31.41 mmol) was added dropwise and the reaction was heated at reflux for 3 hours then cooled to room temperature. Concentrated HCl was carefully added dropwise until the evolution of gas ceased. The reaction mixture was diluted with diethyl ether and a white precipitate formed. The solids were collected and washed with additional ether to give 2.5 g (100%) of 2-(2-fluoro-4-methoxy-phenyl)-2-hydroxy-propylamine hydrochloride. Electrospray mass spectrum (M–1)=199.99 (free amine)

Preparation of Propane-2-sulfonic Acid [2-(2-Fluoro-4-methoxy-phenyl)-2-hydroxy-propyl]-amide

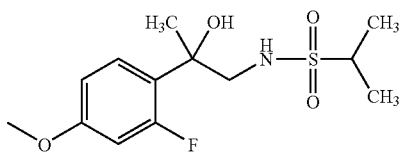

Scheme I, Step A: 2-(2-Fluoro-4-methoxy-phenyl)-2-hydroxy-propylamine hydrochloride was converted to the free base by partitioning between ethyl acetate and 1 M NaOH. The amine (1.0 g, 5.02 mmol) was combined with propane-2-sulfonic acid benzotriazol-1-yl ester (1.3 g, 5.52 mmol) in DMF (25 mL) and heated at 120° C. for 2 hr. then cooled to room temperature. The reaction mixture was diluted with ethyl acetate and extracted with 1 M HCl. The organic layer was separated and washed with water and saturated NaCl, dried (MgSO$_4$), filtered, and concentrated to a yellow oil which was used in the next step without purification.

Preparation of Final Title Compound

Scheme I, Step B: A dry CH$_2$Cl$_2$ solution (10 mL) of (diethylamino)sulfur trifluoride (DAST) (0.419 mL, 3.17 mmol) was cooled to −78° C. while stirring under N$_2$. A CH$_2$Cl$_2$ solution (5 mL) of propane-2-sulfonic acid [2-(2-fluoro-4-methoxyphenyl)-2-hydroxy-propyl]-amide (0.79 g, 2.64 mmol) was added dropwise via syringe and the reaction was immediately brought to 0° C. The reaction was quenched with water and diluted with diethyl ether. The organic layer was separated and washed with water and saturated NaCl solution, dried (MgSO$_4$), filtered, and concentrated to a yellow oil. The crude residue was purified by silica gel chromatography, eluting with 30% ethyl acetate/hexanes, to provide the final title compound, propane-2-sulfonic acid [2-fluoro-2-(2-fluoro-4-methoxy-phenyl)-propyl]-amide, (0.52 g, 64%) as a light yellow oil.

$^1$HNMR (CDCl$_3$) δ 1.20–1.22 (6H, d), 1.24–1.26 (6H, d), 1.68–1.73 (1H, d), 3.25 (1H, sept), 3.58–3.66 (2H, m), 3.80 (3H, s), 4.20 (1H, t), 6.60 (1H, m), 6.73 (1H, m), 7.36 (1H, t).

The following Table I specifically illustrates additional preferred substituents for R$^1$ Table I.

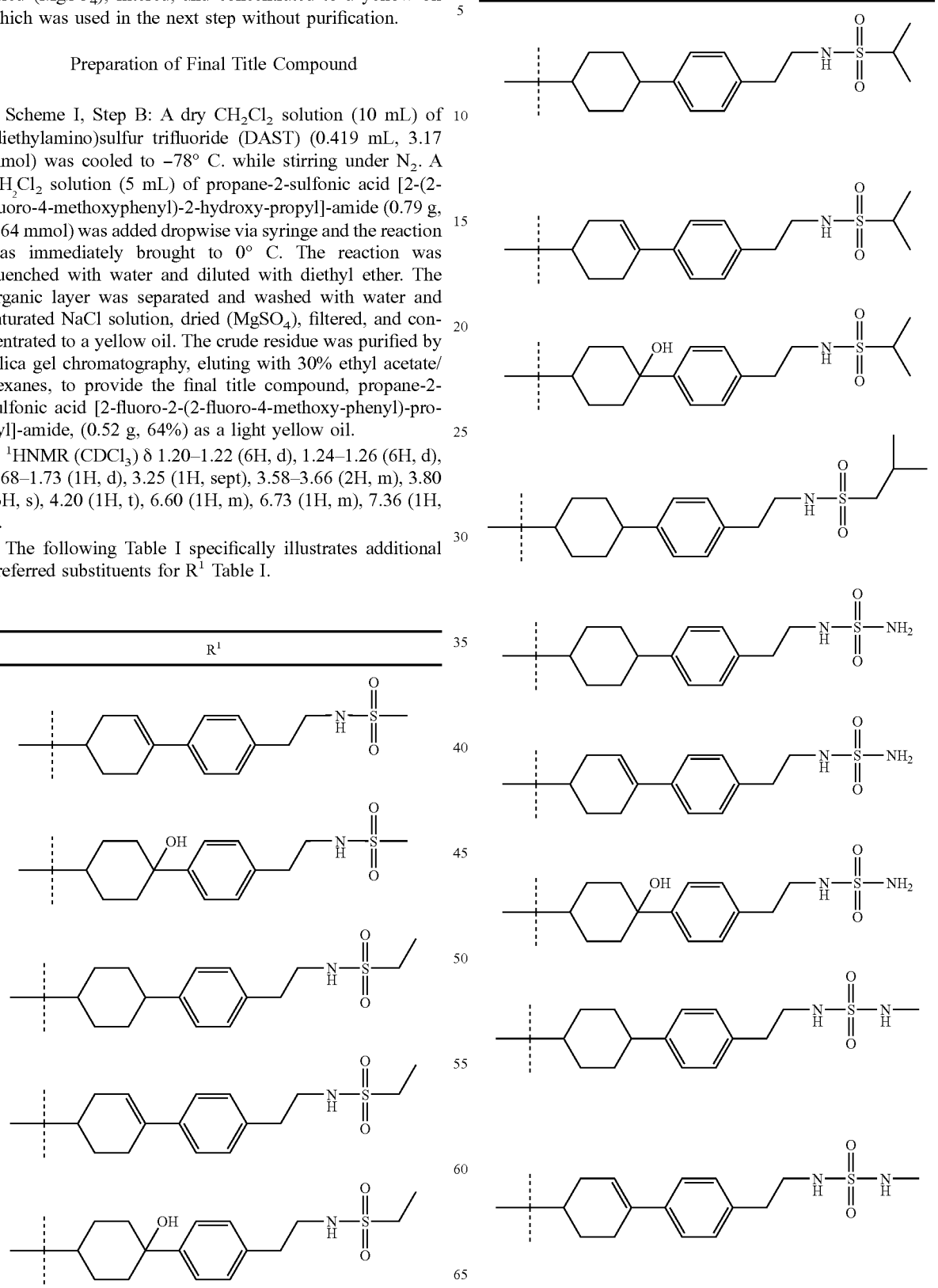

-continued
R¹
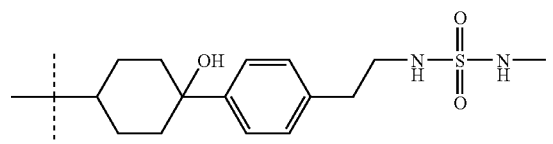
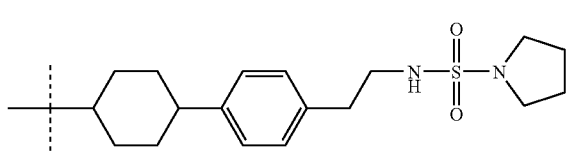
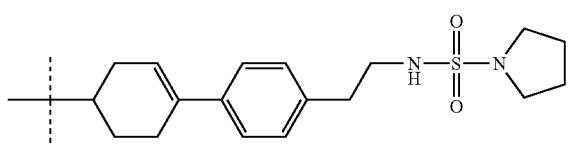
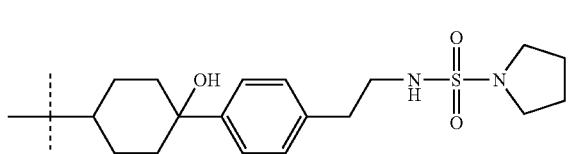
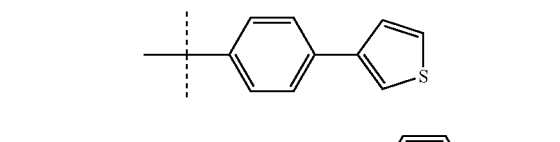
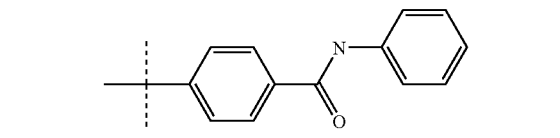
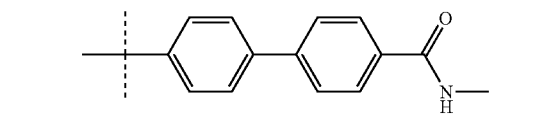
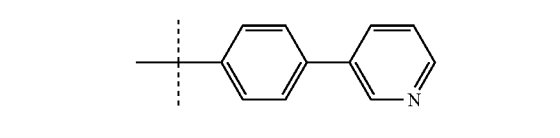
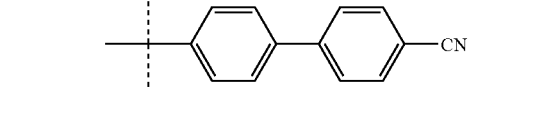
-continued
R¹
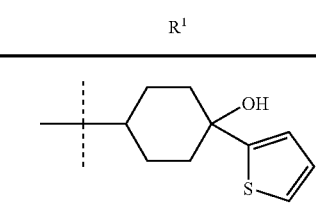
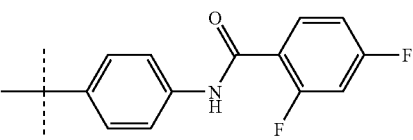
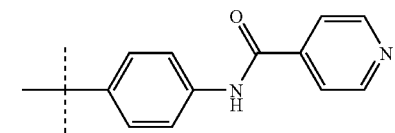
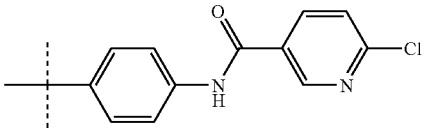
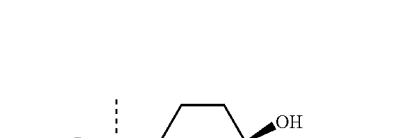
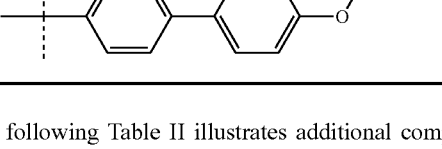
The following Table II illustrates additional compounds of the present invention. The following compounds can be prepared by one of ordinary skill in the art in a manner analogous to the techniques and procedures described hereinabove. The starting materials and reagents are readily available to one of ordinary skill in the art.

TABLE II

| Example | Compound |
|---|---|
| 54 | 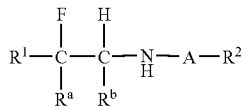 |
| 55 | |
| 56 | |
| 57 | |
| 58 | |

We claim:
1. A compound of the formula:

$$R^1-\underset{R^a}{\underset{|}{\overset{F}{\overset{|}{C}}}}-\underset{R^b}{\underset{|}{\overset{H}{\overset{|}{C}}}}-\underset{H}{\overset{}{N}}-A-R^2$$

wherein:
A represents SO₂;
Rᵃ represents (1–6C)alkyl, (2–6C)alkenyl, —(1–4C)alkyl(3–8C)cycloalkyl, or —(1–4C)alkylaromatic:
Rᵇ represents H, (1–6C)alkyl, (2–6C)alkenyl, —(1–4C)alkyl(3–8C)cycloalkyl, or —(1–4C)alkylaromatic; or
Rᵃ and Rᵇ together with the carbon atoms to which they are attached form a (3–8C) saturated carbocyclic ring, a (3–8C) saturated carbocyclic ring containing a heteroatom selected from the group consisting of sulfur or oxygen, or a (5–8C) carbocyclic ring containing one double bond;
R¹ represents an unsubstituted or substituted aromatic group, an unsubstituted or substituted heteroaromatic group, or an unsubstituted or substituted (5–8C)cycloalkyl group;
R² represents (1–6C)alkyl, (3–6C)cycloalkyl, (1–6C)fluoroalkyl, (1–6C)chloroalkyl, (2–6C)alkenyl, (1–4C)alkoxy(1–4C)alkyl, phenyl which is unsubstituted or substituted by halogen, (1–4C)alkyl or (1–4C)alkoxy, or when A represents SO₂, a group of formula R³R⁴N in which R³ and R⁴ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group;
or a pharmaceutically acceptable salt thereof.

2. A compound according to claim 1 wherein R¹ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo(1–10C)alkyl; (CH²)ᵧX¹R⁹ in which y is 0 or an integer of from 1 to 4, X¹ represents O, S, NR¹⁰, CO, COO, OCO, CONR¹¹, NR¹²CO, NR¹²COCOO or OCONR¹³, R⁹ represents hydrogen, (1–10C)alkyl, (3–10C)alkenyl, (3–10C)alkynyl, pyrrolidinyl, tetrahydrofuryl, morpholino or (3–8C)cycloalkyl and R¹⁰, R¹¹, R¹² and R¹³ each independently represents hydrogen or (1–10C)alkyl, or R⁹ and R¹⁰, R¹¹, R¹² or R¹³ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl;

dihydrothiazolyl; (1–4)alkoxycarbonyldihydrothiazolyl; (1–4C)alkoxycarbonyldimethyldihydro-thiazolyl; tetrahydro-thienyl; tetrahydrofuryl; tetrahydrothiopyranyl: tetrahydropyranyl; indolyl; benzofuryl; benzothienyl; benzimidazolyl; and a group of formula $R^{14}—(L^a)_n—X^2—(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C) alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C) alkynyl, (3–8C)cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

3. A compound according to claim 2 wherein $R^2$ represents (1–6C)alkyl, (3–6C)cycloalkyl, fluoro(1–6C)alkyl, chloro(1–6C)alkyl, (2–6C)alkenyl 1–4C)alkoxy(1–4C) alkyl, heteroaromatic, or phenyl which is unsubstituted or substituted by halogen, (1–4C)alkyl or (1–4C)alkoxy.

4. A compound according to claim 3 wherein $R^2$ represents (1–6C)alkyl, (3–6C)cycloalkyl or heteroaromatic, or phenyl which is unsubstituted or substituted by halogen, (1–4C)alkyl or (1–4C)alkoxy.

5. A compound according to claim 4 wherein $R^2$ represents methyl, ethyl, isopropyl, t-butyl, cyclopropyl, cyclobutyl, cyclopentyl, cyclohexyl, isovaleryl, phenyl, benzyl, 2-furyl, 2-thienyl, 5-oxazoyl, 2-pyridyl, 3-pyridyl, or 4-pryidyl.

6. A compound according to claim 5 wherein $R^a$ represents (1–6C)alkyl or (2–6C)alkenyl.

7. A compound according to claim 6 wherein $R^a$ represents methyl, ethyl, propyl, n-butyl, sec-butyl, tert-butyl, pentyl or hexyl.

8. A compound according to claim 7 wherein $R^a$ represents methyl.

9. A compound according to claim 8 wherein $R^b$ represents H, (1–6C)alkyl, or (2–6C)alkenyl.

10. A compound according to claim 8 wherein $R^b$ represents H.

11. A compound according to claim 8 wherein $R^1$ is selected from the group consisting of

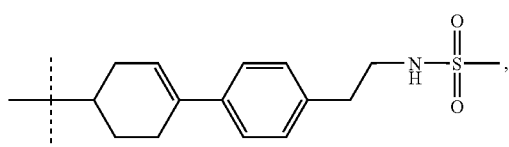
a

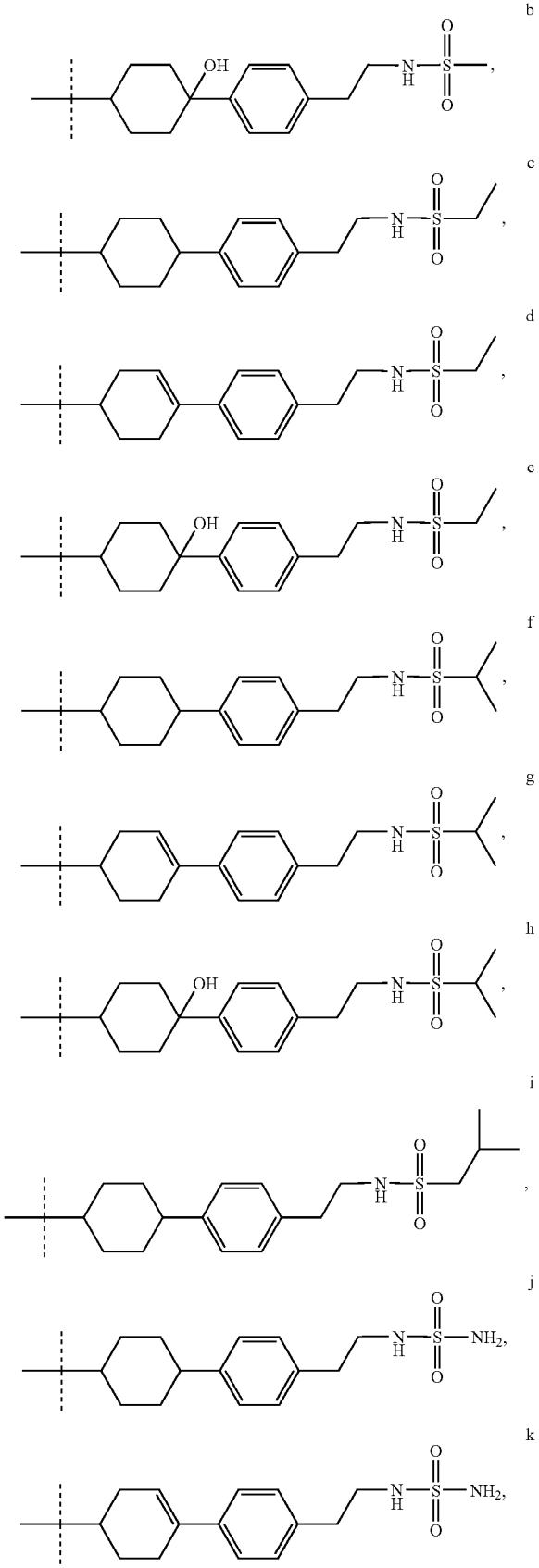

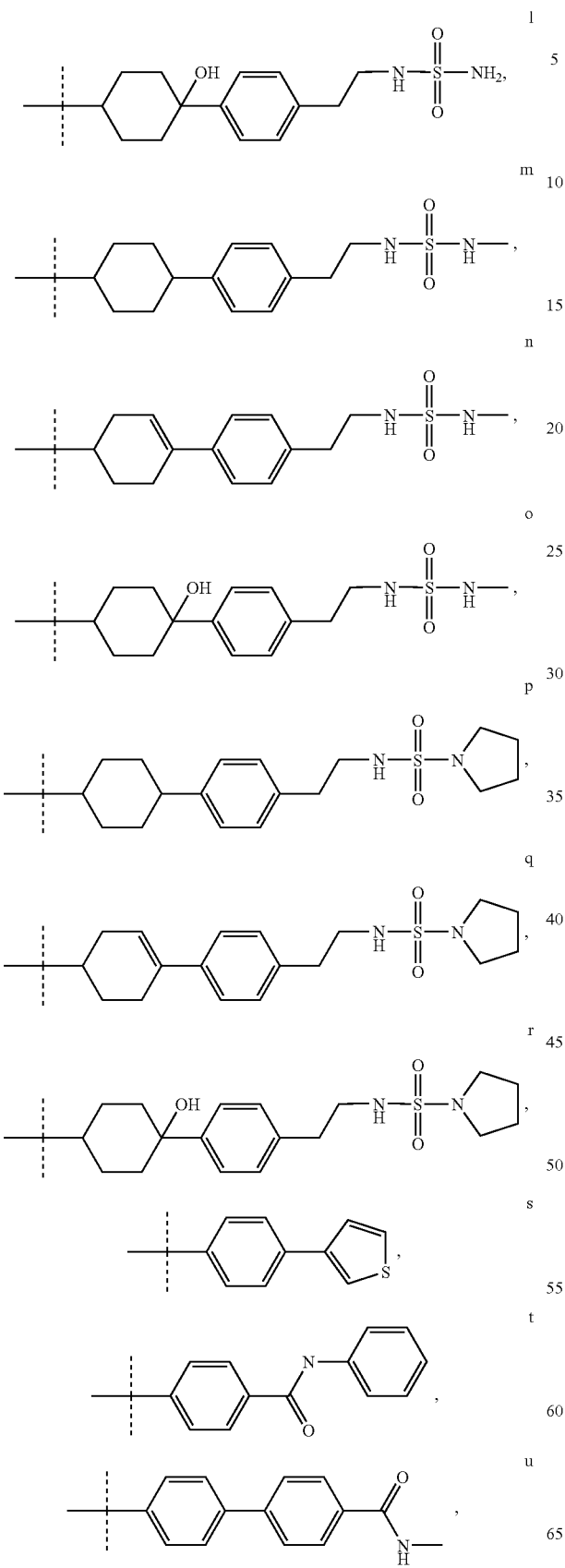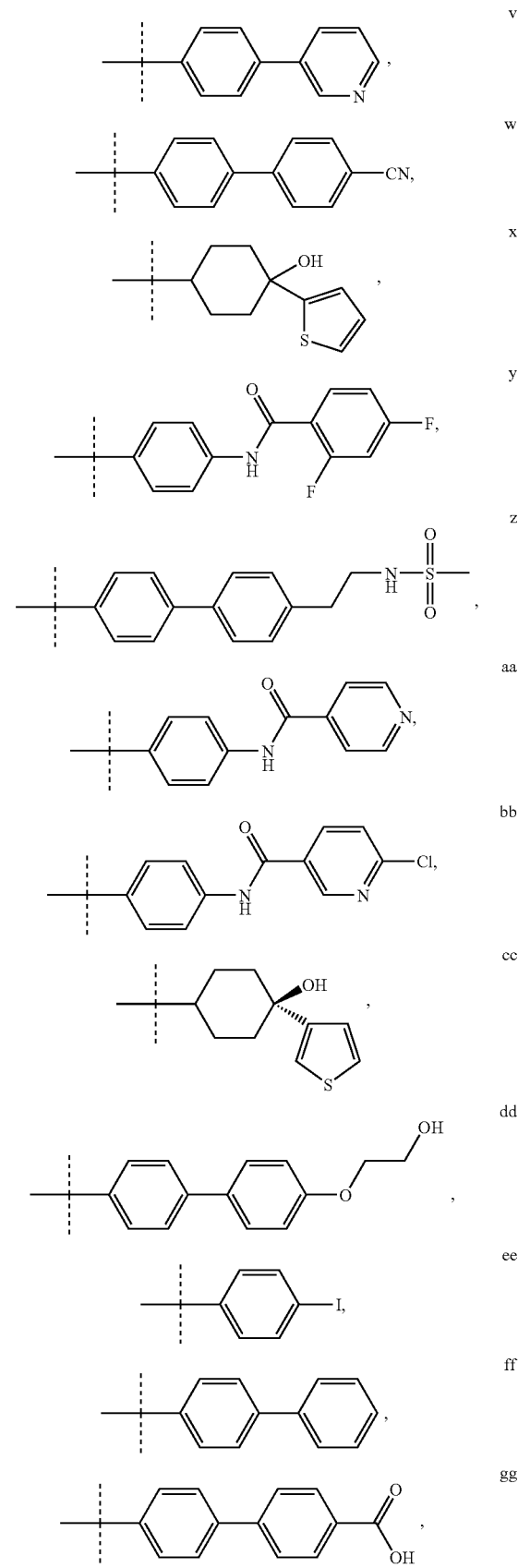

-continued

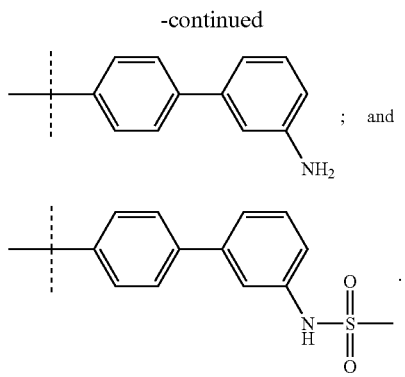

12. A compound selected from the group consisting of:
[2-fluoro-2-(4-iodophenyl)propyl][(methylethyl)sulfonyl]amine;
[2-fluoro-2-(4-phenylphenyl)propyl][(methylethyl)sulfonyl]amine;
4-[4-(1-fluoro-1-methyl-2-{[(methylethyl)sulfonyl]amino}ethyl)phenyl]benzenecarbonitrile;
4-[4-(1-fluoro-1-methyl-2-{[(methylethyl)sulfonyl]amino}ethyl)phenyl]benzoic acid;
{2-[4-(3-aminophenyl)phenyl]-2-fluoropropyl}[(methylethyl)sulfonyl]amine;
[2-fluoro-2-(40{3-[(methylsulfonyl)amino]phenyl}phenyl)propyl][(methylethyl)sulfonyl]amine;
[2-fluoro-2-(4-(3-thienyl)phenyl)propyl][(methylethyl)sulfonyl]amine;
[2-fluoro-2-(4-3-pyridyl)phenyl)propyl][(methylethyl)sulfonyl]amine;
2-{4-[4-(1-fluoro-1-methyl-2-{[(methylethyl)sulfonyl]amino}ethyl)phenyl]phenyl}ethanenitrile;
4-[4-(1-fluoro-1-methyl-2-{[(methylethyl)sulfonyl]amino}ethyl)phenyl]benzaldehyde;
{4-[4-(1-fluoro-1-methyl-2-{[(methylethyl)sulfonyl]amino}ethyl)phenyl]phenyl}-N-methylcarboxamide;
{4-[4-(1-fluoro-1-methyl-2-{[(methylethyl)sulfonyl]amino}ethyl)phenyl]phenyl}-N,N-dimethylcarboxamide;
N-ethyl{4-[4-(1-fluoro-1-methyl-2-{[(methylethyl)sulfonyl]amino}ethyl)phenyl]phenyl}carboxamide;
4-[4-(1-fluoro-1-methyl-2-{[(methylethyl)sulfonyl]amino}ethyl)phenyl]phenyl pyrrolidinyl ketone;
N-{3-[4-(1-fluoro-1-methyl-2-{[(methylethyl)sulfonyl]amino}ethyl)phenyl]phenyl}acetamide;
N-{3-[4-(1-fluoro-1-methyl-2-{[(methylethyl)sulfonyl]amino}ethyl)phenyl]phenyl}propanamide;
N-{3-[4-(1-fluoro-1-methyl-2-{[(methylethyl)sulfonyl]amino}ethyl)phenyl]phenyl}butanamide;
amino-N-{3-[4-(1-fluoro-1-methyl-2-{[(methylethyl)sulfonyl]amino}ethyl)phenyl]phenyl}amide;
N-[4-(1-fluoro-1-methyl-2-{[(methylethyl)sulfonyl]amino}ethyl)phenyl]benzamide;
(3-cyanophenyl)-N-[4-(1-fluoro-1-methyl-2-{[(methylethyl)sulfonyl]amino}ethyl)phenyl]carboxamide;
N-[4-(1-fluoro-1-methyl-2-{[(methylethyl)sulfonyl]amino}ethyl)phenyl]-4-pyridylcarboxamide;
N-[4-(1-fluoro-1-methyl-2-{[(methylethyl)sulfonyl]amino}ethyl)phenyl]{4-[2(methoxycarbonylamino)ethyl]phenyl}carboxamide;
(2-{4-[(3,5-difluorophenyl)methoxy]phenyl}-2-fluoropropyl)[(methylethyl)sulfonyl]amine;
{2-fluoro-2-[4-(4-{2[(methylsulfonyl)amino]ethyl}phenyl)phenyl]propyl}[(methylethyl)sulfonyl]amine;
(4-chlorophenyl)-N-[4-(1-fluoro-1-methyl-2-{[(methylethyl)sulfonyl]amino}ethyl)phenyl]carboxamide;
(6-chloro(3-pyridyl))-N-[4-(1-fluoro-1-methyl-2-{[(methylethyl)sulfonyl]amino}ethyl)phenyl]carboxamide;
(4-cyanophenyl)-N-[4-(1-fluoro-1-methyl-2-{[(methylethyl)sulfonyl]amino}ethyl)phenyl]carboxamide;
ethoxy-N-[4-(1-fluoro-1-methyl-2-{[(methylethyl)sulfonyl]amino}ethyl)phenyl]carboxamide;
N-[4-(1-fluoro-1-methyl-2-{[(methylethyl)sulfonyl]amino}ethyl)phenyl]isoxazol-5-ylcarboxamide;
4-(dimethylamino)-N-[4-(1-fluoro-1-methyl-2-{[(methylethyl)sulfonyl]amino}ethyl)phenyl]butanamide;
N-[4-(1-fluoro-1-methyl-2-{[(methylethyl)sulfonyl]amino}ethyl)phenyl]-3-thienylcarboxamide;
{2-fluoro-2-[4-(phenylmethoxy)phenyl]propyl}[(methylethyl)sulfonyl]amine;
2-{[4-(1-fluoro-1-methyl-2-{[(methylethyl)sulfonyl]amino}ethyl)phenoxy]methyl}benzenecarbonitrile;
[2-fluoro-2-(4-methoxyphenyl)propyl][(methylethyl)sulfonyl]amine;
{2-[4-(3,5-difluorophenyl)phenyl]-2-fluoropropyl}[(methylethyl)sulfonyl]amine;
[(dimethylamino)sulfonyl][2-fluoro-2-(4-iodophenyl)propyl]amine;
4-[4-(2-{[(dimethylamino)sulfonyl]amino}-1-fluoro-isopropyl)phenyl]benzenecarbonitrile;
{2-[4-(3-aminophenyl)phenyl]-2-fluoropropyl}[(dimethylamino)sulfonyl]amine;
[(dimethylamino)sulfonyl][2-fluoro-2-(4-{3-[(methylsulfonyl)amino]phenyl}phenyl)propyl]amine;
[(dimethylamino)sulfonyl]{2-fluoro-2-[4-(3-{[(methylethyl)sulfonyl]amino}phenyl)phenyl]propyl}amine;
4-[4-(1-fluoro-1-methyl-2-{[(methylethyl)sulfonyl]amino}ethyl)phenyl]benzenesulfonamide;
N-(2-{3-fluoro-4'-[1-fluoro-1-methyl-2-(propane-2 sulfonylamino)-ethyl]biphenyl-4-yl}-ethyl)-isobutyramide;
N-(2-{3-fluoro-4'-[1-fluoro-1-methyl-2-(propane-2-sulfonylamino)-ethyl]-biphenyl-4-yl}-ethyl)-acetamide;
N-{2-(2-fluoro-2-[3'-fluoro-4'-(2-methanesulfonylamino)-ethyl)-biphenyl-4-yl]propyl}-2-propane sulfonamide;
N-{2-(2-fluoro-2-[3'-fluoro-4'-(2-(propane-2-sulfonylamino)-ethyl)-biphenyl-4-yl]propyl}-2-propane sulfonamide;
N-(2-{3'-fluoro-4'-[2-(propane-2-sulfonylamino)-ethyl]-biphenyl-4-yl}-2-hydroxypropyl)-2-propane sulfonamide;
N-{2-Fluoro-2-[4-(2-oxo-2,3-dihydro-1H-indol-6-yl)-phenyl]-propyl}-2-propanesulfonamide;
(+)-[2-fluoro-2-(4-iodophenyl)propyl][(methylethyl)sulfonyl]amine;
(−)-[2-fluoro-2-(4-iodophenyl)propyl][(methylethyl)sulfonyl]amine;
[2-fluoro-2-(4-{3-[(methylsulfonyl)amino]phenyl}phenyl)propyl][(methylethyl)sulfonyl]amine (enantiomer 1);
[2-fluoro-2-(4-{3-[(methylsulfonyl)amino]phenyl}phenyl)propyl][(methylethyl)sulfonyl]amine (enantiomer 2);
{4-[4-(1-fluoro-1-methyl-2-{[(methylethyl)sulfonyl]amino}ethyl)phenyl]phenyl}-N-methylcarboxamide (enantiomer 1); and
{4-[4-(1-fluoro-1-methyl-2-{[(methylethyl)sulfonyl]amino}ethyl)phenyl]phenyl}-N-methylcarboxamide (enantiomer 2); and
the pharmaceutically acceptable salts thereof.

13. A compound of the formula:

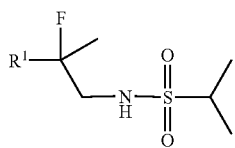

wherein $R^1$ represents an unsubstituted or substituted aromatic group, an unsubstituted or substituted heteroaromatic group, or an unsubstituted or substituted (5–8C)cycloalkyl group; or a pharmaceutically acceptable salt thereof.

14. A compound according to claim 13 wherein $R^1$ represents a substituted aromatic group.

15. A compound according to claim 14 wherein the substituted aromatic group is a substituted phenyl.

16. A compound according to claim 15, wherein the substituted phenyl is substituted with halogen; nitro; cyano; hydroxyimino; (1–10C) alkyl; (2–10C)alkenyl; (2–10C)alkynyl; (3–8C)cycloalkyl; hydroxy(3–8C)cycloalkyl; oxo (3–8C)cycloalkyl; halo(1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached from an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C)alkoxycarbonyl dimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_z X^3 R^{15}$ in which z is 0 or an integer of from 1 to 4, $X^3$ represents O, S, $NR^{16}$, CO, CH(CH), COO, OCO, $CONR^{17}$, $NR^{18}CO$, $NHSO_2$, $SO_2NH$, $NHSO_2NR^{17}$, $OCONR^{19}$ or $NR^{19}COO$, $R^{15}$ represents hydrogen, (1–10C)alkyl, phenyl(1–4C)alkyl, halo (1–10C)alkyl, (1–4C)alkoxycarbonyl(1–4C)alkyl, (1–4C)alkylsulfonylamino(1–4C)alkyl, N-(1–4C)alkoxycarbonyl) (1–4C)alkylsulfonylamino(1–4C)alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo (1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

17. A compound according to claim 16 wherein the substituted phenyl is substituted with a group of formula $R_{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, N-(1–4C)alkoxycarbonyl)(1–4)alkylsulfonylamino (1–4C)alkyl, (3–10C)alkenyl, (3–10C)alkynyl, (3–8C) cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

18. A compound according to claim 17 wherein $(L^a)_n$—$X^2$—$(L^b)_m$ represents a bond, CONH, or $CH_2O$.

19. A compound according to claim 18 wherein $R^{14}$ represents a phenyl which is unsubstituted or substituted by one or two of halogen; nitro; cyano; (1–10C) alkyl; (2–10C) alkenyl; (2–10C)alkynyl; (3–8C)cycloalkyl; 4-(1,1-dioxotetrahydro-1,2-thiazinyl); halo(1–10C)alkyl; cyano (2–10C)alkenyl; phenyl; and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, $OCONR^{19}$ or $NR^{19}COO$, $R^{15}$ represents hydrogen, (1–10C)alkyl, phenyl(1–4C)alkyl, halo(1–10C) alkyl, (1–4C)alkoxycarbonyl(1–4C)alkyl, (1–4C)alkylsulfonylamino(1–4C)alkyl, N-(1–4C)alkoxycarbonyl)(1–4C) alkylsulfonylamino(1–4C)alkyl, (3–10C)alkenyl, (3–10C) alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represent hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

20. A compound according to claim 18 wherein phenyl is substituted by one or two of halogen; nitro; cyano; (1–10C) alkyl; halo(1–10C)alkyl; and $(CH_2)_z X^3 R^{15}$ in which z is 0, 1 or 2, $X^3$ represents O, $NR^{16}$, CO, COO, $CONR^{17}$, $NR^{18}CO$, $NHSO_2$, $SO_2NH$, $NHSO_2R^{17}$, $OCONR^{19}$ or $NR^{19}COO$, $R^{15}$ represents hydrogen, (1–10C)alkyl, phenyl (1–4C)alkyl, halo(1–10C)alkyl, or (3–10C)alkenyl, and $R^{16}$, $R^{17}$, $R^{18}$ and $R^{19}$ each independently represent hydrogen or (1–10C)alkyl.

21. A compound according to claim 18 wherein phenyl is substituted by one or two of fluoro; chloro, cyano; (1–4C) alkyl; trifluoromethyl; and $(CH_2)_z X^3 R^{15}$ in which z is 0, or 2, $X^3$ represents $NR^{16}$, CO, COO, $CONR^{17}$, $NR^{18}CO$, $NHSO_2$, $R^{15}$ represents hydrogen, (1–4C)alkyl, phenyl (1–4C)alkyl, or halo(1–4C)alkyl, and $R^{16}$, $R^{17}$, $R^{18}$ and $R^{19}$ each independently represents hydrogen or (1–4C)alkyl.

22. A compound according to claim 18 wherein phenyl is substituted by one of fluoro; chloro; cyano; (1–4C)alkyl; trifluoromethyl; and $(CH_2)_zX^3R^{15}$ in which z is 0, or 2, $X^3$ represents $NR^{16}$, CO, COO, $CONR^{17}$, $NR^{18}CO$, $NHSO_2$, $R^b$ represents hydrogen, (1–4C)alkyl, phenyl(1–4C)alkyl, or halo(1–4C)alkyl, and $R^{16}$, $R^{17}$, $R^{18}$ and $R^{19}$ each independently represent hydrogen or (1–4C)alkyl.

23. A compound of the formula:

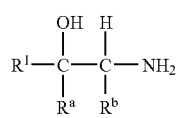

or a pharmaceutically acceptable salt thereof, wherein
  $R^a$ represents (1–6C)alkyl, (2–6C)alkenyl, —(1–4C)alkyl (3–8C)cycloalkyl, or —(1–4C)alkylaromatic;
  $R^b$ represents H, (1–6C)alkyl, (2–6C)alkenyl, —(1–4C) alkyl(3–8C)cycloalkyl, or —(1–4C)alkylaromatic; or
  $R^a$ and $R^b$ together with the carbon atoms to which they attached form a (3–8C) saturated carbocyclic ring, a (3–8C) saturated carbocyclic ring containing a heteroatom selected from the group consisting of sulfur or oxygen, or a (5–8C) carbocyclic ring containing one double bond; and
  $R^1$ is selected from the group consisting of:

a

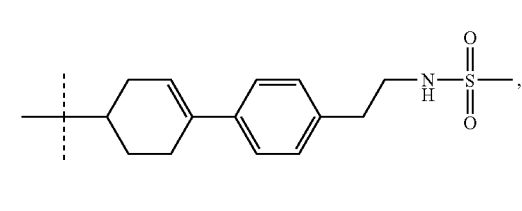

b

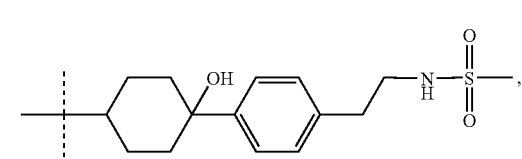

c d e

-continued f

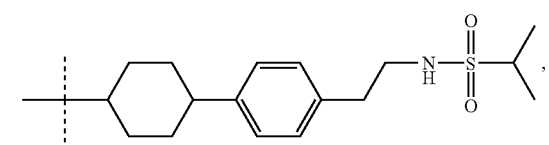

g

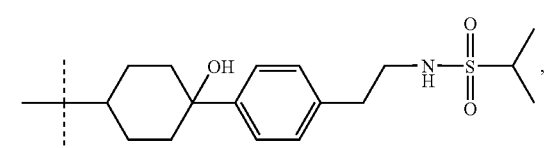

h

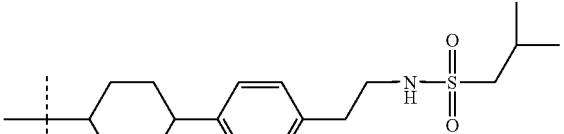

i

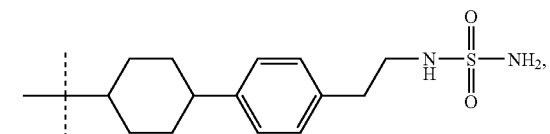

j

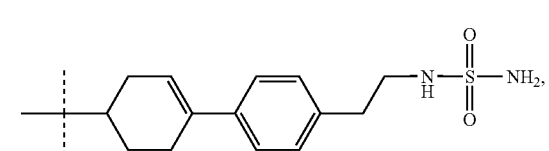

k

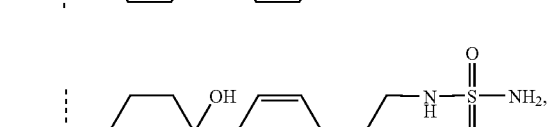

l

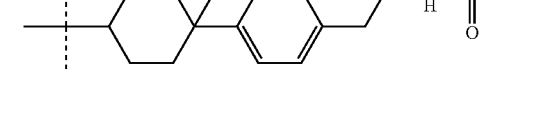

m

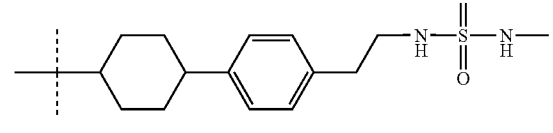

n

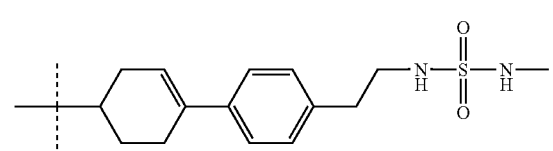

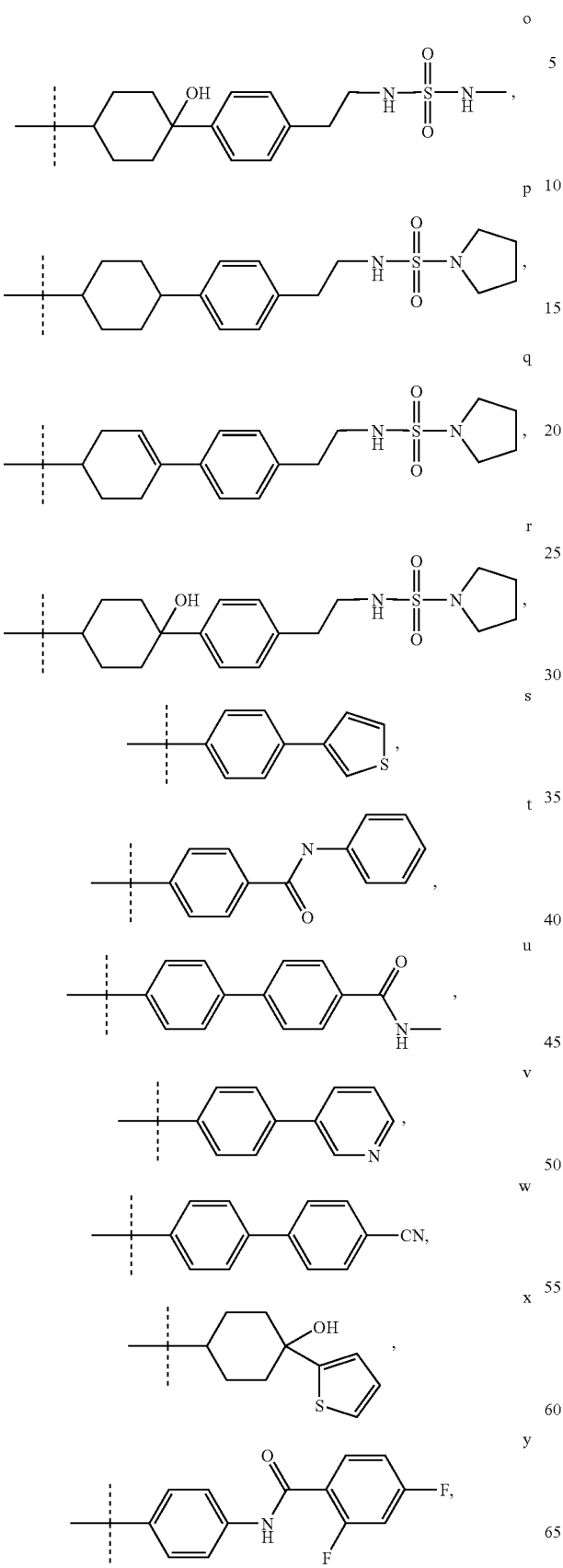
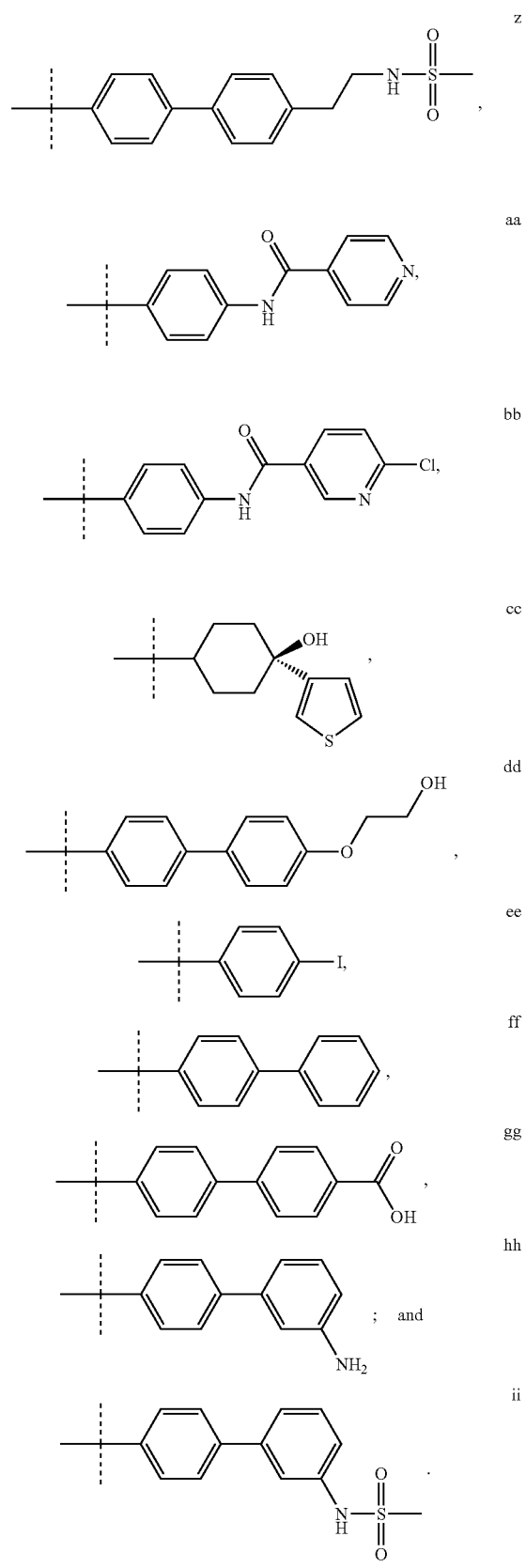

24. A pharmaceutical composition, which comprises a compound as claimed in claim 1 and a pharmaceutically acceptable diluent or carrier.

25. A compound which is selected from the group consisting of:

{4-[4-(1-fluoro-1-methyl-2-{[(methylethyl)sulfonyl]amino}ethyl)phenyl]phenyl}-N-methylcarboxamide; and {4-[4-(1-fluoro-1-methyl-2-{[(methylethyl)sulfonyl]amino}ethyl)phenyl]phenyl}-N-methylcarboxamide (enantiomer 1); and the pharmaceutically acceptable salts thereof.

* * * * *